United States Patent
Qian et al.

(10) Patent No.: US 11,230,549 B2
(45) Date of Patent: Jan. 25, 2022

(54) QUINOLINO-PYRROLIDIN-2-ONE DERIVATIVE AND APPLICATION THEREOF

(71) Applicant: MEDSHINE DISCOVERY INC., Jiangsu (CN)

(72) Inventors: Wenyuan Qian, Shanghai (CN); Chundao Yang, Shanghai (CN); Guoqiang Dai, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 17/280,538

(22) PCT Filed: Sep. 27, 2019

(86) PCT No.: PCT/CN2019/108520
§ 371 (c)(1),
(2) Date: Mar. 26, 2021

(87) PCT Pub. No.: WO2020/063855
PCT Pub. Date: Apr. 2, 2020

(65) Prior Publication Data
US 2021/0380599 A1   Dec. 9, 2021

(30) Foreign Application Priority Data

Sep. 30, 2018   (CN) .......................... 201811157825.9

(51) Int. Cl.
| | |
|---|---|
| *C07D 471/04* | (2006.01) |
| *C07D 471/20* | (2006.01) |
| *C07D 491/20* | (2006.01) |
| *A61K 31/7048* | (2006.01) |
| *A61P 35/00* | (2006.01) |

(52) U.S. Cl.
CPC ........ *C07D 491/20* (2013.01); *A61K 31/7048* (2013.01); *A61P 35/00* (2018.01); *C07D 471/04* (2013.01); *C07D 471/20* (2013.01)

(58) Field of Classification Search
CPC .. C07D 471/04; C07D 471/20; C07D 491/20; A61K 31/7048
USPC ....................................................... 514/278
See application file for complete search history.

(56) References Cited

U.S. PATENT DOCUMENTS

| 8,598,220 B2 | 12/2013 | Brown |
| 2018/0280377 A1 | 10/2018 | Pike et al. |
| 2018/0318287 A1 | 11/2018 | Pike et al. |
| 2020/0325137 A1 | 10/2020 | Fuchss et al. |
| 2021/0198257 A1 | 7/2021 | Fuchss et al. |

FOREIGN PATENT DOCUMENTS

| CN | 102399218 A | 4/2012 |
| CN | 107889488 A | 4/2018 |
| CN | 108348515 A | 7/2018 |
| CN | 108349971 A | 7/2018 |
| RU | 2450006 C2 | 5/2012 |
| WO | WO-2009155527 A2 | 12/2009 |
| WO | 2016155884 A1 | 10/2016 |
| WO | 2017076895 A1 | 5/2017 |
| WO | 2017076898 A1 | 5/2017 |
| WO | WO-2017194632 A1 | 11/2017 |
| WO | 2019201283 | * 10/2019 |
| WO | 2019201283 A1 | 10/2019 |

OTHER PUBLICATIONS

Office Action regarding counterpart Canadian Patent Application No. 3,114,646, dated Jul. 6, 2021.
Examination Report regarding counterpart Indian Patent Application No. 202147018280, dated Jun. 21, 2021.
International Search Report and Written Opinion regarding International Patent Application No. PCT/CN2019/111232, dated Jan. 3, 2020.
Office Action regarding counterpart Korean Patent Application No. 10-2021-7013030, dated Aug. 3, 2021.
Office action dated Sep. 7, 2021 issued in counterpart Japanese application No. 2021-517848.
Oct. 26, 2021 First Office Action issued in European application No. 19865180.4.
Nov. 1, 2021 First Office Action issued in Russian application No. 2021110825.

* cited by examiner

*Primary Examiner* — Niloofar Rahmani
(74) *Attorney, Agent, or Firm* — Harness, Dickey & Pierce, P.L.C.

(57) ABSTRACT

Disclosed are a series of quinolino-pyrrolidin-2-one compounds, and application thereof in preparation of drugs for ATM inhibitor-related diseases. The present disclosure specifically relates to a derivative compound represented by formula (I), tautomers thereof or pharmaceutically acceptable compositions thereof.

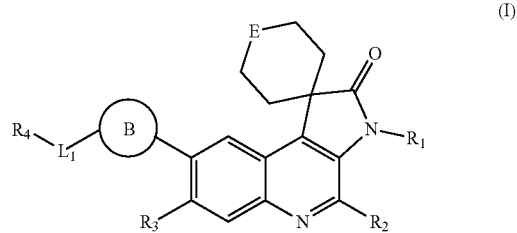

22 Claims, 1 Drawing Sheet

QUINOLINO-PYRROLIDIN-2-ONE DERIVATIVE AND APPLICATION THEREOF

THE PRESENT DISCLOSURE CLAIMS THE FOLLOWING RIGHT OF PRIORITY

The present application is a National Stage of International Application No. PCT/CN2019/108520, filed on Sep. 27, 2019, which claims priority of the Chinese Patent Application No. CN 201811157825.9, application date Sep. 30, 2018, the contents of which are incorporated herein by reference in their entireties.

TECHNICAL FIELD

The present disclosure relates to a series of quinolino-pyrrolidin-2-one compounds, and use thereof in the manufacture of drugs for ATM inhibitor-related diseases. The present disclosure specifically relates to a derivative compound represented by formula (I), tautomers thereof or pharmaceutically acceptable compositions thereof.

BACKGROUND

Ataxia telangiectasia mutated gene (ATM) is an autosomal recessive genetic gene. Homozygotes show a progressive neurodegenerative disease. The patient became ill at about 1 year old, manifested as cerebellar ataxia. Tumor-like small blood vessels dilation appears in the right and left eyes, face and neck at about 6 years old. The patient often died of infection. ATM gene is an important gene related to DNA damage repair, so patients generally manifest as particularly sensitive to X-rays and significantly reduced DNA repair ability. Approximately 1% of humans are heterozygous for ATM mutant genes. Although they do not show disease, they also have increased risk of cancer. ATM gene is located on chromosome 11q22-q23, with a total length of 150 kb, a coding sequence of 12 kb, and a total of 66 exons. ATM gene is one of the human genes with the most exons discovered so far, is also one of the most important genes, and is a house-keeping gene.

The product encoded by ATM gene is an ATM protein, which is a serine/threonine protein kinase comprising 3056 amino acids, has a relative molecular weight of 370 000, is mainly located in the nucleus and microsomes and is involved in the progression of the cell cycle and the responses to cell cycle checkpoints when DNA damage. ATM protein kinase, which is a member of phosphatidylinositol 3-kinase related kinase family (PIKK), is an autophosphorylated protein and usually exists in the form of an inactive dimer. When a double-strand break occurs in DNA, ATM protein kinase is phosphorylated and depolymerized at the earliest few minutes, and the phosphorylated ATM protein kinase reaches a maximum value in 2 to 3 hours.

The signaling pathway of ATM protein in DNA damage repair mainly include: ① ATM-CHK2-Cdc25A/B/C signaling pathway; ② ATM-CHK2-p53 signaling pathway; ③ ATM-Nbs1-Smc1/3 signaling pathway; ④ and ATM-p38MAPK-MK2 signaling pathway. The process by which ATM protein recognizes DNA double-strand breaks and is phosphorylated involves the participation of MRN complexes. M, i.e., MRE11 (meiotic recombination protein) has a nuclease activity and the ability to bind to DNA; R is Rad50, which has an ATPase activity; N means that NBS1 is involved in the localization of the complex in the nucleus and helps the normal assembly of the complex at DNA break point. Various proteins in the MRN complex must coordinate with each other to regulate the ATM protein to bind to the break point of the DNA to help the broken DNA to complete repair.

ATM plays a key role in the repair of DNA double-strand breaks. Since the probability of double-strand breaks in normal cells is small, selective ATM inhibitors have little effect when used alone. However, since ATM is a key link in the entire DNA damage repair pathway, many possible combinations comprise ATM inhibitors. Currently, ATM inhibitors are combined with radiotherapy, chemotherapy, and other target inhibitors for DNA damage repair, such as PARP inhibitors in preclinical and clinical studies. AstraZeneca's AZD0156 is the first compound to enter Phase I clinic. Currently, AZD1390 and M-3541 from Merck, Germany also subsequently enter Phase I clinical study.

Related diseases treated by the ATM kinase inhibitors are solid tumors, wherein the solid tumors include but are not limited to: lung cancer, breast cancer, head and neck cancer, prostate cancer, lymphoma, ovarian cancer, renal cell carcinoma, esophageal cancer, leukemia, bladder cancer, gastric cancer, melanoma, urothelial carcinoma, brain tumor, colorectal cancer, liver cancer, mesothelioma, intrahepatic bile duct carcinoma, etc.

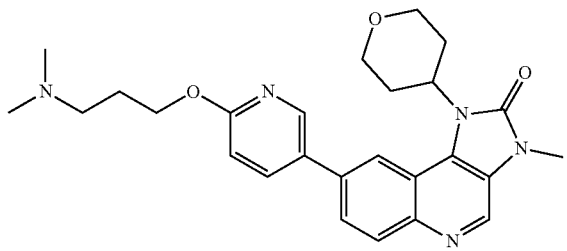

AZD0156

CONTENT OF THE PRESENT INVENTION

The present invention provides a compound represented by formula (I), an isomer thereof or a pharmaceutically acceptable salt thereof,

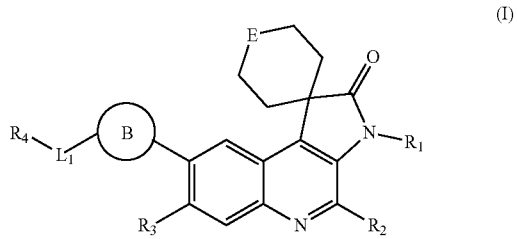

(I)

wherein,

E is selected from $-N(R_5)-$, $-O-$ and $-C(R_6)(R_7)-$;

$R_1$ is selected from $C_{1-3}$ alkyl, $C_{1-3}$ alkoxy and $C_{3-6}$ cycloalkyl, wherein the $C_{1-3}$ alkyl, $C_{1-3}$ alkoxy and $C_{3-6}$ cycloalkyl are optionally substituted with 1, 2 or 3 $R_a$;

$R_2$ is selected from H, F, Cl, Br, I, OH and $NH_2$;

$R_3$ is selected from H, F, Cl, Br, I, OH, $NH_2$, CN, $C_{1-3}$ alkyl and $C_{1-3}$ alkoxy, wherein the $C_{1-3}$ alkyl and $C_{1-3}$ alkoxy are optionally substituted with 1, 2 or 3 $R_b$;

$R_4$ is selected from $C_{1-6}$ alkyl and $N(R_c)(R_d)$;

$R_5$ is selected from H, $C_{1-6}$ alkyl, $C_{3-6}$ cycloalkyl, $C_{1-6}$ alkyl-C=O—, $C_{1-6}$ alkyl-O—C=O— and $C_{3-6}$ cycloalkyl-C=O—, wherein the $C_{1-6}$ alkyl, $C_{3-6}$ cycloalkyl, $C_{1-6}$ alkyl-C=O—, $C_{1-6}$ alkyl-O—C=O— and $C_{3-6}$ cycloalkyl-C=O— are optionally substituted with 1, 2 or 3 $R_e$;

$R_6$ and $R_7$ are each independently selected from H, F, Cl, Br, I, OH, $NH_2$, CN, $C_{1-6}$ alkyl and $C_{1-6}$ alkoxy, wherein the $C_{1-6}$ alkyl or $C_{1-6}$ alkoxy are optionally substituted with 1, 2 or 3 $R_f$;

Li is selected from a single bond, —$(CH_2)_m$— and —$(CH_2)_m$—O—;

m is selected from 1, 2, 3 and 4;

ring B is selected from phenyl and 5- to 6-membered heteroaryl, wherein the phenyl and 5- to 6-membered heteroaryl are optionally substituted with 1, 2 or 3 $R_g$;

$R_a$ and $R_b$ are each independently selected from F, Cl, Br, I, OH and $NH_2$;

$R_c$ and $R_d$ are each independently selected from H, $C_{1-3}$ alkyl and $C_{3-6}$ cycloalkyl, wherein the $C_{1-3}$ alkyl and $C_{3-6}$ cycloalkyl are each independently selected from 1, 2 or 3 R;

or, $R_c$ and $R_d$ together with the N atom to which they are attached form 4- to 6-membered heterocycloalkyl optionally substituted by 1, 2 or 3 R;

$R_e$, $R_f$ and $R_g$ are each independently selected from F, Cl, Br, I, OH and $NH_2$;

each R is independently selected from F, Cl, Br, I, OH and $NH_2$;

and the 5- to 6-membered heteroaryl and 4- to 6-membered heterocycloalkyl are each comprise 1, 2, 3 or 4 heteroatoms or heteroatom groups independently selected from —NH—, —O—, —S— and N.

In some embodiments of the present disclosure, the above-mentioned $R_1$ is selected from $CH_3$, $CH_2CH_3$ and cyclopropyl, wherein the $CH_3$, $CH_2CH_3$ and cyclopropyl are optionally substituted with 1, 2 or 3 $R_a$, and other variables are as defined in the present disclosure.

In some embodiments of the present disclosure, the above-mentioned $R_1$ is selected from $CH_3$, $CH_2F$, $CHF_2$, $CF_3$, $CH_2CH_3$ and cyclopropyl, and other variables are as defined in the present disclosure.

In some embodiments of the present disclosure, the above-mentioned $R_3$ is selected from H, F, Cl, Br, I, OH, $NH_2$, CN, $CH_3$, $CH_2CH_3$ and

wherein the $CH_3$, $CH_2CH_3$ and

are optionally substituted with 1, 2 or 3 $R_b$, and other variables are as defined in the present disclosure.

In some embodiments of the present disclosure, the above-mentioned $R_3$ is selected from H, F, Cl, Br, I, OH, $NH_2$, CN, $CH_3$, $CH_2F$, $CHF_2$, $CF_3$, $CH_2CH_3$ and

and other variables are as defined in the present disclosure.

In some embodiments of the present disclosure, the above-mentioned $R_c$ and $R_d$ are each independently selected from $CH_3$, $CH_2CH_3$ and cyclopropyl, and other variables are as defined in the present disclosure.

In some embodiments of the present disclosure, the above-mentioned $R_c$ and $R_d$ together with the N atom to which they are attached form pyrrolidyl and piperidinyl, wherein the pyrrolidyl and piperidinyl are optionally substituted with 1, 2 or 3 R, and other variables are as defined in the present disclosure.

In some embodiments of the present disclosure, the above-mentioned $R_c$ and $R_d$ together with the N atom to which they are attached form

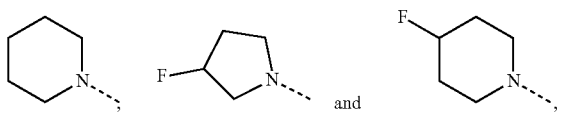

and other variables are as defined in the present disclosure.

In some embodiments of the present disclosure, the above-mentioned $R_4$ is selected from $CH_3$, $CH_2CH_3$,

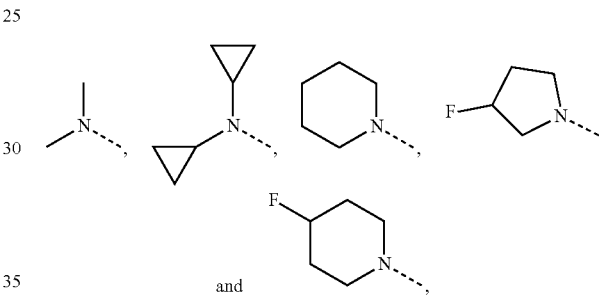

and other variables are as defined in the present disclosure.

In some embodiments of the present disclosure, the above-mentioned $R_5$ is selected from H, $CH_3$, $CH_3CH_2$, $CH(CH_3)_2$, cyclopropyl, $CH_3OC=O$—, $CH(CH_3)_2OC=O$—, $CH_3C=O$— and cyclopropyl-C=O—, wherein the $CH_3$, $CH_3CH_2$, $CH(CH_3)_2$, cyclopropyl, $CH_3OC=O$—, $CH(CH_3)_2OC=O$—, $CH_3C=O$— and cyclopropyl-C=O— are optionally substituted with 1, 2 or 3 $R_e$, and other variables are as defined in the present disclosure.

In some embodiments of the present disclosure, the above-mentioned $R_5$ is selected from H, $CH_3$, $CH_2F$, $CHF_2$, $CF_3$, $CH_3CH_2$, $CH_2FCH_2$, $CHF_2CH_2$, $CF_3CH_2$, $CH(CH_3)_2$, cyclopropyl, $CH_3OC=O$—, $CH(CH_3)_2OC=O$—, $CH_3C=O$— and cyclopropyl-C=O—, and other variables are as defined in the present disclosure.

In some embodiments of the present disclosure, the above-mentioned $R_6$ and $R_7$ are each independently selected from H, F, Cl, Br, I, OH, $NH_2$, CN, $CH_3$, $CH_3CH_2$, $CH(CH_3)_2$ and

wherein the $CH_3$, $CH_3CH_2$, $CH(CH_3)_2$ and

are optionally substituted with 1, 2 or 3 $R_f$, and other variables are as defined in the present disclosure.

In some embodiments of the present disclosure, the above-mentioned $R_6$ and $R_7$ are each independently selected from H, F, Cl, Br, I, OH, $NH_2$, CN, $CH_3$, $CH_2F$, $CHF_2$, $CF_3$, $CH_3CH_2$, $CH(CH_3)_2$ and

and other variables are as defined in the present disclosure.

In some embodiments of the present disclosure, the above-mentioned E is selected from —O—, —$CF_2$—, —N($CH_3$)—, —NH—,

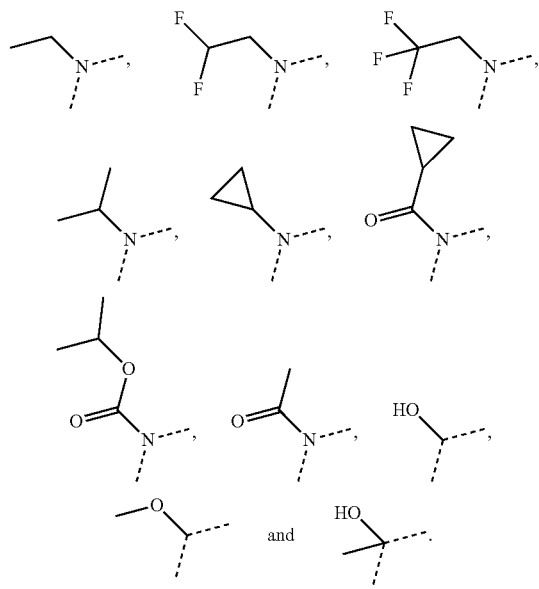

In some embodiments of the present disclosure, the above-mentioned Li is selected from a single bond, —($CH_2$)—O— and —($CH_2$)$_3$—O—, and other variables are as defined in the present disclosure.

In some embodiments of the present disclosure, the above-mentioned ring B is selected from phenyl, pyridyl, pyrazolyl, indazolyl and imidazolyl, wherein the phenyl, pyridyl, pyrazolyl, indazolyl and imidazolyl are optionally substituted with 1, 2 or 3 $R_g$, and other variables are as defined in the present disclosure.

In some embodiments of the present disclosure, the above-mentioned ring B is selected from

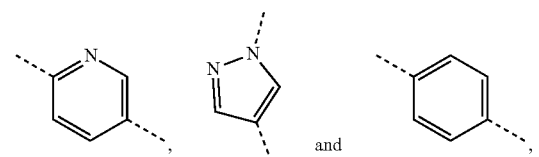

wherein the

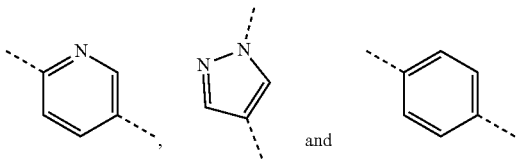

are optionally substituted with 1, 2 or 3 $R_g$, and other variables are as defined in the present disclosure.

In some embodiments of the present disclosure, the above-mentioned ring B is selected from

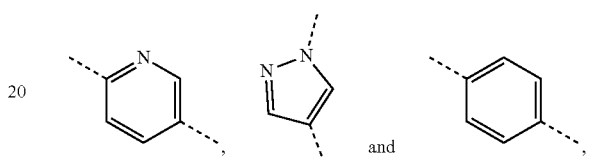

and other variables are as defined in the present disclosure.

In some embodiments of the present disclosure, the above-mentioned $R_4$-$L_1$- is selected from $CH_3$, $CH_3OCH_2$—,

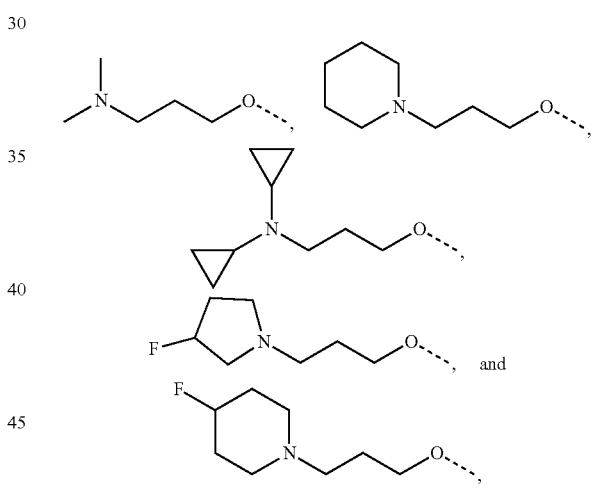

and other variables are as defined in the present disclosure.

Other solutions of the present disclosure are generated by any combination of the above variables.

In some embodiments of the present disclosure, the above-mentioned compound, isomer thereof or pharmaceutically acceptable salt thereof is selected from

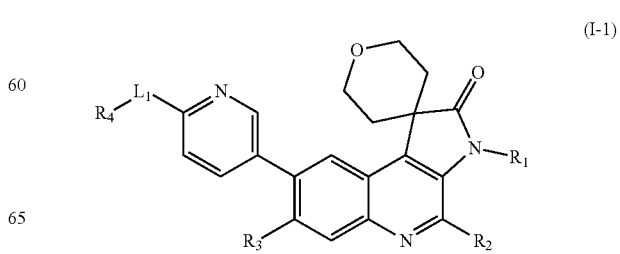

(I-1)

-continued
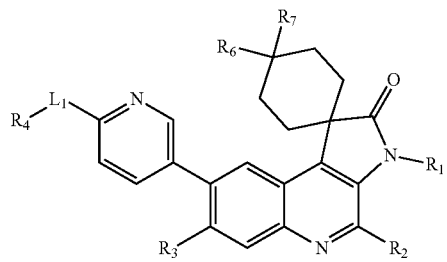
(I-2)
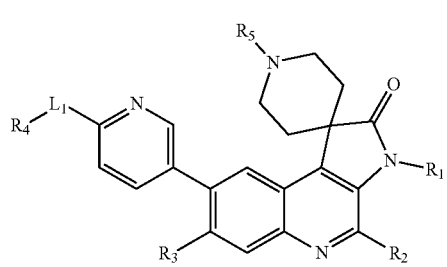
(I-3)
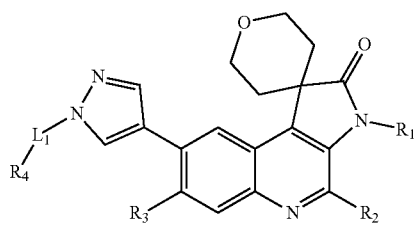
(I-4)
wherein
R₁, R₂, R₃, R₄, R₅, R₆, R₇ and L₁ are as defined in the present disclosure.
The present disclosure also provides the following compound, isomer thereof or pharmaceutically acceptable salt thereof, wherein the compound is selected from
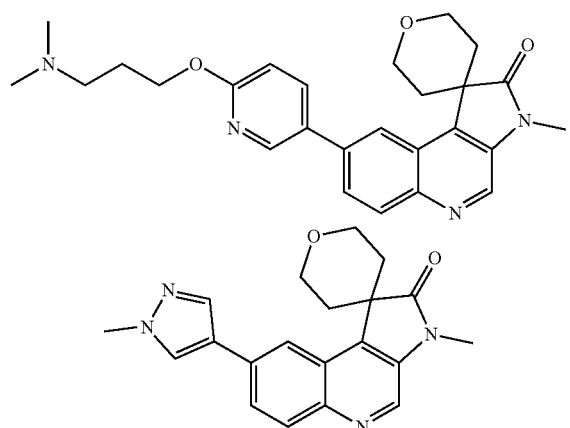
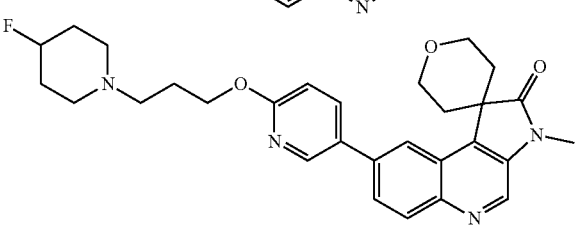
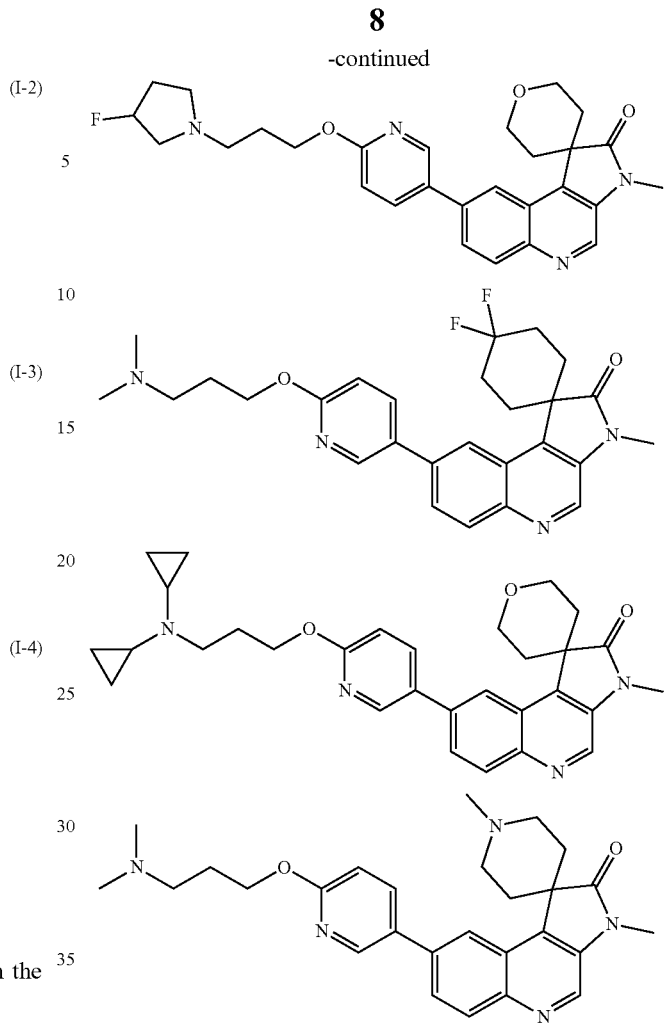

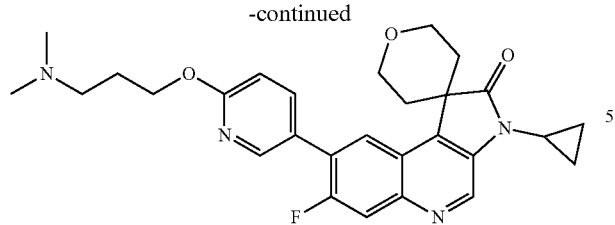
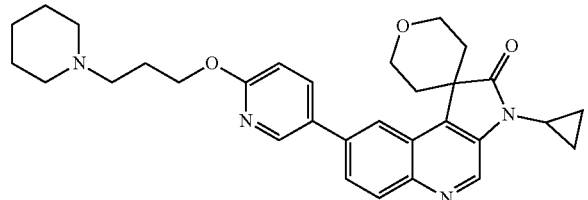
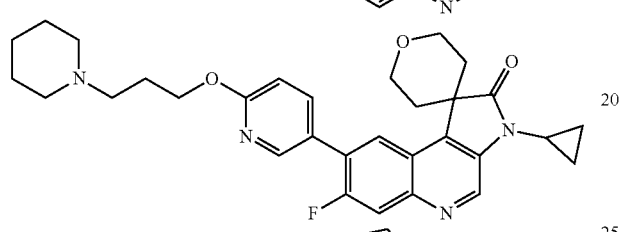
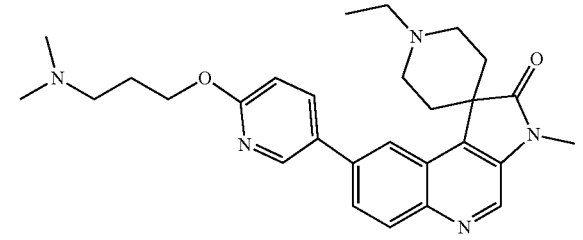
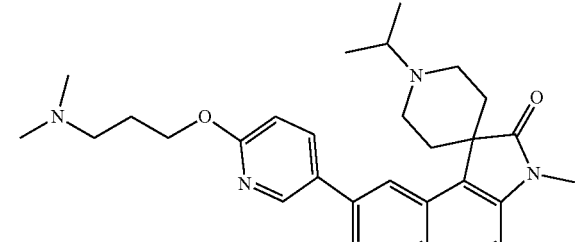
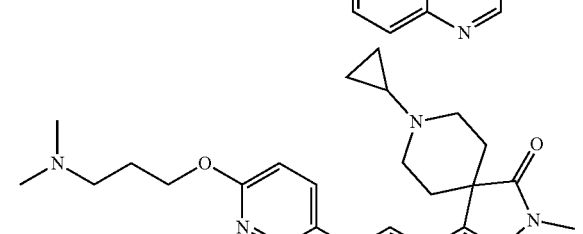
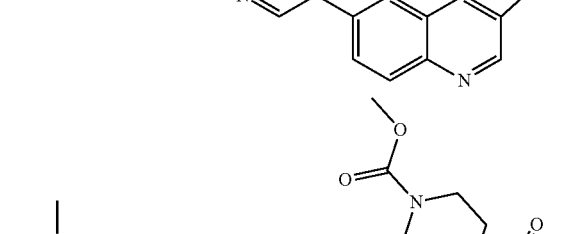
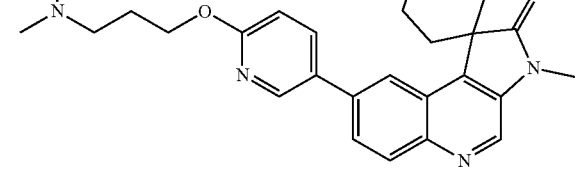
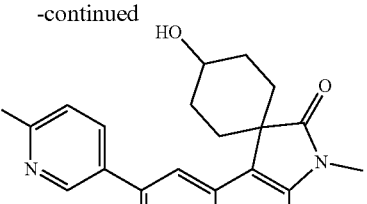
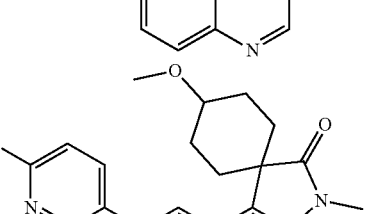
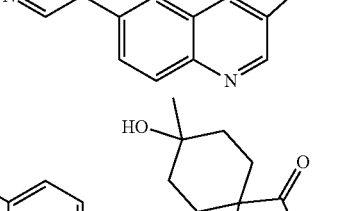
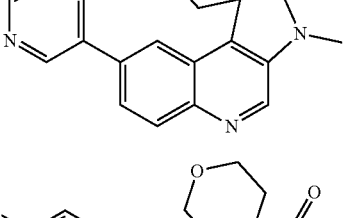
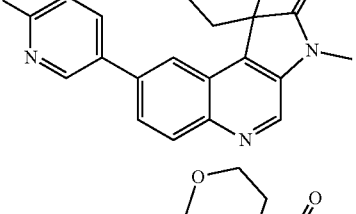
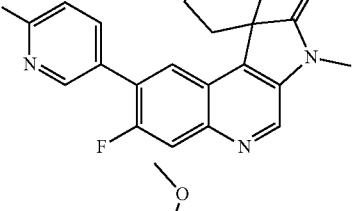
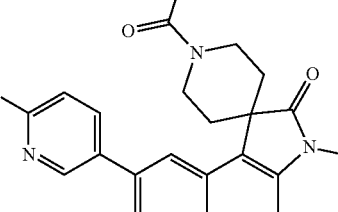
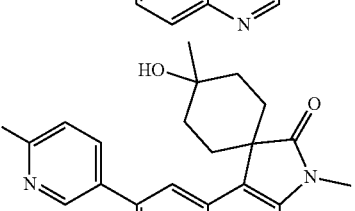

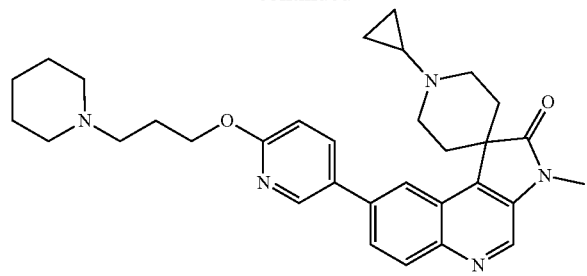
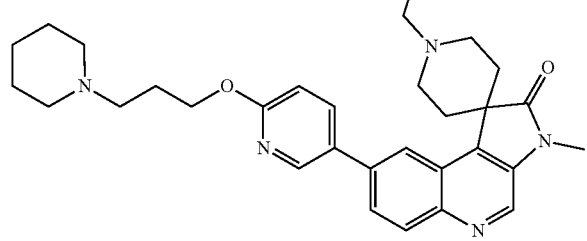
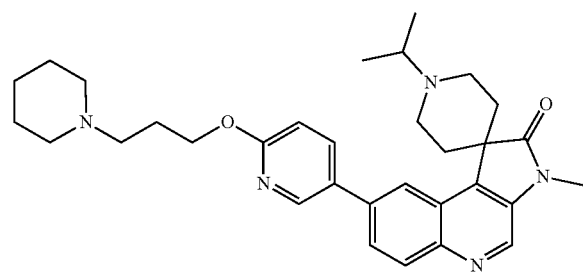
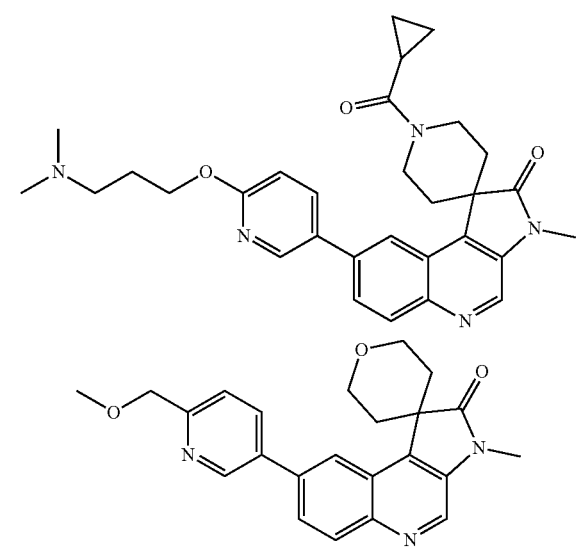
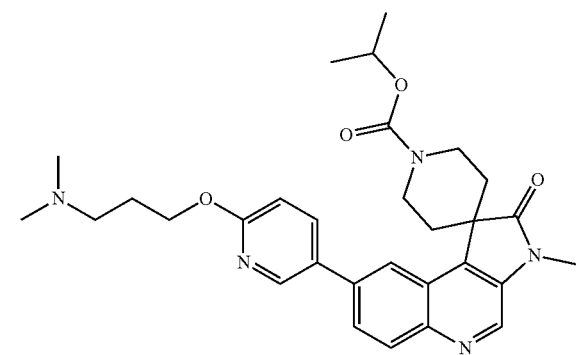
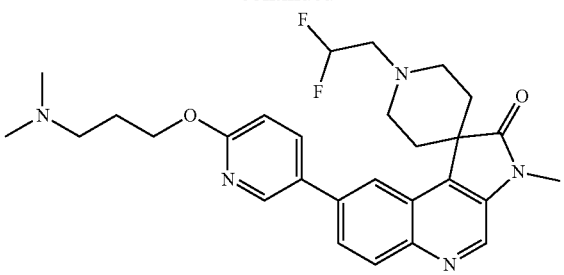
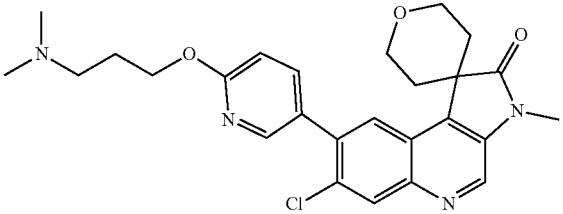
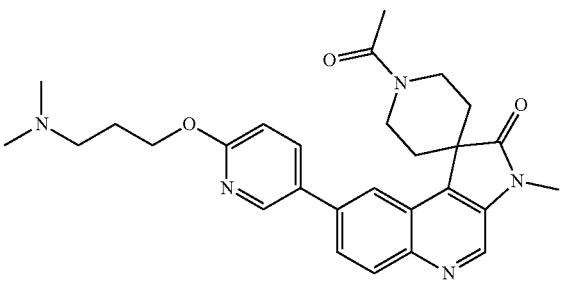
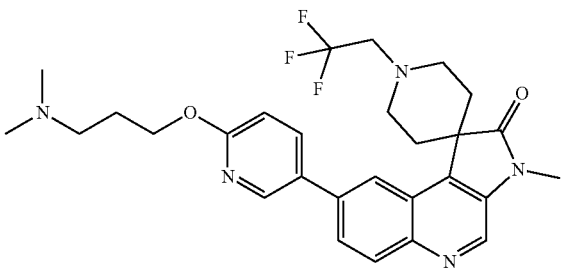
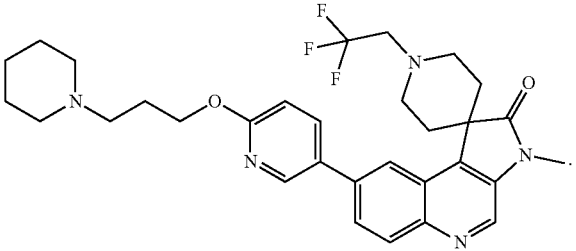
In some embodiments of the present disclosure, the above-mentioned compound, isomer thereof or pharmaceutically acceptable salt thereof is selected from
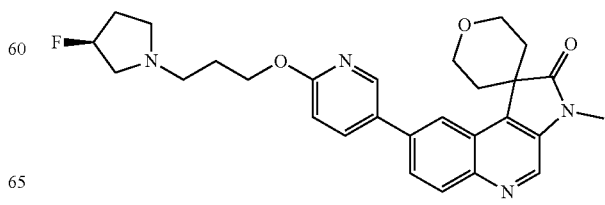

-continued

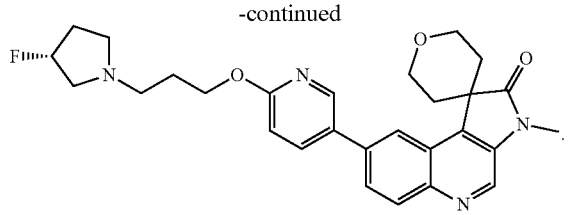

In some embodiments of the present disclosure, provided is uses of the above-mentioned compound, isomer thereof or pharmaceutically acceptable salt thereof in the manufacture of ATM kinase inhibitor-related drugs.

In some embodiments of the present disclosure, the above-mentioned application, wherein the ATM kinase inhibitor-related drugs are drugs for solid tumors.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof.

The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present disclosure, which is prepared from the compound having specific substituents found in the present disclosure with relatively non-toxic acids or bases. When compounds of the present disclosure contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amino or magnesium salts or similar salts. When compounds of the present disclosure contain relatively basic functional groups, acid addition salts can be obtained by contacting the neutral form of such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and also include salts of amino acids (such as arginine), and salts of organic acids such as glucuronic acid. Certain specific compounds of the present disclosure contain basic and acidic functional groups and thus can be converted to any base or acid addition salt.

The pharmaceutically acceptable salts of the present disclosure can be synthesized from a parent compound containing acid radicals or base radicals by conventional chemical methods. In general, the method for preparing such salts comprises: in water or an organic solvent or a mixture of both, reacting these compounds in free acid or base forms with a stoichiometric amount of a suitable base or acid to prepare the salts.

The structure of the compound of the present disclosure can be confirmed by conventional methods well known to a person skilled in the art. If the present disclosure relates to the absolute configuration of the compound, the absolute configuration can be confirmed by conventional technical means in the art. For example, single-crystal X-ray diffraction (SXRD) uses a Bruker D8 venture diffractometer to collect the diffraction intensity data of the cultivated single crystal, the light source is CuKα radiation, and the scanning mode is φ/ω scanning. After the related data is collected, a direct method (Shelxs97) is further used to resolve the crystal structure, so that the absolute configuration can be confirmed.

The compounds of the present disclosure may exist in specific geometric or stereoisomeric forms. The present invention contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present invention. Additional asymmetric carbon atoms may be present in a substituent such as an alkyl group. All these isomers and mixtures thereof are included in the scope of the present disclosure.

Unless otherwise stated, the term "enantiomer" or "optical isomers" refers to stereoisomers that are mirror images of each other.

Unless otherwise stated, the term "cis-trans isomer" or "geometric isomer" is caused by the fact that double bonds or single bonds of ring-forming carbon atoms cannot rotate freely.

Unless otherwise stated, the term "diastereomers" refers to stereoisomers in which molecules have two or more chiral centers and are not mirror images of each other.

Unless otherwise stated, "(D)" or "(+)" means dextrorotatory, "(L)" or "(−)" means levorotatory, and "(DL)" or "(±)" means racemic.

Unless otherwise stated, the wedge-shaped solid bond ( ◢ ) and the wedge-shaped dotted bond ( ⋰ ) represent the absolute configuration of a stereoscopic center; the straight solid bond ( ◢ ) and straight dotted bond ( ⋰ ) represent the relative configuration of a stereoscopic center; the wavy line ( ∿ ) represents the wedge-shaped solid bond ( ◢ ) or the wedge-shaped dotted bond ( ⋰ ); or the wavy line ( ∿ ) represents the straight solid bond ( ◢ ) and the straight dotted bond ( ⋰ ).

Unless otherwise stated, when there is a double bond structure in the compound, such as a carbon-carbon double bond, a carbon-nitrogen double bond, and a nitrogen-nitrogen double bond, and each atom on the double bond is connected to two different substituents (in a double bond containing a nitrogen atom, a lone pair of electrons on the nitrogen atom is regarded as a substituent connected to it), if the atom on the double bond in the compound and its substituent are connected by the wavy line ( ~ ), it represents the (Z) isomer, (E) isomer or a mixture of two isomers of the compound. For example, the following formula (A) indicates that the compound is in the form of a single isomer of formula (A-1) or formula (A-2) or a mixture of two isomers of formula (A-1) and formula (A-2); the following formula (B) indicates that the compound is in the form of a single isomer of formula (B-1) or formula (B-2) or a mixture of two isomers of formula (B-1) and formula (B-2). The following formula (C) indicates that the compound is in the form of a single isomer of formula (C-1) or formula (C-2) or a mixture of two isomers of formula (C-1) and formula (C-2).

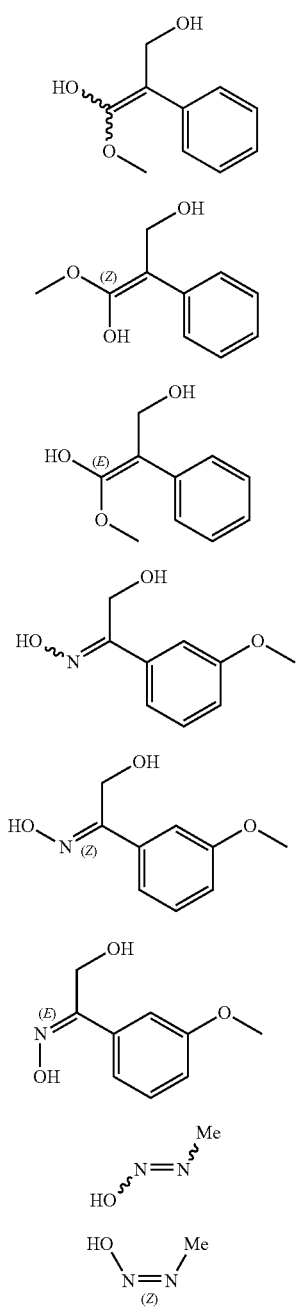

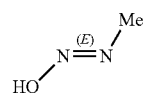

The compounds of the present disclosure may exist in specific. Unless otherwise stated, the term "tautomer" or "tautomeric form" means that at room temperature, isomers with different functional groups are in dynamic equilibrium and can be quickly converted to each other. Where tautomerization is possible (such as in solution), a chemical equilibrium of tautomers can be achieved. For example, proton tautomers (also known as prototropic tautomers) include interconversion via migration of a proton, such as keto-enol isomerization and imine-enamine isomerization. Valence tautomers include some interconversions by recombination of some of bond-forming electrons. A specific example of keto-enol tautomerization is the interconversion between two tautomers, pentane-2,4-dione and 4-hydroxypent-3-en-2-one.

Unless otherwise stated, the terms "rich in one isomer", "isomer enriched", "rich in one enantiomer" or "enantiomerically enriched" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomers and D and L isomers can be prepared using chiral synthesis or chiral reagents or other conventional techniques. If a particular enantiomer of a compound of the present disclosure is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines). The compounds of the present disclosure may contain unnatural proportions of atomic isotopes at one or more of the atoms constituting the compound. For example, the compounds may be radiolabeled with radioactive isotopes, such as tritium ($^3H$), iodine-125 ($^{125}I$) or C-14 ($^{14}C$). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present disclosure, whether radioactive or not, are intended to be encompassed within the scope of the present disclosure. "Optional" or "optionally" means that the subsequently described event or circumstance may, but not necessarily occur, and that the description includes instances where said event or circumstance occurs and instances where said event or circumstance does not occur.

The term "substituted" means that any one or more hydrogen atoms on the designated atom is substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups. The term "optionally substituted" means that it may or may not be substituted. Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2 R, the group can optionally be substituted with up to two R, and R in each case has independent options. In addition, combinations of substituents and/or variants thereof are permissible only if such combinations result in stable compounds.

When the number of a linking group is 0, such as —(CRR)$_0$—, it means that the linking group is a single bond.

When one of the variables is selected from a single bond, it means that the two groups to which it is connected are directly connected. For example, when L represents a single bond in A-L-Z, it means that the structure is actually A-Z.

When a substituent is vacant, it means that the substituent does not exist. For example, when X is vacant in A-X, it means that the structure is actually A. When the substituents listed do not indicate through which atom they are connected to the substituted group, such substituents can be bonded through any of the atoms thereof, for example, pyridyl as a substituent can be attached to the substituted group via any carbon atom on the pyridine ring.

When the linking group listed does not indicate the linking direction thereof, the linking direction is arbitrary, for example, the linking group L is -M-W— in

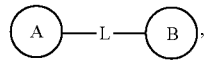

at this situation, -M-W— can connect ring A and ring B in the same direction as the reading order from left to right to form

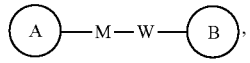

and can also connect ring A and ring B in the opposite direction as the reading order from left to right to form

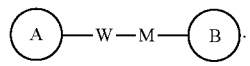

Combinations of the linking groups, substituents, and/or variants thereof are permissible only if such combinations result in stable compounds.

Unless otherwise specified, the number of atoms in a ring is usually defined as the member number of the ring. For example, "5- to 7-membered ring" means a "ring" with 5-7 atoms arranging in a circle.

Unless otherwise specified, the term "$C_{1-6}$ alkyl" is used to represent a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl; It can be monovalent (such as methyl), divalent (such as methyl) or multivalent (such as methine). Examples of $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl) and hexyl.

Unless otherwise specified, the term "$C_{1-3}$ alkyl" is used to represent a linear or branched saturated hydrocarbon group consisting of 1 to 3 carbon atoms. The $C_{1-3}$ alkyl includes $C_{1-2}$ and $C_{2-3}$ alkyl; It can be monovalent (such as methyl), divalent (such as methyl) or multivalent (such as methine). Examples of $C_{1-3}$ alkyl include, but are not limited to, methyl (Me), ethyl (Et) and propyl (including n-propyl and isopropyl).

Unless otherwise specified, the term "$C_{1-6}$ alkoxy" means those alkyl groups containing 1 to 6 carbon atoms that are connected to the rest of the molecule through one oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$, $C_3$ alkoxy, etc. Examples of $C_{1-6}$ alkoxy include but are not limited to methoxy, ethoxy, propoxy (including n-propoxy and isopropoxy), butoxy (including n-butoxy, isobutoxy, s-butoxy and t-butoxy), pentyloxy (including n-pentyloxy, isopentyloxy and neopentyloxy), hexyloxy, etc.

Unless otherwise specified, the term "$C_{1-3}$ alkoxy" means those alkyl groups containing 1 to 3 carbon atoms that are connected to the rest of the molecule through one oxygen atom. The $C_{1-3}$ alkoxy group includes $C_{1-2}$, $C_{2-3}$, $C_3$, $C_2$ alkoxy, etc. Examples of Ci-3 alkoxy include but are not limited to methoxy, ethoxy, propoxy (including n-propoxy and isopropoxy), etc.

Unless otherwise specified, "$C_{3-6}$ cycloalkyl" means a saturated cyclic hydrocarbon group consisting of 3 to 6 carbon atoms, which comprises a monocyclic and bicyclic ring system, and the $C_{3-6}$ cycloalkyl includes $C_{3-5}$, $C_{4-5}$, and $C_{5-6}$ cycloalkyl; It can be monovalent, bivalent or multivalent. Examples of $C_{3-6}$ cycloalkyl include, but are not limited to, cyclopropyl, cyclobutyl, cyclopentyl and cyclohexyl.

Unless otherwise specified, the term "4- to 6-membered heterocycloalkyl" by itself or in combination with other terms respectively represents a saturated cyclic group consisting of 4 to 6 ring atoms, of which 1, 2, 3 or 4 ring atoms are heteroatoms independently selected from O, S and N, and the rest of which are carbon atoms, wherein the nitrogen atom is optionally quaternized, and the nitrogen and sulfur heteroatoms can be optionally oxidized (i.e., NO and $S(O)_p$, wherein p is 1 or 2). It comprises a monocyclic and bicyclic ring system, wherein the bicyclic system includes a spiro ring, a fused ring, and abridged ring. In addition, in terms of the "4- to 6-membered heterocycloalkyl", the heteroatom may occupy the connection position of the heterocyclic alkyl to the remainder of the molecule. The 4- to 6-membered heterocycloalkyl includes 5- to 6-membered, 4-membered, 5-membered and 6-membered heterocycloalkyl, etc. Examples of 4- to 6-membered heterocycloalkyl include, but are not limited to, azetidinyl, oxetanyl, thiatanyl, pyrrolidinyl, pyrazolidinyl, imidazolidinyl, tetrahydrothienyl (including tetrahydrothiophene-2-yl, tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, or homopiperidinyl, etc.

Unless otherwise specified, the terms "5- to 6-membered heteroaryl ring" and "5- to 6-membered heteroaryl" of the present disclosure can be used interchangeably, and the term "5- to 6-membered heteroaryl" represents a monocyclic group having a conjugated π-electron system and consisting of 5 to 6 ring atoms, of which 1, 2, 3, or 4 ring atoms are heteroatoms independently selected from O, S, and N, and the rest of which are carbon atoms. wherein nitrogen atoms are optionally quaternized, and nitrogen and sulfur heteroatoms can be optionally oxidized (i.e., NO and $S(O)_p$, wherein p is 1 or 2). The 5- to 6-membered heteroaryl can be connected to the remainder of the molecule via a heteroatom or a carbon atom. The 5- to 6-membered heteroaryl includes 5-membered and 6-membered heteroaryl. Examples of the 5- to 6-membered heteroaryl include, but are not limited to, pyrrolyl (including N-pyrrolyl, 2-pyrrolyl and 3-pyrrolyl), pyrazolyl (including 2-pyrazolyl and 3-pyrazolyl), imidazolyl (including N-imidazolyl, 2-imidazolyl, 4-imidazolyl and 5-imidazolyl), oxazolyl (including 2-oxazolyl, 4-oxazolyl and 5-oxazolyl), triazolyl (1H-1,2,3-triazolyl, 2H-1,2,3-triazolyl, 1H-1,2,4-triazolyl and 4H-1,2,4-triazolyl), tetrazolyl, isoxazolyl (3-isoxazolyl, 4-isoxazolyl and 5-isoxazolyl), thiazolyl (including 2-thiazolyl, 4-thiazolyl and 5-thiazolyl), furyl (including 2-furanyl and 3-furanyl), thienyl (including 2-thienyl and 3-thienyl), pyridyl (including 2-pyridyl, 3-pyridyl and 4-pyridyl), pyrazinyl or pyrimidinyl (including 2-pyrimidyl and 4-pyrimidyl).

Unless otherwise specified, $C_{n-n+m}$ or $C_n-C_{n+m}$ includes any specific case of n to n+m carbons, for example, $C_{1-12}$ includes $C_1, C_2, C_3, C_4, C_5, C_6, C_7, C_8, C_9, C_{10}, C_{11}$ and $C_{12}$, and also includes any range from n to n+m, for example, $C_{1-12}$ includes $C_{1-3}, C_{1-6}, C_{1-9}, C_{3-6}, C_{3-9}, C_{3-12}, C_{6-9}, C_{6-12}$ and $C_{9-12}$; Similarly, n-membered to n+m-membered means that the number of atoms in the ring is n to n+m, for example, a 3- to 12-membered ring includes a 3-membered ring, a 4-membered ring, a 5-membered ring, a 6-membered ring, a 7-membered ring, a 8-membered ring, a 9-membered ring, a 10-membered ring, a 11-membered ring, and a 12-membered ring, and also includes any range from n to n+m, for example, a 3- to 12-membered ring includes a 3- to 6-membered ring, a 3- to 9-membered ring, a 5- to 6-membered ring, a 5- to 7-membered ring, a 6- to 7-membered ring, a 6- to 8-membered ring, and a 6- to 10-membered ring.

The term "leaving group" refers to a functional group or atom that can be substituted by another functional group or atom through a substitution reaction (e.g., an affinity substitution reaction). For example, representative leaving groups include trifluoromethanesulfonate; chlorine, bromine and iodine; sulfonates, such as methanesulfonate, tosylate, p-bromobenzenesulfonate, and p-toluenesulfonate; and acyloxy, such as acetoxy and trifluoroacetoxy.

The term "protecting group" includes, but is not limited to, "amino protecting group", "hydroxy protecting group" or "mercapto protecting group". The term "amino protecting group" refers to a protecting group suitable for preventing side reactions occur at the nitrogen atom of an amino group. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl)methyl; silyl, such as trimethylsilyl (TMS) and tert-butyldimethylsilyl (TBS). The term "hydroxyl protecting group" refers to a protecting group suitable for preventing side reactions of a hydroxyl group. Representative hydroxyl protecting groups include, but are not limited to: alkyl, such as methyl, ethyl and tert-butyl; acyl, such as alkanoyl (e.g., acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TBS).

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The solvents used in the present disclosure are commercially available. The present disclosure uses the following abbreviations: aq represents water; HATU represents O-(7-azabenzotriazol-1-yl)-N,N,N',N'-tetramethylurea hexafluorophosphate; EDC represents N-(3-dimethylaminopropyl)-N'-ethylcarbodiimide hydrochloride; m-CPBA represents 3-chloroperoxybenzoic acid; eq represents equivalent; CDI represents carbonyldiimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amine protecting group; BOC represents tert-butoxycarbonyl, which is an amine protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; NFSI represents N-fluoro-N-(benzenesulfonyl)benzenesulfonamide; NCS represents 1-chloropyrrolidine-2,5-dione; n-$Bu_4NF$ represents tetrabutylammonium fluoride; iPrOH represents 2-propanol; mp represents melting point; LDA represents lithium diisopropylamide; LiHMDS represents lithium hexamethyldisilazide; Xantphos represents 4,5-bis-diphenylphosphino-9,9-dimethylxanthene; $LiAlH_4$ represents lithium aluminium tetrahydride; $Pd(dba)_2$ represents tris(dibenzylideneacetone)dipalladium; mCPBA represents m-chloroperoxybenzoic acid; $pd(dppf)Cl_2$ represents [1,1'-bis(diphenylphosphino)ferrocene]palladium dichloride; DBU represents 1,8-diazabicyclo[5.4.0]undecen-7-en; DIPA represents diisopropylamine; n-BuLi represents n-butyllithium; NBS represents N-bromosuccinimide; MeI represents iodomethane; TBAB represents tetrabutylammonium bromide; $Pd(PPh_3)_4$ represents tetrakistriphenylphosphine palladium; MeCN represents acetonitrile; NaH represents sodium hydride; TBSOTf represents (tert-butyldimethylsilyl)trifluoromethanesulfonate.

Compounds are named by hand or ChemDraw® software, and commercially available compounds are named by the supplier catalog names.

Technical Effects

The compound of the present disclosure has a significant ATM kinase inhibitory effect and very good kinase selectivity, good solubility and permeability, can penetrate the brain, and has the potential to be developed into a drug for treating brain tumors. The combination of the compound of the present disclosure and etoposide shows a good synergistic effect, which is better than the efficacy of AZD0156 in combination with etoposide.

DETAILED DESCRIPTION OF THE PREFERRED EMBODIMENT

Figure 1:
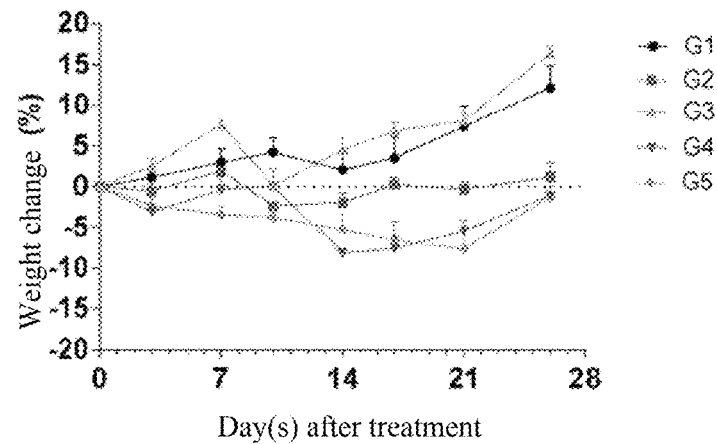
FIG. 1: relative weight change.

The present disclosure will be described in detail with the following examples, but not imply any adverse limitation to the present disclosure. The present disclosure has been described in detail herein, and the specific embodiments thereof are also disclosed therein. For a person skilled in the art, without departing from the spirit and scope of the present disclosure, all the variations and improvements made to the specific embodiments of the present disclosure would have been obvious.

Intermediate A

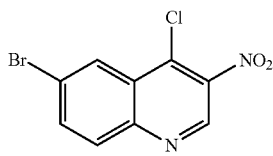

Synthetic Route

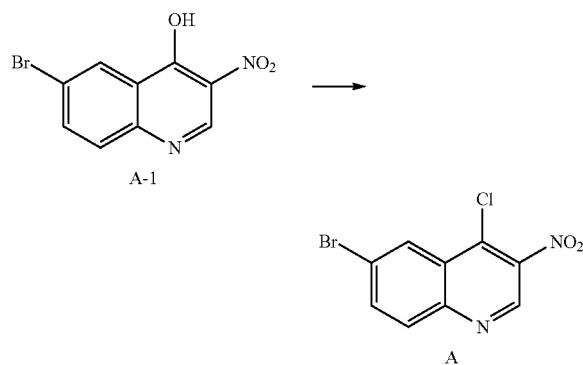

Step 1: Synthesis of Intermediate A

DMF (95.00 mg, 1.30 mmol, 0.1 mL) was added to a solution of compound A-1 (34 g, 126.37 mmol) in $SOCl_2$ (200 mL), and the reaction solution was stirred at 80° C. for 16 hours. After completion of the reaction, $SOCl_2$ was removed under reduced pressure to obtain a crude A, which was directly used in the next step.

MS m/z: 286.7$[M+H]^+$ $^1H$ NMR (400 MHz, DMSO-$d_6$) δ 9.20 (s, 1H), 8.29 (d, J=2.3 Hz, 1H), 7.94 (dd, J=2.3, 8.8 Hz, 1H), 7.72 (d, J=8.8 Hz, 1H)

Intermediate B

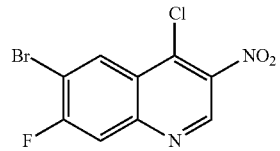 [SMILES: O=[N+]([O-])c1cnc2cc(F)c(Br)cc2c1Cl]

Synthetic Route

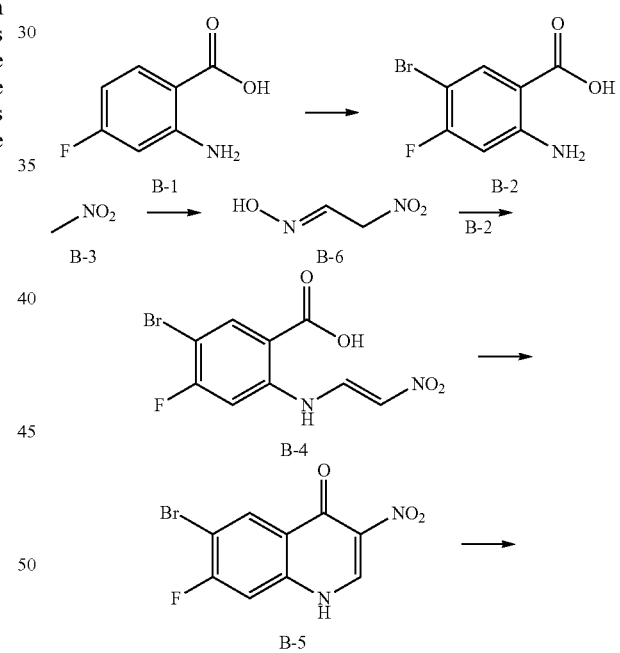

Step 1: Synthesis of Compound B-2

At 0° C. and under nitrogen protection, a solution of NBS (30.12 g, 169.22 mmol) in DMF (100 mL) was added to a solution of B-1 (25 g, 161.16 mmol) in DMF (100 mL), and the reaction system was stirred at 30° C. for 2 h. After completion of the reaction, the mixture was concentrated under reduced pressure to remove the reaction solvent, then slurried for 30 minutes with water (100 mL), and then washed with acetonitrile (10 mL) to obtain B-2.

MS m/z: 233.8[M+H]$^+$ $^1$H NMR (400 MHz, DMSO-d$_6$) δ 7.88 (br d, J=7.88 Hz, 1H), 6.69 (br d, J=11.38 Hz, 1H)

Step 2: Synthesis of Compound B-6

In a round-bottom flask, nitromethane (18 g, 294.89 mmol, 15.93 mL) (B-3) was added slowly to a solution of NaOH (17.69 g, 442.33 mmol) in H$_2$O (100 mL), and the internal temperature was kept at 30° C. Then the mixture was heated to 40° C. and stirred for 30 minutes, and cooled. Then another part of nitromethane (18.00 g, 294.89 mmol, 15.93 mL) was slowly added, the reaction system was heated to 45° C. and stirred for 30 minutes, and then raised to 50° C.-55° C. and stirred for 5 minutes to obtain a mixed solution of B-6, which was directly used in the next step.

Step 3: Synthesis of Compound B-4

A mixed solution of B-6 was cooled to 30° C., and ice (80 g) and concentrated hydrochloric acid (15 mL) were added. The above-mentioned mixed solution was added to a solution of B-2 (34.3 g, 146.57 mmol) in HCl (12 M, 90 mL) and H$_2$O (200 mL), and stirred at 30° C. for 12 h. A solid was precipitated, and filtered. The filter cake was collected, and then washed with acetonitrile (50 mL) to obtain compound B-4.

MS m/z: 304.7[M+H]$^+$ $^1$H NMR (400 MHz, DMSO-d$_6$) δ 12.99 (br d, J=12.5 Hz, 1H), 8.23-8.13 (m, 1H), 8.08-7.96 (m, 1H), 7.88 (br d, J=10.5 Hz, 1H), 6.80 (br s, 1H)

Step 4: Synthesis of Compound B-5

Under nitrogen protection, a solution of B-4 (44 g, 111.06 mmol) in acetic anhydride (397.79 g, 3.90 mol, 364.94 mL) was heated at 100° C. for 1 h, and then heating was discontinued. Sodium acetate (9.38 g, 114.39 mmol) was added, and refluxed at 150° C. for 15 minutes. Finally, another portion of sodium acetate (9.38 g, 114.39 mmol) was added, and the reaction system was refluxed at 150° C. for 1 h. After completion of the reaction, the solvent was removed by concentration. The residual solids were slurried with water (200 mL) for 1 h, then slurried with a mixed solution of EtOAc and methanol (55 mL, EtOAc:MeOH=10:1) for 1 h, and filtered to obtain compound B-5.

MS m/z: 287.0[M+H]$^+$ $^1$H NMR (400 MHz, DMSO-d$_6$) δ 9.25 (s, 1H), 8.44 (d, J=7.5 Hz, 1H), 7.63 (br d, J=9.3 Hz, 1H)

Step 5: Synthesis of Intermediate B

Except for using the corresponding raw materials, the intermediate B was prepared using the same method as in the preparation of compound A in Intermediate A.

MS m/z: 304.7[M+H]$^+$

Intermediate C

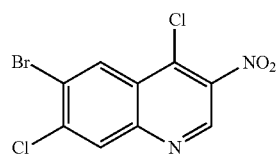

Synthetic Route

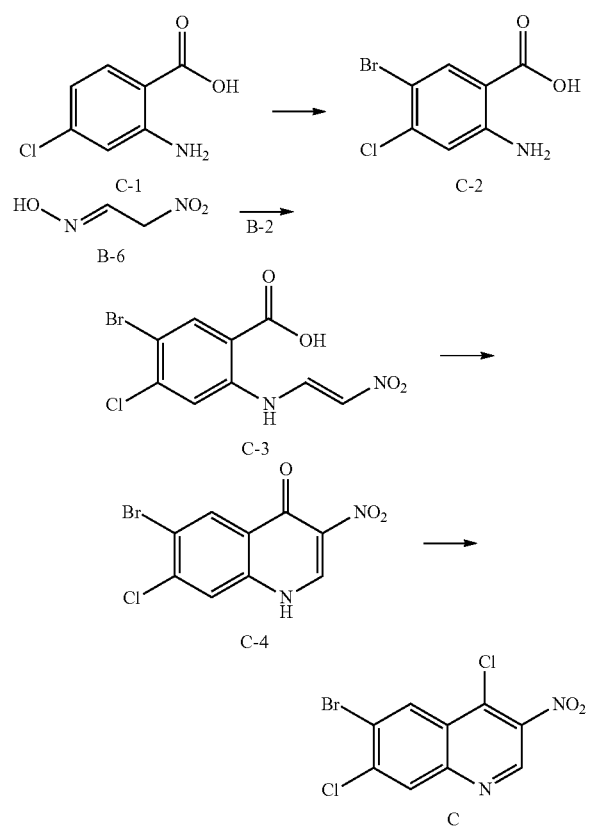

Step 1: Synthesis of Compound C-2

Except for using the corresponding raw materials, the compound C-2 was prepared using the same method as in the preparation of compound B-2 in Intermediate B.

MS m/z: 249.8[M+H]$^+$ $^1$H NMR (400 MHz, DMSO-d$_6$) δ 7.90 (br s, 1H), 7.01 (br s, 1H)

Step 2: Synthesis of Compound C-3

Except for using the corresponding raw materials, the compound C-3 was prepared using the same method as in the preparation of compound B-4 in Intermediate B.

MS m/z: 320.8[M+H]$^+$

¹H NMR (400 MHz, DMSO-d₆) δ 14.71-13.60 (m, 1H), 12.91 (br s, 1H), 8.26-8.01 (m, 3H), 6.80 (br s, 1H)

Step 3: Synthesis of Compound C-4

Except for using the corresponding raw materials, the compound C-4 was prepared using the same method as in the preparation of compound B-5 in Intermediate B.

MS m/z: 302.7[M+H]⁺

¹H NMR (400 MHz, DMSO-d₆) δ 9.29 (br s, 1H), 8.46 (s, 1H), 7.94 (s, 1H)

Step 4: Synthesis of Intermediate C

Except for using the corresponding raw materials, the intermediate C was prepared using the same method as in the preparation of compound A in Intermediate A.

MS m/z: 320.7[M+H]⁺

Example 1: Compound 1

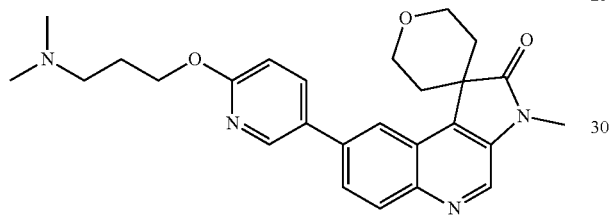

Synthetic Route

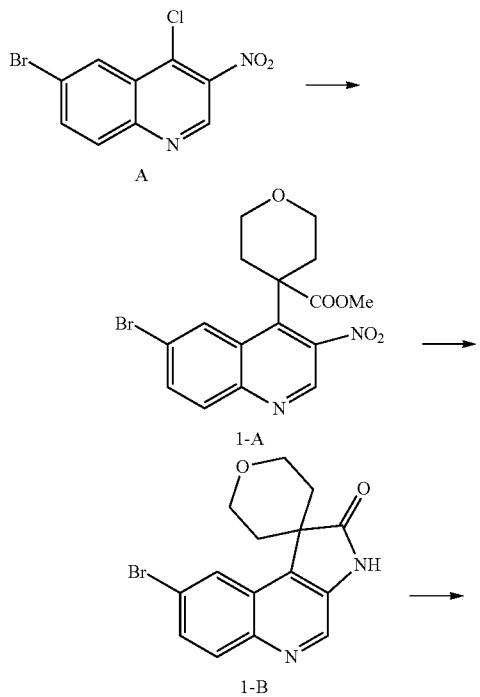

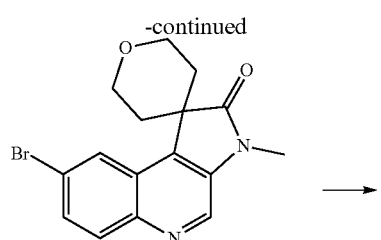

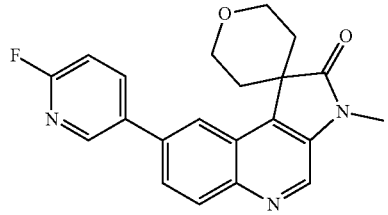

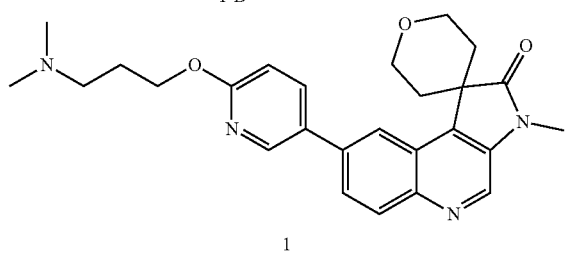

Step 1: Synthesis of Compound 1-A n-BuLi (2.5 M, 765.23 μL) was slowly added dropwise to a solution of DIPA (193.58 mg, 1.91 mmol, 270.37 μL) in THF (1 mL) at −60° C., and stirred for 0.5 h. Then methyl tetrahydropyran-4-carboxylate (300.88 mg, 2.09 mmol, 278.59 μL) was added dropwise at −60° C. and stirred for 1 h, and a solution of intermediate A (500 mg, 1.74 mmol) in THF (4 mL) was added and stirred at −60° C. for 2 h. After completion of the reaction, the reaction was quenched by adding 20 mL of saturated NH₄Cl solution at 0° C., and extracted with EtOAc (30 mL, 10 mL*3). The organic phase was combined, washed with saturated brine (50 mL), and dried over anhydrous sodium sulfate. After removing the desiccant by filtration, the solvent was removed under reduced pressure to obtain a crude product. The crude product was purified by column chromatography (0 to 10% THF/PE) to obtain compound 1-A.

MS m/z: 394.9[M+H]⁺

¹H NMR (400 MHz, CDCl₃) δ 8.75 (s, 1H), 8.52 (d, J=1.8 Hz, 1H), 8.05 (d, J=9.0 Hz, 1H), 7.88 (dd, J=2.0, 9.0 Hz, 1H), 4.00-3.89 (m, 4H), 3.69 (s, 3H), 2.52-2.46 (m, 2H), 2.43-2.31 (m, 2H)

Step 2: Synthesis of Compound 1-B

Zn (330.92 mg, 5.06 mmol) and NH₄Cl (270.70 mg, 5.06 mmol) were added to a solution of compound 1-A (200 mg, 506.07 μmol) in H₂O (10 mL) and THF (10 mL). The reaction solution was stirred at 70° C. for 0.5 h. After completion of the reaction, the reaction solution was filtered through celite. The filtrate was extracted with EtOAc (90 mL, 30 mL*3). The organic phase was combined, washed with saturated brine (50 mL), and dried over anhydrous sodium sulfate. After removing the desiccant by filtration, the solvent was removed under reduced pressure to obtain a crude product, and the crude product was purified by column chromatography (0 to 10% THF/DCM) to obtain compound 1-B.

MS m/z: 332.8[M+H]+

1H NMR (400 MHz, CDCl3) δ 8.74 (s, 1H), 8.23 (d, J=1.8 Hz, 1H), 8.01 (d, J=9.0 Hz, 1H), 7.69 (dd, J=2.0, 9.0 Hz, 1H), 4.48-4.40 (m, 2H), 4.01 (dd, J=5.1, 11.7 Hz, 2H), 2.68 (dt, J=5.1, 13.5 Hz, 2H), 1.75 (br d, J=14.3 Hz, 2H)

Step 3: Synthesis of Compound 1-C

MeI (1.350 g, 9.51 mmol, 592.11 μL), TBAB (9.68 mg, 30.01 μmol) and NaOH (24.01 mg, 600.28 μmol) were added to a mixed solution of compound 1-B (100 mg, 300.14 μmol) in DCM (5 mL) and H2O (5 mL), and stirred at 25° C. for 21 h. After completion of the reaction, the reaction system was added with 10 mL of water at room temperature to quench the reaction, and extracted with DCM (30 mL, 10 mL*3). The organic phase was combined, washed with saturated brine (50 mL), and dried over anhydrous sodium sulfate. After removing the desiccant by filtration, the solvent was removed under reduced pressure to obtain a crude product, and the crude product was purified by column chromatography (0 to 10% THF/DCM) to obtain compound 1-C.

MS m/z: 346.9[M+H]+

1H NMR (400 MHz, CDCl3) δ 8.71 (s, 1H), 8.24 (d, J=2.0 Hz, 1H), 8.01 (d, J=9.1 Hz, 1H), 7.68 (dd, J=2.1, 9.1 Hz, 1H), 4.48 (dt, J=2.1, 12.2 Hz, 2H), 4.00 (dd, J=5.1, 11.6 Hz, 2H), 3.38 (s, 3H), 2.67 (dt, J=5.3, 13.4 Hz, 2H), 1.66 (br d, J=14.3 Hz, 2H)

Step 4: Synthesis of Compound 1-D

Under nitrogen protection, 1,4-dioxane (3 mL) and H2O (3 mL) were added to a reaction system of compound 1-C (70 mg, 201.61 μmol), 2-fluoropyridine-5-boracic acid (42.61 mg, 302.41 μmol), Pd(PPh3)4 (23.30 mg, 20.16 μmol) and Na2CO3 (64.11 mg, 604.83 mol), and stirred at 80° C. for 3 h. After completion of the reaction, the reaction system was added with H2O (20 mL) and EtOAc (30 mL), and filtered through celite. The organic phase was collected, washed with saturated brine (50 mL), and dried over anhydrous sodium sulfate. After removing the desiccant by filtration, the solvent was removed under reduced pressure to obtain a crude product, and the crude product was purified by column chromatography (0 to 30% THF/DCM) to obtain compound 1-D.

MS m/z: 364.0[M+H]+

1H NMR (400 MHz, CDCl3) δ 8.75 (s, 1H), 8.56 (d, J=2.1 Hz, 1H), 8.26 (d, J=8.9 Hz, 1H), 8.18 (d, J=1.5 Hz, 1H), 8.11 (dt, J=2.5, 8.0 Hz, 1H), 7.79 (dd, J=1.8, 8.8 Hz, 1H), 7.12 (dd, J=3.0, 8.4 Hz, 1H), 4.50 (br t, J=11.3 Hz, 2H), 4.00 (dd, J=4.9, 11.7 Hz, 2H), 3.41 (s, 3H), 2.74 (dt, J=5.3, 13.4 Hz, 2H), 1.72 (br d, J=14.1 Hz, 2H)

Step 5: Synthesis of Compound 1

At 0° C. and under nitrogen protection, a solution of compound 3-dimethylamino-1-propanol (34.39 mg, 333.34 μmol, 38.99 μL) in DMF (2 mL) was added with NaH (26.67 mg, 666.68 μmol, 60% purity), and then a solution of compound 1-D (61.45 mg, 166.67 μmol) in DMF (2 mL) was added, and stirred at 27° C. for 2.5 h. At 0° C., the reaction system was added with 50 mL of water to quench the reaction, and extracted with DCM/i-prOH (5/1) (10 mL*3). The organic phase was combined, washed with saturated brine (100 mL), and dried over anhydrous sodium sulfate. After removing the desiccant by filtration, the solvent was removed under reduced pressure to obtain a crude product, and the crude product was subjected to column chromatography (0 to 10% MeOH/DCM (adding aqueous ammonia)) to obtain compound 1.

MS m/z: 447.2[M+H]+

1H NMR (400 MHz, CDCl3) δ 8.66 (s, 1H), 8.47 (d, J=2.5 Hz, 1H), 8.16 (d, J=8.9 Hz, 1H), 8.12 (d, J=1.5 Hz, 1H), 7.88 (dd, J=2.5, 8.6 Hz, 1H), 7.75 (dd, J=1.7, 8.8 Hz, 1H), 6.85 (d, J=8.5 Hz, 1H), 4.49-4.34 (m, 4H), 3.94 (dd, J=4.9, 11.6 Hz, 2H), 3.35 (s, 3H), 2.71 (dt, J=5.1, 13.4 Hz, 2H), 2.50-2.43 (m, 2H), 2.25 (s, 6H), 2.02-1.94 (m, 2H), 1.65 (br d, J=14.0 Hz, 2H)

Example 2: Compound 2

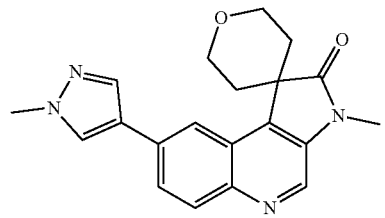

Synthetic Route

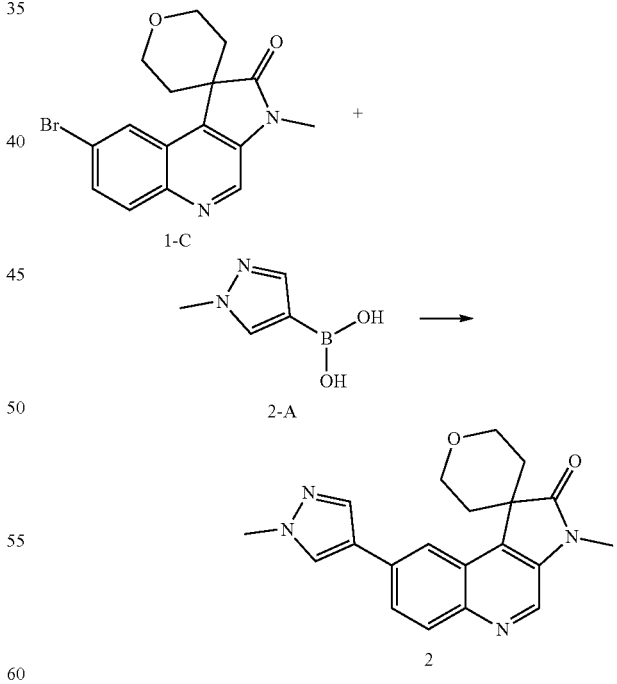

Step 1: Synthesis of Compound 2

Under nitrogen protection, 1,4-dioxane (3 mL) was added to a reaction system of compound 1-C (200 mg, 576.03 μmol), (1-methyl-1H-pyrazol)-4-boracic acid (179.78 mg, 864.04 μmol), [1,1'-bis(diphenylphosphino)ferrocene]palladium dichloride dichloromethane complex (47.04 mg, 57.60 μmol) and potassium acetate (169.59 mg, 1.73 mmol), and stirred at 80° C. for 18 h. After completion of the reaction, the solvent was removed under reduced pressure to obtain a crude product, and the crude product was purified by column chromatography (0 to 10% THF/DCM) to obtain compound 2.

MS m/z: 349.1[M+H]⁺

¹H NMR (400 MHz, CDCl₃) δ 8.64 (s, 1H), 8.13 (d, J=8.9 Hz, 1H), 8.08 (d, J=1.8 Hz, 1H), 7.91 (s, 1H), 7.83 (s, 1H), 7.75 (dd, J=1.8, 8.8 Hz, 1H), 4.51 (dt, J=2.1, 12.2 Hz, 2H), 4.04-3.98 (m, 5H), 3.38 (s, 3H), 2.81-2.70 (m, 2H), 1.69 (br d, J=14.3 Hz, 2H)

Example 3: Compound 3

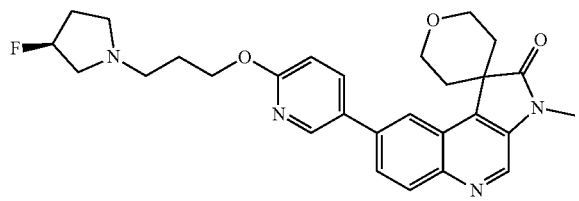 [SMILES: CN1C(=O)C2(CCOCC2)c2c1cnc1ccc(-c3ccc(OCCCN4CC[C@H](F)C4)nc3)cc21]

Synthetic Route

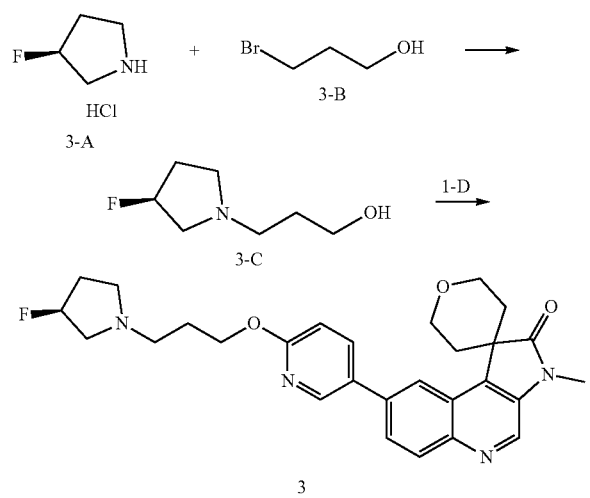

Step 1: Synthesis of Compound 3-C

Acetonitrile (10 mL) was added to a flask of 3-A (200 mg, 1.59 mmol), 3-B (225.80 mg, 1.62 mmol, 146.62 μL) and K₂CO₃ (660.37 mg, 4.78 mmol), and stirred at 80° C. for 12 h. The system was filtered by adding methanol (50 mL), and then the solvent was removed from the filtrate under reduced pressure. The residual solid was added to dichloromethane (50 mL), filtered, and concentrated under reduced pressure to obtain 3-C.

MS m/z: 147.9[M+H]⁺

¹H NMR (400 MHz, CD₃OD) δ 5.28-5.07 (m, 1H), 3.72-3.57 (m, 2H), 3.04-2.87 (m, 2H), 2.73-2.56 (m, 3H), 2.47-2.39 (m, 1H), 2.28-1.90 (m, 2H), 1.82-1.69 (m, 2H)

Step 2: Synthesis of Compound 3

Except for using the corresponding raw materials, the compound 3 was prepared using the same method as in the preparation of compound 1 in Example 1.

MS m/z: 491.2[M+H]⁺ ee: 100%, RT=1.955 min (column type: Chiralpak AD-3 50×3 mm I.D., 3 m; mobile phase: A: CO₂, B: ethanol (0.05% diethylamine); gradient: the proportion of B in mobile phase rises from 5% to 40% within 2.5 minutes and keeps at 40% for 0.35 minutes, and then the proportion of mobile phase is reduced from 40% to 5% within 0.15 minutes; flow rate: 2.5 mL/min, column temperature: 40° C.)

¹H NMR (400 MHz, CDCl₃) δ 8.71 (s, 1H), 8.51 (d, J=2.5 Hz, 1H), 8.21 (d, J=8.8 Hz, 1H), 8.16 (d, J=1.8 Hz, 1H), 7.93 (dd, J=2.5, 8.5 Hz, 1H), 7.80 (dd, J=1.9, 8.9 Hz, 1H), 6.89 (d, J=8.5 Hz, 1H), 5.28-5.09 (m, 1H), 4.53-4.42 (m, 4H), 3.99 (dd, J=4.8, 11.5 Hz, 2H), 3.40 (s, 3H), 2.98-2.85 (m, 2H), 2.84-2.77 (m, 1H), 2.75 (br d, J=5.0 Hz, 1H), 2.74-2.66 (m, 3H), 2.52-2.44 (m, 1H), 2.25-1.98 (m, 4H), 1.70 (br d, J=14.3 Hz, 2H)

Example 4: Compound 4

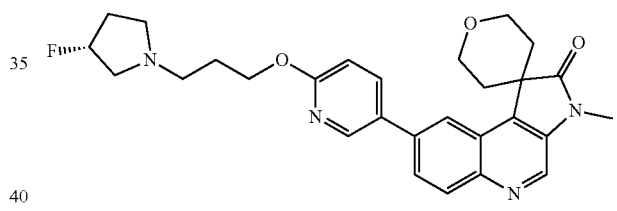

Synthetic Route

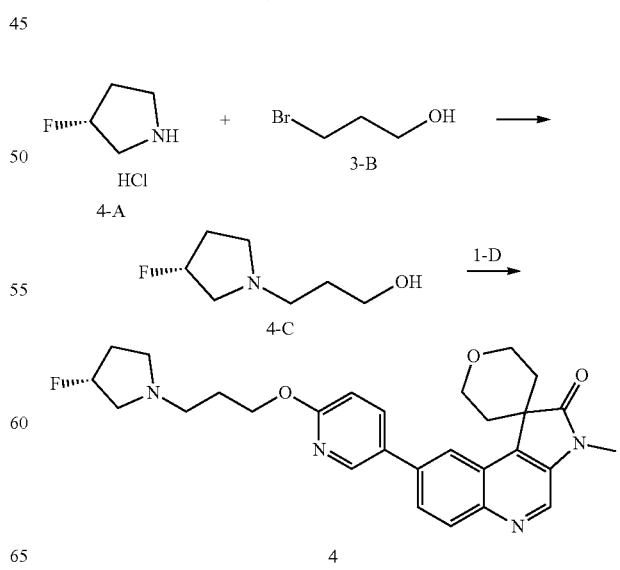

Step 1: Synthesis of Compound 4-C

Except for using the corresponding raw materials, the compound 4-C was prepared using the same method as in the preparation of compound 3-C in Example 3.

MS m/z: 147.9[M+H]+

¹H NMR (400 MHz, CD₃OD) δ 5.30-5.08 (m, 1H), 3.64 (t, J=6.28 Hz, 2H), 3.04-2.89 (m, 2H), 2.62 (ddd, J=9.66, 5.52, 2.38 Hz, 3H), 2.42 (td, J=8.16, 7.03 Hz, 1H), 2.29-1.94 (m, 2H), 1.83-1.70 (m, 2H)

Step 2: Synthesis of Compound 4

Except for using the corresponding raw materials, the compound 4 was prepared using the same method as in the preparation of compound 1 in Example 1.

MS m/z: 491.3[M+H]+ ee: 100%, retention time=1.952 min (column type: Chiralpak AD-3 50×3 mm I.D., 3 m; mobile phase: A: CO₂, B: ethanol (0.05% diethylamine); gradient: 5%-40% B, 2.5 minutes 40%-40% B, 0.35 minutes; 40%-5% B, 0.15 minutes; flow rate: 2.5 mL/min; column temperature: 40° C.)

¹H NMR (400 MHz, CDCl₃) δ 8.71 (s, 1H), 8.51 (d, J=2.3 Hz, 1H), 8.21 (d, J=8.8 Hz, 1H), 8.16 (s, 1H), 7.93 (dd, J=2.4, 8.7 Hz, 1H), 7.83-7.77 (m, 1H), 6.89 (d, J=8.8 Hz, 1H), 5.28-5.08 (m, 1H), 4.54-4.42 (m, 4H), 3.99 (br dd, J=4.6, 11.7 Hz, 2H), 3.40 (s, 3H), 2.98-2.85 (m, 2H), 2.84-2.66 (m, 5H), 2.53-2.43 (m, 1H), 2.26-1.97 (m, 4H), 1.71 (br s, 2H)

Example 5: Compound 5

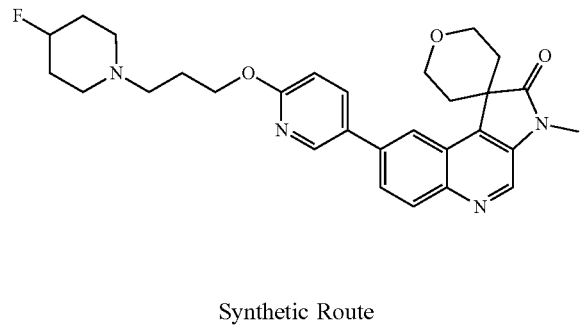

Synthetic Route

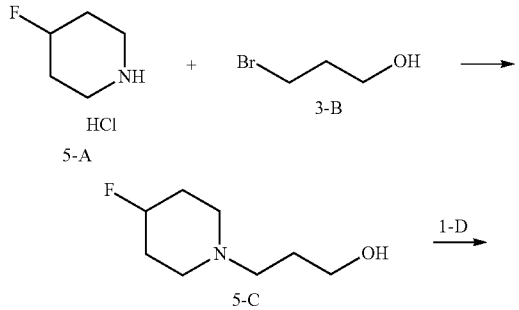

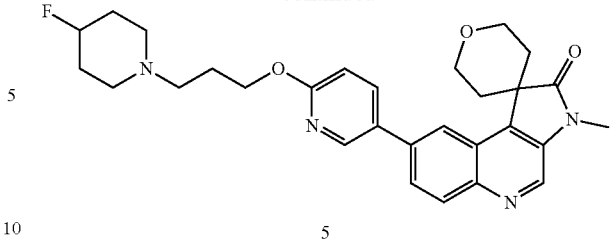

Step 1: Synthesis of Compound 5-C

Except for using the corresponding raw materials, the compound 5-C was prepared using the same method as in the preparation of compound 3-C in Example 3.

¹H NMR (400 MHz, CDCl₃) δ 4.84-4.56 (m, 1H), 3.83-3.70 (m, 3H), 3.52 (t, J=6.5 Hz, 1H), 2.64-2.57 (m, 3H), 2.10-04 (m, 1H), 1.93-1.87 (m, 2H), 1.87-1.81 (m, 2H), 1.74-1.68 (m, 2H)

Step 2: Synthesis of Compound 5

Except for using the corresponding raw materials, the compound 5 was prepared using the same method as in the preparation of compound 1 in Example 1.

MS m/z: 505.3[M+H]+

¹H NMR (400 MHz, CDCl₃) δ 8.71 (s, 1H), 8.51 (d, J=2.3 Hz, 1H), 8.22 (d, J=9.0 Hz, 1H), 8.16 (d, J=1.5 Hz, 1H), 7.93 (dd, J=2.5, 8.8 Hz, 1H), 7.80 (dd, J=1.8, 8.8 Hz, 1H), 6.89 (d, J=8.5 Hz, 1H), 4.80-4.59 (m, 1H), 4.49 (br t, J=11.4 Hz, 2H), 4.43 (t, J=6.5 Hz, 2H), 3.99 (dd, J=4.9, 11.7 Hz, 2H), 3.40 (s, 3H), 2.76 (dt, J=5.1, 13.5 Hz, 2H), 2.63 (br s, 2H), 2.56 (br t, J=7.4 Hz, 2H), 2.42 (br s, 2H), 2.08-1.99 (m, 2H), 1.88 (br d, J=4.5 Hz, 4H), 1.70 (br d, J=14.1 Hz, 2H)

Example 6: Compound 6

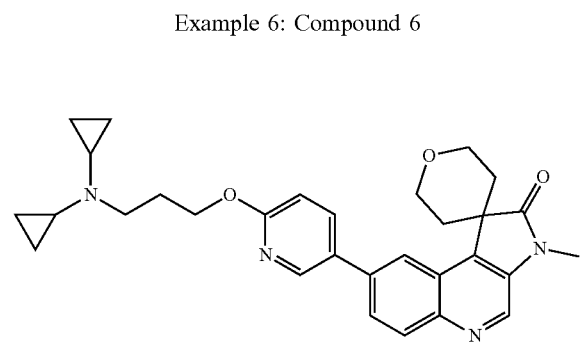

Synthetic Route

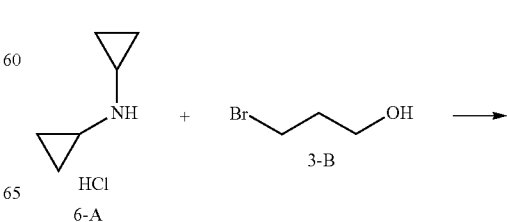

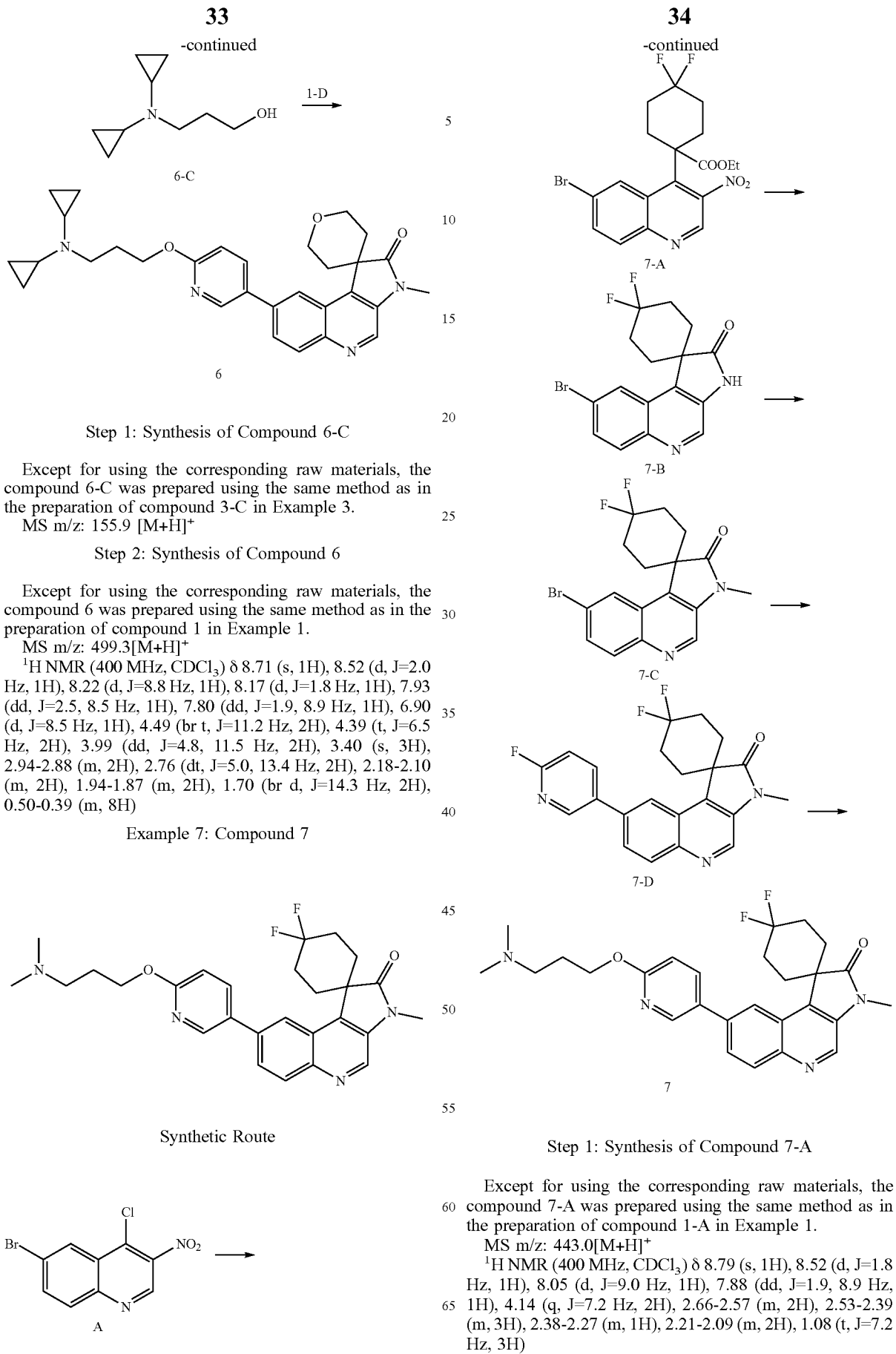

Step 1: Synthesis of Compound 6-C

Except for using the corresponding raw materials, the compound 6-C was prepared using the same method as in the preparation of compound 3-C in Example 3.
MS m/z: 155.9 [M+H]$^+$ Step 2: Synthesis of Compound 6

Except for using the corresponding raw materials, the compound 6 was prepared using the same method as in the preparation of compound 1 in Example 1.
MS m/z: 499.3[M+H]$^+$
$^1$H NMR (400 MHz, CDCl$_3$) δ 8.71 (s, 1H), 8.52 (d, J=2.0 Hz, 1H), 8.22 (d, J=8.8 Hz, 1H), 8.17 (d, J=1.8 Hz, 1H), 7.93 (dd, J=2.5, 8.5 Hz, 1H), 7.80 (dd, J=1.9, 8.9 Hz, 1H), 6.90 (d, J=8.5 Hz, 1H), 4.49 (br t, J=11.2 Hz, 2H), 4.39 (t, J=6.5 Hz, 2H), 3.99 (dd, J=4.8, 11.5 Hz, 2H), 3.40 (s, 3H), 2.94-2.88 (m, 2H), 2.76 (dt, J=5.0, 13.4 Hz, 2H), 2.18-2.10 (m, 2H), 1.94-1.87 (m, 2H), 1.70 (br d, J=14.3 Hz, 2H), 0.50-0.39 (m, 8H)

Example 7: Compound 7

Synthetic Route

Step 1: Synthesis of Compound 7-A

Except for using the corresponding raw materials, the compound 7-A was prepared using the same method as in the preparation of compound 1-A in Example 1.
MS m/z: 443.0[M+H]$^+$
$^1$H NMR (400 MHz, CDCl$_3$) δ 8.79 (s, 1H), 8.52 (d, J=1.8 Hz, 1H), 8.05 (d, J=9.0 Hz, 1H), 7.88 (dd, J=1.9, 8.9 Hz, 1H), 4.14 (q, J=7.2 Hz, 2H), 2.66-2.57 (m, 2H), 2.53-2.39 (m, 3H), 2.38-2.27 (m, 1H), 2.21-2.09 (m, 2H), 1.08 (t, J=7.2 Hz, 3H)

Step 2: Synthesis of Compound 7-B

Except for using the corresponding raw materials, the compound 7-B was prepared using the same method as in the preparation of compound 1-B in Example 1.

MS m/z: 366.8[M+H]$^+$ $^1$H NMR (400 MHz, CDCl$_3$) δ 8.78 (s, 1H), 8.05-8.02 (m, 2H), 7.70 (dd, J=2.0, 9.0 Hz, 1H), 2.92-2.80 (m, 1H), 2.78-2.65 (m, 3H), 2.17 (br s, 2H), 1.94 (br d, J=12.3 Hz, 2H)

Step 3: Synthesis of Compound 7-C

Except for using the corresponding raw materials, the compound 7-C was prepared using the same method as in the preparation of compound 1-C in Example 1.

$^1$H NMR (400 MHz, CDCl$_3$) δ 8.71 (s, 1H), 8.04 (d, J=1.8 Hz, 1H), 8.01 (d, J=9.0 Hz, 1H), 7.68 (dd, J=1.8, 9.0 Hz, 1H), 3.38 (s, 3H), 2.94-2.75 (m, 2H), 2.74-2.63 (m, 2H), 2.15 (br s, 2H), 1.89-1.79 (m, 2H)

Step 4: Synthesis of Compound 7-D

Except for using the corresponding raw materials, the compound 7-D was prepared using the same method as in the preparation of compound 1-D in Example 1.

MS m/z: 398.0[M+H]$^+$ $^1$H NMR (400 MHz, CDCl$_3$) δ 8.75 (s, 1H), 8.56 (d, J=2.5 Hz, 1H), 8.26 (d, J=8.8 Hz, 1H), 8.10 (dt, J=2.5, 8.0 Hz, 1H), 8.06 (d, J=1.8 Hz, 1H), 7.82 (dd, J=2.0, 8.8 Hz, 1H), 7.11 (dd, J=2.9, 8.4 Hz, 1H), 3.41 (s, 3H), 2.95-2.73 (m, 4H), 2.15 (br d, J=5.3 Hz, 2H), 1.90 (br d, J=11.5 Hz, 2H)

Step 5: Synthesis of Compound 7

Except for using the corresponding raw materials, the compound 7 was prepared using the same method as in the preparation of compound 1 in Example 1.

MS m/z: 481.2[M+H]$^+$ $^1$H NMR (400 MHz, CDCl$_3$) δ 8.70 (s, 1H), 8.50 (d, J=2.3 Hz, 1H), 8.21 (d, J=9.0 Hz, 1H), 8.02 (d, J=1.8 Hz, 1H), 7.91 (dd, J=2.6, 8.7 Hz, 1H), 7.81 (dd, J=1.9, 8.9 Hz, 1H), 6.88 (d, J=8.5 Hz, 1H), 4.43 (t, J=6.4 Hz, 2H), 3.40 (s, 3H), 2.96-2.74 (m, 4H), 2.58 (br t, J=7.5 Hz, 2H), 2.35 (s, 6H), 2.20-2.11 (m, 2H), 2.10-2.01 (m, 2H), 1.88 (br d, J=9.8 Hz, 2H)

Example 8: Compound 8

Synthetic Route

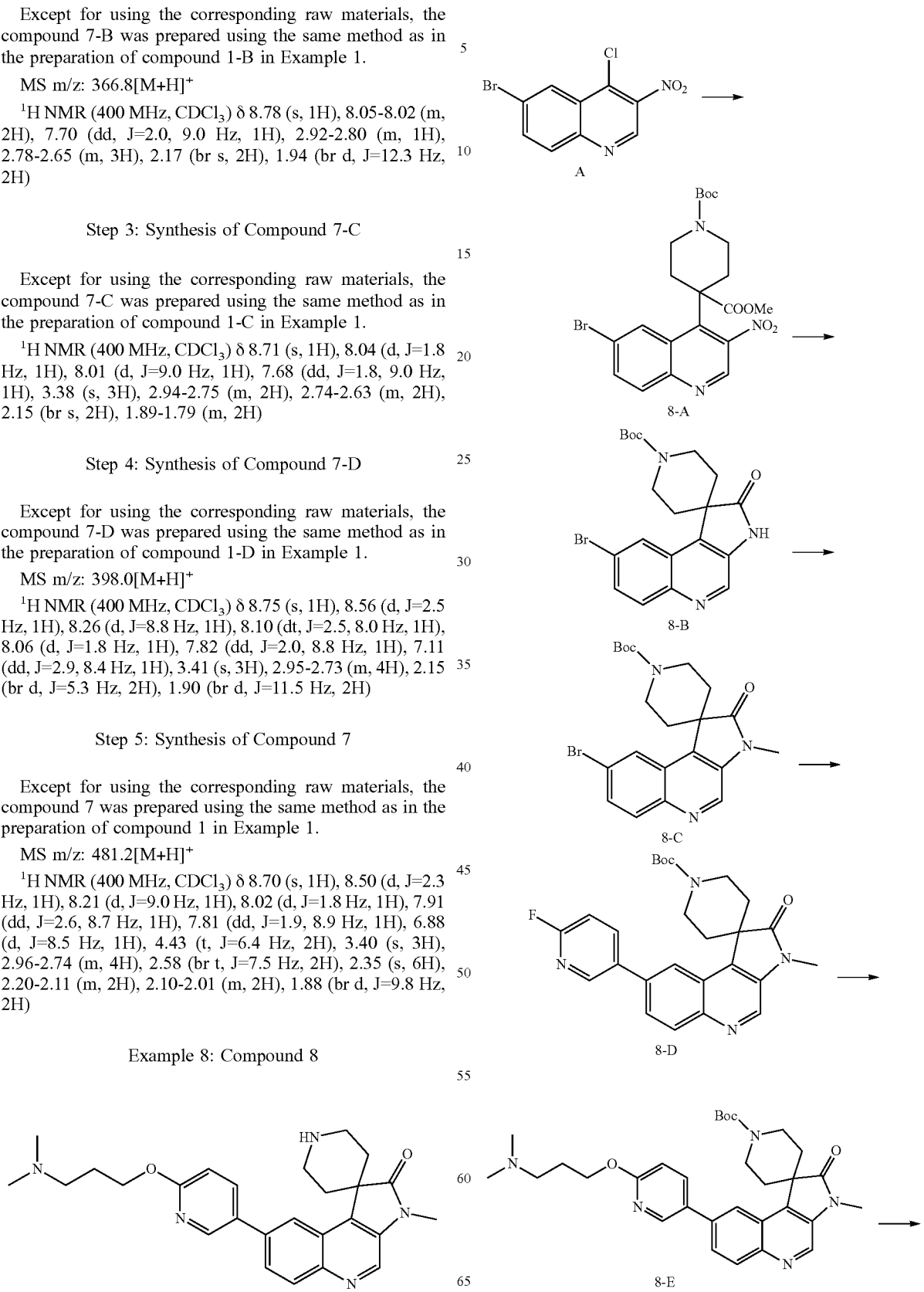

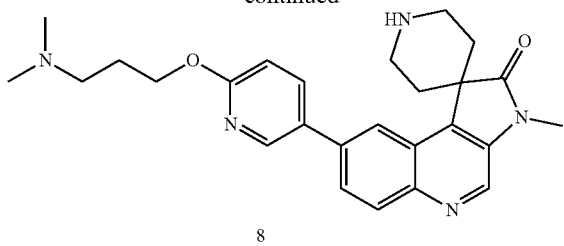

8

Step 1: Synthesis of Compound 8-A

Except for using the corresponding raw materials, the compound 8-A was prepared using the same method as in the preparation of compound 1-A in Example 1.

$^1$H NMR (400 MHz, CDCl$_3$) δ 8.74 (s, 1H), 8.46 (d, J=1.8 Hz, 1H), 8.05 (d, J=8.8 Hz, 1H), 7.88 (dd, J=2.0, 9.0 Hz, 1H), 4.02 (br s, 2H), 3.66 (s, 3H), 3.36-3.22 (m, 2H), 2.53 (br s, 2H), 2.28-2.18 (m, 2H), 1.48 (s, 9H)

Step 2: Synthesis of Compound 8-B

Except for using the corresponding raw materials, the compound 8-B was prepared using the same method as in the preparation of compound 1-B in Example 1.

MS: m z: 432.0[M+H]$^+$ $^1$H NMR (400 MHz, CDCl$_3$) δ 8.73 (s, 1H), 8.07 (s, 1H), 8.02-7.98 (m, 2H), 7.68 (dd, J=2.0, 9.0 Hz, 1H), 4.30-4.01 (m, 2H), 3.78-3.72 (m, 2H), 2.49 (br s, 2H), 1.78 (br d, J=13.8 Hz, 2H), 1.62 (s, 9H)

Step 3: Synthesis of Compound 8-C

Except for using the corresponding raw materials, the compound 8-C was prepared using the same method as in the preparation of compound 1-C in Example 1.

MS m/z: 446.0[M+H]$^+$ $^1$H NMR (400 MHz, CDCl$_3$) δ 8.71 (s, 1H), 8.03-7.99 (m, 2H), 7.67 (dd, J=2.1, 9.2 Hz, 1H), 4.30-4.02 (m, 2H), 3.75 (br d, J=6.8 Hz, 2H), 3.38 (s, 3H), 2.48 (br s, 2H), 1.69 (br d, J=13.1 Hz, 2H), 1.57 (s, 9H)

Step 4: Synthesis of Compound 8-D

Except for using the corresponding raw materials, the compound 8-D was prepared using the same method as in the preparation of compound 1-D in Example 1.

MS m/z: 463.2[M+H]$^+$ $^1$H NMR (400 MHz, CDCl$_3$) δ 8.75 (s, 1H), 8.51 (d, J=2.5 Hz, 1H), 8.25 (d, J=8.8 Hz, 1H), 8.06 (dt, J=2.6, 8.0 Hz, 1H), 7.97 (d, J=1.8 Hz, 1H), 7.78 (dd, J=1.8, 8.8 Hz, 1H), 7.06 (dd, J=3.0, 8.5 Hz, 1H), 4.29-4.02 (m, 2H), 3.90-3.72 (m, 2H), 3.41 (s, 3H), 2.55 (br s, 2H), 1.76 (br d, J=14.1 Hz, 2H), 1.50 (s, 9H)

Step 5: Synthesis of Compound 8-E

Except for using the corresponding raw materials, the compound 8-E was prepared using the same method as in the preparation of compound 1 in Example 1.

$^1$H NMR (400 MHz, CDCl$_3$) δ 8.70 (s, 1H), 8.45 (d, J=2.3 Hz, 1H), 8.20 (d, J=8.8 Hz, 1H), 7.96 (d, J=1.5 Hz, 1H), 7.86 (dd, J=2.5, 8.5 Hz, 1H), 7.78 (dd, J=1.9, 8.9 Hz, 1H), 6.84 (d, J=8.5 Hz, 1H), 4.41 (t, J=6.5 Hz, 2H), 3.81-3.77 (m, 2H), 3.39 (s, 3H), 2.57-2.52 (m, 2H), 2.50-2.45 (m, 2H), 2.28 (s, 6H), 2.03-1.96 (m, 2H), 1.74 (br d, J=13.6 Hz, 2H), 1.71-1.65 (m, 2H), 1.51 (s, 9H)

Step 6: Synthesis of Compound 8

Trifluoroacetic acid (1 mL) was added to 8-E (100 mg, 183.26 μmol). The reaction solution was stirred at 20° C. for 1 h. Trifluoroacetic acid was removed under reduced pressure to obtain a crude, which was separated by preparative chromatography (acid, mobile phase: acetonitrile-water). Then ammonia water was added to adjust pH=8. The crude product was obtained by concentration under reduced pressure, and purified by column chromatography (0 to 10% MeOH/DCM) to obtain compound 8.

MS m/z: 446.2[M+H]$^+$ $^1$H NMR (400 MHz, CDCl$_3$) δ 8.69 (s, 1H), 8.51 (d, J=2.5 Hz, 1H), 8.22 (d, J=1.5 Hz, 1H), 8.20 (d, J=8.9 Hz, 1H), 7.93 (dd, J=2.6, 8.6 Hz, 1H), 7.77 (dd, J=1.7, 8.8 Hz, 1H), 6.88 (d, J=8.6 Hz, 1H), 4.42 (t, J=6.5 Hz, 2H), 3.74-3.65 (m, 2H), 3.38 (s, 3H), 3.04 (br dd, J=3.4, 12.3 Hz, 2H), 2.59 (dt, J=4.6, 13.3 Hz, 2H), 2.50-2.45 (m, 2H), 2.27 (s, 6H), 2.04-1.96 (m, 2H), 1.75 (br d, J=14.0 Hz, 2H)

Example 9: Compound 9

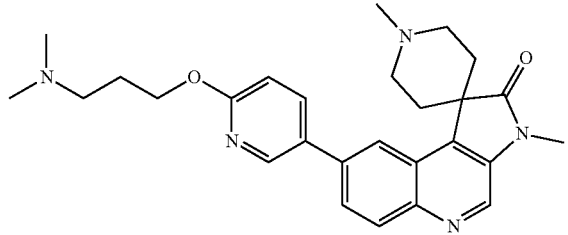

Synthetic Route

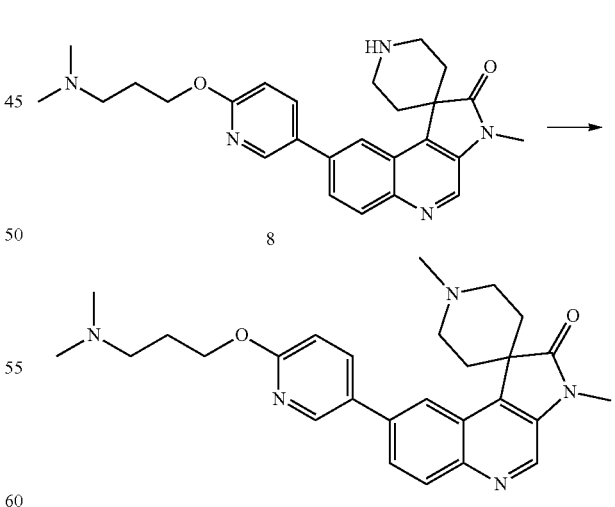

Step 1: Synthesis of Compound 9

Aqueous formaldehyde solution (127.51 mg, 1.57 mmol, 116.98 μL, 37% purity) was added to a solution of compound 8 (70 mg, 157.11 µmol) in formic acid (3 mL), and the reaction solution was stirred at 60° C. for 23 h. After completion of the reaction, a crude product was obtained by concentration under reduced pressure. 20 ml of ammonia water was added, and a crude product was obtained by concentration under reduced pressure. The crude product was purified by column chromatography (0 to 6% MeOH/DCM) and then purified by preparative chromatography (neutral, mobile phase: acetonitrile-water) to obtain compound 9.

MS m/z: 460.3[M+H]+

$^1$H NMR (400 MHz, CDCl$_3$) δ 8.67 (s, 1H), 8.52 (br s, 1H), 8.26 (br s, 1H), 8.19 (br d, J=8.8 Hz, 1H), 7.96 (br d, J=7.8 Hz, 1H), 7.76 (br d, J=8.5 Hz, 1H), 6.87 (br d, J=8.5 Hz, 1H), 4.41 (br t, J=6.1 Hz, 2H), 3.37 (s, 3H), 3.10-2.98 (m, 2H), 2.79 (br d, J=8.8 Hz, 4H), 2.51-2.45 (m, 2H), 2.27 (s, 9H), 2.05-1.94 (m, 2H), 1.76 (br d, J=12.8 Hz, 2H)

Example 10: Compound 10

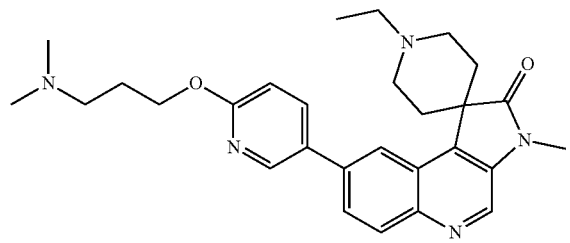

Synthetic Route

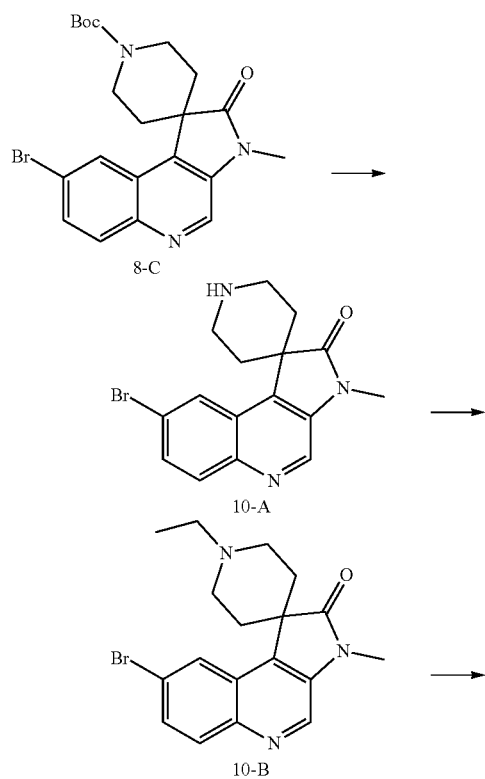

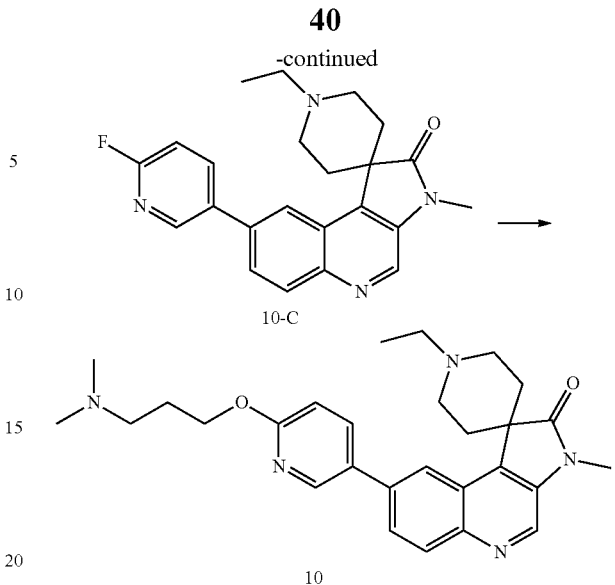

Step 1: Synthesis of Compound 10-A

Trifluoroacetic acid (3 mL) was added to compound 8-C (900 mg, 2.02 mmol), and the reaction solution was stirred at 20° C. for 0.5 h. After completion of the reaction, a crude product was obtained by concentration under reduced pressure. Ammonia water was added to adjust pH=9. Extraction with dichloromethane (90 mL, 30 mL*3) was performed, and the organic phase was concentrated under reduced pressure to obtain a crude product 10-A, which was directly used in the next step.

MS m/z: 346.1[M+H]+

$^1$H NMR (400 MHz, CDCl$_3$) δ 8.72 (s, 1H), 8.41 (d, J=2.0 Hz, 1H), 7.99 (d, J=9.0 Hz, 1H), 7.69 (dd, J=2.0, 9.0 Hz, 1H), 3.97-3.88 (m, 2H), 3.39 (s, 3H), 3.35 (br d, J=3.0 Hz, 2H), 2.94-2.86 (m, 2H), 1.84 (br d, J=14.6 Hz, 2H)

Step 2: Synthesis of Compound 10-B

At 20° C. and under nitrogen protection, K$_2$CO$_3$ (1.20 g, 8.67 mmol) was added to a solution of compound 10-A (1 g, 2.89 mmol) and ethyl bromide (629.82 mg, 5.78 mmol, 431.38 µL) in acetonitrile (20 mL). The reaction solution was stirred at 60° C. for 1 h. The reaction was quenched by adding water (5 mL) at 20° C., then diluted with water (20 mL), extracted with EtOAc (90 mL, 30 mL*3). The organic phase was combined, washed with saturated sodium chloride (90 mL, 30 mL*3), dried over anhydrous sodium sulfate, filtered, and concentrated. The crude product was subjected to column chromatography (0 to 5% MeOH/DCM) to obtain compound 10-B.

MS m/z: 373.9[M+H]+

$^1$H NMR (400 MHz, DMSO-d$_6$) δ 8.94 (s, 1H), 8.15 (d, J=1.8 Hz, 1H), 8.03 (d, J=9.0 Hz, 1H), 7.76 (dd, J=2.3, 9.0 Hz, 1H), 3.30 (s, 3H), 2.92-2.75 (m, 4H), 2.56-2.53 (m, 1H), 2.48-2.39 (m, 3H), 1.80-1.64 (m, 2H), 1.14-1.08 (m, 3H)

Step 3: Synthesis of Compound 10-C

Under nitrogen protection, an aqueous solution of compound 10-B (400 mg, 1.07 mmol), 2-fluoropyridine-5-boracic acid (301.19 mg, 2.14 mmol), Na$_2$CO$_3$ (226.55 mg, 2.14 mmol) and Pd(PPh$_3$)$_4$ (123.50 mg, 106.87 µmol) in dioxane (18 mL) and H$_2$O (2 mL) was stirred at 100° C. for 4 h. The reaction solvent was removed by concentration, and the crude product was subjected to column chromatography (0 to 5% MeOH/DCM) to obtain compound 10-C.

MS m/z: 391.1[M+H]⁺

Step 8: Synthesis of Compound 10

At 20° C. and under nitrogen protection, compound 10-C (200 mg, 512.23 μmol) was added to a solution of 3-dimethylamino-1-propanol (105.69 mg, 1.02 mmol, 119.82 μL) and NaH (81.96 mg, 2.05 mmol, 60% purity) in DMF (10 mL), and the reaction solution was stirred for 2 h at 70° C. The reaction solution was quenched with water (2 mL) at 20° C., diluted by adding water (10 mL), and extracted with EtOAc (10 mL*3). The organic phase was combined, washed with saturated sodium chloride (10 mL*3), dried over anhydrous sodium sulfate, filtered, and concentrated, and the crude product was subjected to column chromatography (0 to 5% MeOH/DCM) to obtain compound 10.

MS m/z: 474.2[M+H]⁺

¹H NMR (400 MHz, CDCl₃) δ 8.67 (s, 1H), 8.51 (d, J=2.3 Hz, 1H), 8.26-8.23 (m, 1H), 8.19 (d, J=9.0 Hz, 1H), 7.98-7.89 (m, 1H), 7.80-7.71 (m, 1H), 6.88 (d, J=8.8 Hz, 1H), 4.42 (t, J=6.5 Hz, 2H), 3.37 (s, 3H), 3.03 (br s, 2H), 2.87 (br d, J=11.5 Hz, 2H), 2.76 (br s, 2H), 2.62 (q, J=7.1 Hz, 2H), 2.47 (s, 2H), 2.27 (s, 6H), 2.04-1.96 (m, 2H), 1.78 (br d, J=13.8 Hz, 2H), 1.17 (t, J=7.3 Hz, 3H)

Example 11: Compound 11

Step 1: Synthesis of Compound 11-C

Except for using the corresponding raw materials, the compound 11-C was prepared using the same method as in the preparation of compound 3-C in Example 3.

¹H NMR (400 MHz, CDCl₃) δ 5.96-5.45 (m, 1H), 3.78-3.70 (m, 2H), 2.51 (t, J=5.6 Hz, 2H), 2.47-2.05 (m, 4H), 1.65 (quin, J=5.5 Hz, 2H), 1.52 (quin, J=5.5 Hz, 4H), 1.39 (br s, 2H)

Step 2: Synthesis of Compound 11

Except for using the corresponding raw materials, the compound 11 was prepared using the same method as in the preparation of compound 10 in Example 10.

MS m/z: 514.3[M+H]⁺

¹H NMR (400 MHz, CDCl₃) δ 8.67 (s, 1H), 8.53 (d, J=2.5 Hz, 1H), 8.30 (d, J=1.3 Hz, 1H), 8.19 (d, J=8.8 Hz, 1H), 7.97 (dd, J=2.5, 8.8 Hz, 1H), 7.77 (dd, J=1.8, 8.8 Hz, 1H), 6.87 (d, J=8.5 Hz, 1H), 4.40 (t, J=6.5 Hz, 2H), 3.37 (s, 3H), 3.11-2.98 (m, 2H), 2.92-2.84 (m, 2H), 2.78 (br s, 2H), 2.62 (q, J=7.1 Hz, 2H), 2.54-2.33 (m, 8H), 2.08-1.95 (m, 2H), 1.77 (br d, J=13.8 Hz, 2H), 1.64-1.60 (m, 2H), 1.44 (br d, J=4.8 Hz, 2H), 1.17 (t, J=7.2 Hz, 3H)

Example 12: Compound 12

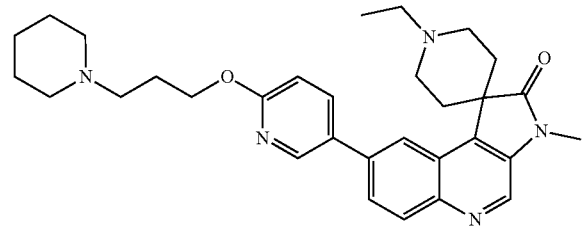 [SMILES: CCN1CCC2(CC1)C(=O)N(C)c1cnc3ccc(-c4ccc(OCCCN5CCCCC5)nc4)cc3c12]

Synthetic Route

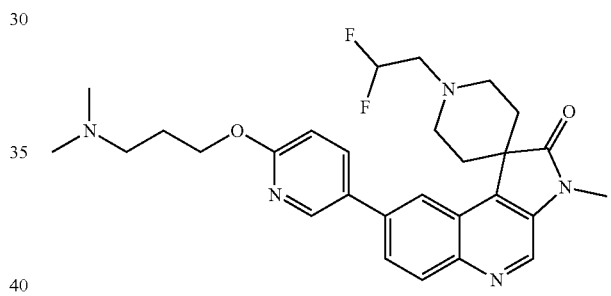

Synthetic Route

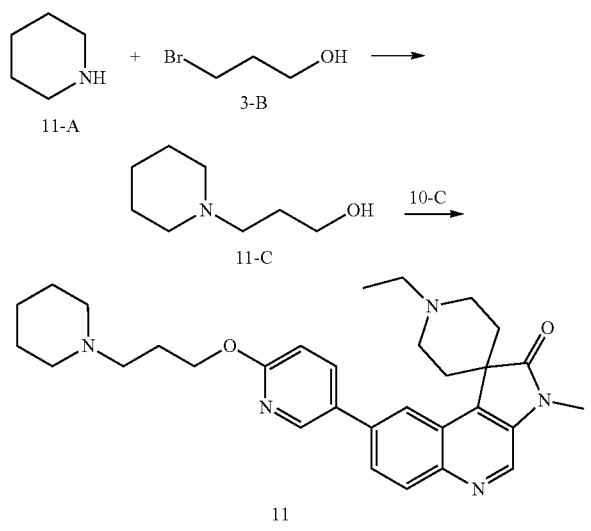

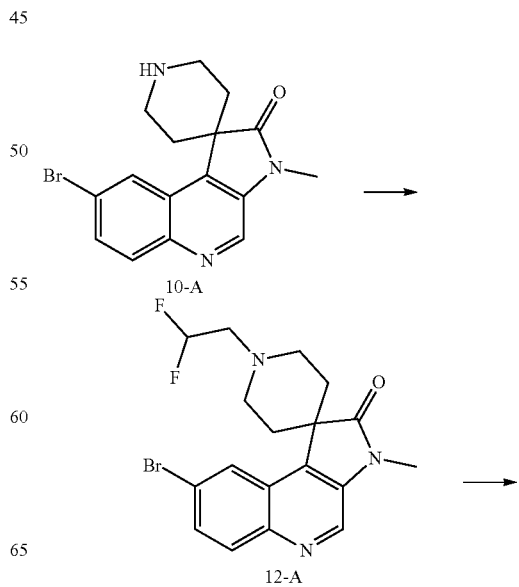

43

-continued

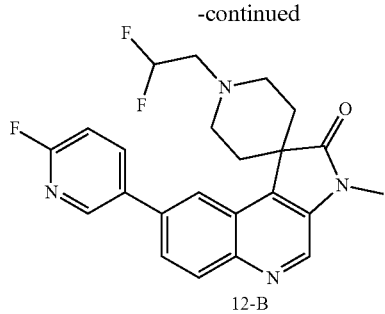

12-B

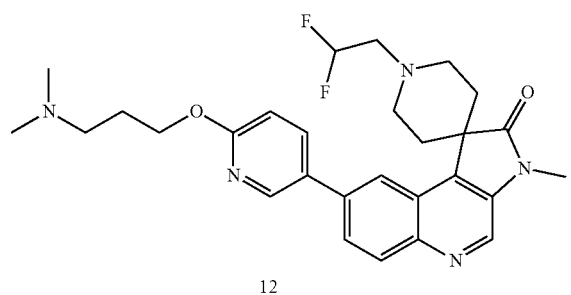

12

Step 1: Synthesis of Compound 12-A

Except for using the corresponding raw materials, the compound 12-A was prepared using the same method as in the preparation of compound 10-B in Example 10.

MS m/z: 410.4 [M+H]+

1H NMR (400 MHz, CDCl3) δ 8.69 (s, 1H), 8.25 (d, J=1.8 Hz, 1H), 8.00 (d, J=9.0 Hz, 1H), 7.67 (dd, J=2.0, 9.0 Hz, 1H), 6.21-5.85 (m, 1H), 3.36 (s, 3H), 3.33-3.25 (m, 2H), 3.00-2.87 (m, 4H), 2.65 (dt, J=4.6, 13.4 Hz, 2H), 1.73 (br d, J=14.6 Hz, 2H)

Step 2: Synthesis of Compound 12-B

Except for using the corresponding raw materials, the compound 12-B was prepared using the same method as in the preparation of compound 10-C in Example 10.

MS m/z: 427.2[M+H]+

Step 3: Synthesis of Compound 12

Except for using the corresponding raw materials, the compound 12 was prepared using the same method as in the preparation of compound 10 in Example 10.

MS m/z: 510.4 [M+H]+

¹H NMR (400 MHz, CDCl3) δ 8.69 (s, 1H), 8.53 (d, J=2.3 Hz, 1H), 8.24-8.16 (m, 2H), 7.93 (dd, J=2.5, 8.5 Hz, 1H), 7.78 (dd, J=2.0, 8.8 Hz, 1H), 6.90 (d, J=8.5 Hz, 1H), 6.20-5.81 (m, 1H), 4.43 (t, J=6.5 Hz, 2H), 3.38 (s, 3H), 3.31 (br t, J=11.0 Hz, 2H), 3.00-2.93 (m, 1H), 2.92-2.81 (m, 3H), 2.75 (dt, J=4.8, 13.3 Hz, 2H), 2.52-2.46 (m, 2H), 2.29 (s, 6H), 2.07-1.96 (m, 2H), 1.77 (br d, J=14.3 Hz, 2H).

44

Example 13: Compound 13

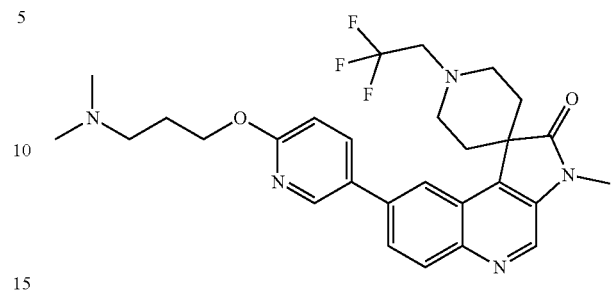

Synthetic Route

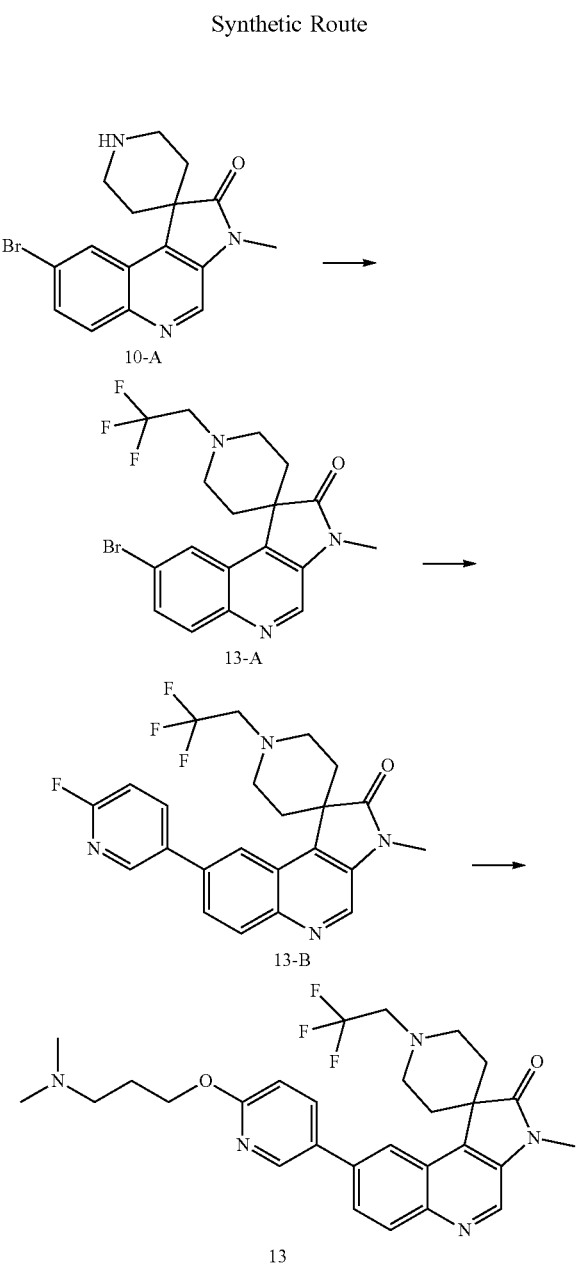

Step 1: Synthesis of Compound 13-A

Except for using the corresponding raw materials, the compound 13-A was prepared using the same method as in the preparation of compound 10-B in Example 10.

MS m/z: 428.1[M+H]+

Step 2: Synthesis of Compound 13-B

Except for using the corresponding raw materials, the compound 13-B was prepared using the same method as in the preparation of compound 10-C in Example 10.

MS m/z: 445.2[M+H]+

$^1$H NMR (400 MHz, CDCl$_3$) δ 8.73 (s, 1H), 8.58 (d, J=2.3 Hz, 1H), 8.27-8.22 (m, 2H), 8.13 (dt, J=2.6, 8.0 Hz, 1H), 7.79 (dd, J=1.8, 9.0 Hz, 1H), 7.11 (dd, J=2.9, 8.4 Hz, 1H), 3.50-3.41 (m, 2H), 3.39 (s, 3H), 3.17 (q, J=9.5 Hz, 2H), 2.94 (br dd, J=3.9, 10.9 Hz, 2H), 2.76 (dt, J=4.8, 13.3 Hz, 2H), 1.80 (br s, 2H).

Step 3: Synthesis of Compound 13

Except for using the corresponding raw materials, the compound 13 was prepared using the same method as in the preparation of compound 10 in Example 10.

MS m/z: 528.3[M+H]+

$^1$H NMR (400 MHz, CDCl$_3$) δ 8.68 (s, 1H), 8.53 (d, J=2.3 Hz, 1H), 8.23-8.18 (m, 2H), 7.94 (dd, J=2.5, 8.8 Hz, 1H), 7.79 (dd, J=1.6, 8.9 Hz, 1H), 6.90 (d, J=8.5 Hz, 1H), 4.43 (t, J=6.4 Hz, 2H), 3.46 (br t, J=11.2 Hz, 2H), 3.38 (s, 3H), 3.17 (q, J=9.7 Hz, 2H), 2.92 (br d, J=11.0 Hz, 2H), 2.78 (dt, J=4.5, 13.3 Hz, 2H), 2.53-2.46 (m, 2H), 2.28 (s, 6H), 2.06-1.96 (m, 2H), 1.77 (br s, 2H)

Example 14: Compound 14

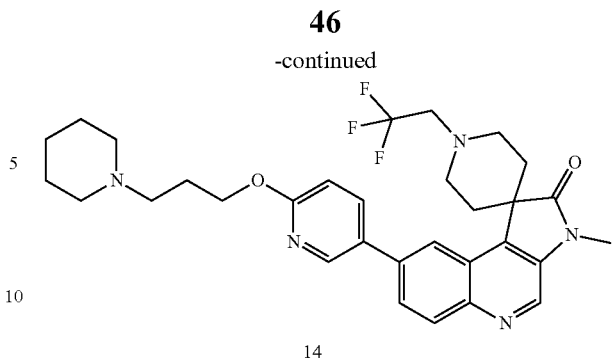

14

Step 1: Synthesis of Compound 14

Except for using the corresponding raw materials, the compound 14 was prepared using the same method as in the preparation of compound 10 in Example 10.

MS m/z: 568.3[M+H]+

$^1$H NMR (400 MHz, CDCl$_3$) δ 8.69 (s, 1H), 8.53 (d, J=2.5 Hz, 1H), 8.24-8.18 (m, 2H), 7.94 (dd, J=2.5, 8.5 Hz, 1H), 7.79 (dd, J=1.6, 8.9 Hz, 1H), 6.89 (d, J=8.5 Hz, 1H), 4.42 (t, J=6.4 Hz, 2H), 3.46 (br t, J=11.2 Hz, 2H), 3.38 (s, 3H), 3.17 (q, J=9.5 Hz, 2H), 2.92 (br d, J=11.3 Hz, 2H), 2.77 (dt, J=4.6, 13.4 Hz, 2H), 2.58-2.51 (m, 2H), 2.46 (br s, 2H), 2.10-2.00 (m, 2H), 1.77 (br d, J=14.1 Hz, 2H), 1.63 (br s, 6H), 1.46 (br s, 2H).

Example 15: Compound 15

Synthetic Route

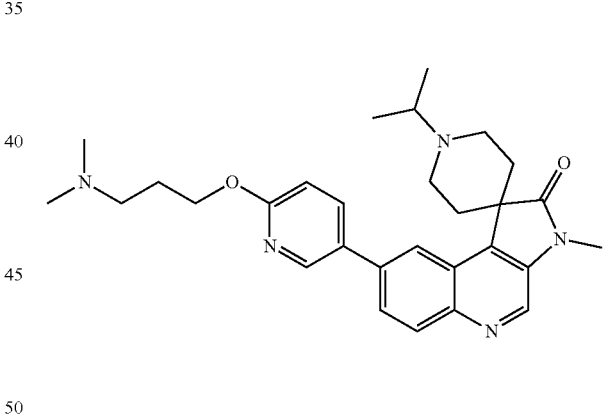

Synthetic Route

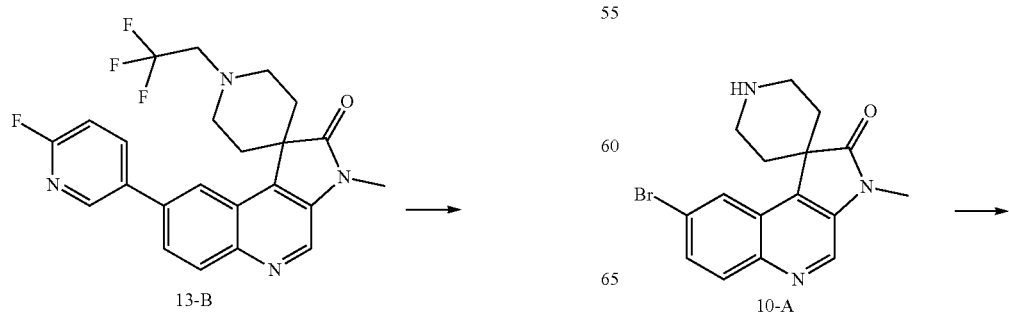

13-B

10-A

MS m/z: 488.4[M+H]+

$^1$H NMR (400 MHz, CDCl$_3$) δ 8.70 (s, 1H), 8.56 (d, J=2.3 Hz, 1H), 8.37 (s, 1H), 8.21 (d, J=8.8 Hz, 1H), 8.03 (br d, J=6.8 Hz, 1H), 7.85-7.76 (m, 1H), 6.91 (d, J=8.5 Hz, 1H), 4.44 (s, 2H), 3.39 (s, 3H), 3.37-3.26 (m, 2H), 2.97 (br s, 1H), 2.81 (br s, 4H), 2.49 (s, 2H), 2.29 (s, 6H), 2.07-1.98 (m, 2H), 1.87-1.75 (m, 2H), 1.19 (br d, J=6.5 Hz, 6H)

Example 16: Compound 16

Synthetic Route

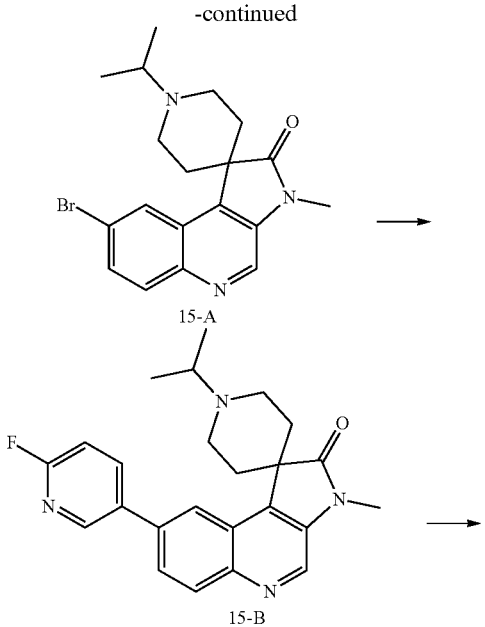

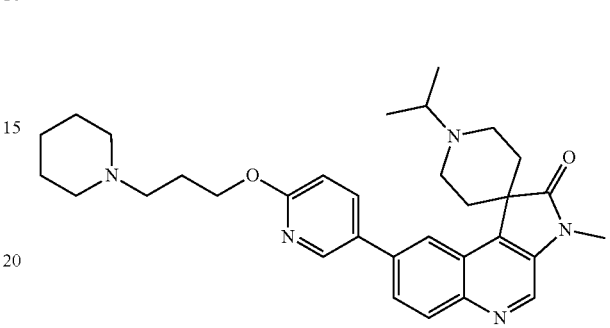

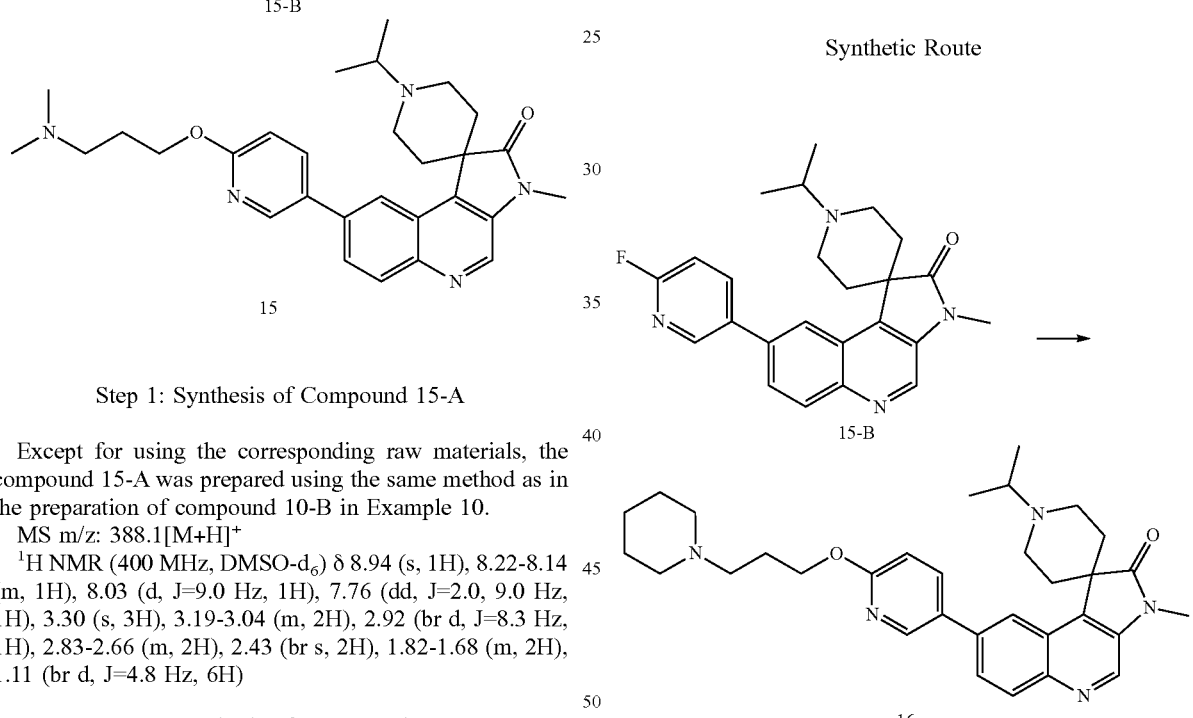

Step 1: Synthesis of Compound 15-A

Except for using the corresponding raw materials, the compound 15-A was prepared using the same method as in the preparation of compound 10-B in Example 10.

MS m/z: 388.1[M+H]+

$^1$H NMR (400 MHz, DMSO-d$_6$) δ 8.94 (s, 1H), 8.22-8.14 (m, 1H), 8.03 (d, J=9.0 Hz, 1H), 7.76 (dd, J=2.0, 9.0 Hz, 1H), 3.30 (s, 3H), 3.19-3.04 (m, 2H), 2.92 (br d, J=8.3 Hz, 1H), 2.83-2.66 (m, 2H), 2.43 (br s, 2H), 1.82-1.68 (m, 2H), 1.11 (br d, J=4.8 Hz, 6H)

Step 2: Synthesis of Compound 15-B

Except for using the corresponding raw materials, the compound 15-B was prepared using the same method as in the preparation of compound 10-C in Example 10.

MS m/z: 405.0[M+H]+

$^1$H NMR (400 MHz, CDCl$_3$) δ 8.64 (s, 1H), 8.53 (d, J=2.0 Hz, 1H), 8.39 (s, 1H), 8.15 (d, J=8.8 Hz, 2H), 7.70 (dd, J=1.8, 8.8 Hz, 1H), 6.98 (dd, J=2.8, 8.5 Hz, 1H), 3.31 (s, 3H), 3.28-3.17 (m, 2H), 2.87 (br s, 1H), 2.83-2.67 (m, 4H), 1.81-1.67 (m, 2H), 1.09 (br d, J=6.0 Hz, 6H)

Step 3: Synthesis of Compound 15

Except for using the corresponding raw materials, the compound 15 was prepared using the same method as in the preparation of compound 10 in Example 10.

Step 1: Synthesis of Compound 16

Except for using the corresponding raw materials, the compound 16 was prepared using the same method as in the preparation of compound 10 in Example 10.

MS m/z: 528.2[M+H]+

$^1$H NMR (400 MHz, CDCl$_3$) δ 8.61 (s, 1H), 8.48 (d, J=2.4 Hz, 1H), 8.29 (br s, 1H), 8.13 (d, J=8.9 Hz, 1H), 7.94 (br s, 1H), 7.71 (br d, J=8.8 Hz, 1H), 6.81 (d, J=8.6 Hz, 1H), 4.33 (s, 2H), 3.31 (s, 3H), 3.28-3.16 (m, 2H), 2.89 (br s, 1H), 2.73 (br s, 4H), 2.43 (br d, J=7.9 Hz, 2H), 2.36 (br s, 4H), 2.05 (br s, 2H), 1.99-1.93 (m, 2H), 1.72 (br d, J=12.8 Hz, 2H), 1.58-1.54 (m, 2H), 1.38 (br d, J=3.8 Hz, 2H), 1.11 (br d, J=6.1 Hz, 6H)

Example 17: Compound 17

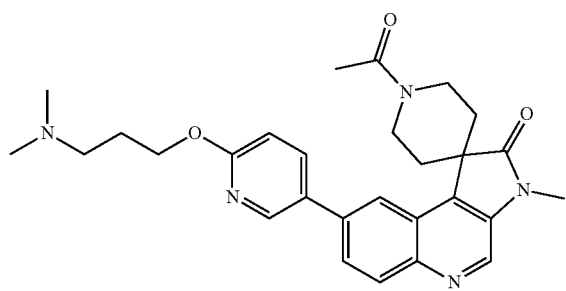

Synthetic Route

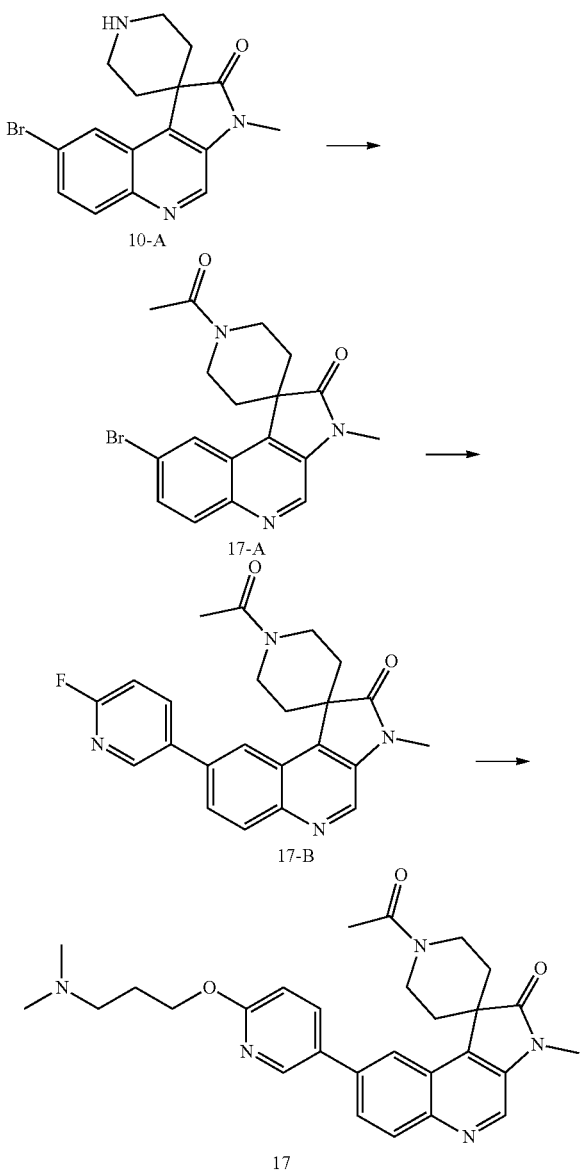

Step 1: Synthesis of Compound 17-A

Compound 10-A (150 mg, 433.25 μmol) was dissolved in dichloromethane (10 mL), N,N-diisopropylethylamine (111.99 mg, 866.50 μmol, 150.93 μL) was added, and acetylchloride (51.01 mg, 649.87 μmol, 46.38 μL) was added at 0° C. under a nitrogen atmosphere. The mixed system was warmed to 30° C., stirred for 2 h, and then concentrated to obtain a crude product, which was separated and purified by chromatography column (DCM/THF=1/0 to 4/1) to obtain compound 17-A.

MS m/z: 388.1[M+H]$^+$ $^1$H NMR (400 MHz, CDCl$_3$) δ 8.72 (s, 1H), 8.01 (d, J=9.3 Hz, 1H), 7.98 (d, J=2.0 Hz, 1H), 7.68 (dd, J=2.0, 9.0 Hz, 1H), 4.74 (br dd, J=4.9, 13.7 Hz, 1H), 4.18 (dt, J=2.8, 13.3 Hz, 1H), 3.84 (br dd, J=4.6, 13.7 Hz, 1H), 3.60 (dt, J=2.9, 13.2 Hz, 1H), 3.39 (s, 3H), 2.56-2.40 (m, 2H), 2.26 (s, 3H), 1.87-1.74 (m, 2H)

Step 2: Synthesis of Compound 17-B

Compound 17-A (85 mg, 218.93 μmol) was dissolved in anhydrous dioxane (10 mL) and water (2 mL), 2-fluoropyridine-5-boracic acid (46.27 mg, 328.39 μmol) and sodium carbonate (69.61 mg, 656.78 μmol) were added, and tetrakistriphenylphosphine palladium (37.95 mg, 32.84 μmol) was added under a nitrogen atmosphere. The mixed system was stirred at 80° C. for 4 h, and then extracted with dichloromethane (150 mL, 50 mL*3). The organic phase was collected, washed with saturated brine (50 mL), dried over anhydrous sodium sulfate, and concentrated to obtain a crude product, which was separated and purified by chromatography column (DCM:THF=1/0 to 4/1) to obtain compound 17-B.

MS m/z: 405.6[M+H]$^+$ $^1$H NMR (400 MHz, CDCl$_3$) δ 8.76 (s, 1H), 8.49 (d, J=2.5 Hz, 1H), 8.26 (d, J=8.8 Hz, 1H), 8.09-8.01 (m, 1H), 7.92 (d, J=1.8 Hz, 1H), 7.78 (dd, J=2.0, 8.8 Hz, 1H), 7.12 (dd, J=2.9, 8.4 Hz, 1H), 4.71 (br d, J=8.5 Hz, 1H), 4.20 (dt, J=2.9, 13.2 Hz, 1H), 3.84 (br d, J=9.3 Hz, 1H), 3.68-3.54 (m, 1H), 3.42 (s, 3H), 2.65-2.49 (m, 2H), 2.22 (s, 3H), 1.86 (br dd, J=14.9, 18.9 Hz, 2H)

Step 3: Synthesis of Compound 17

Sodium hydride (24.07 mg, 601.71 μmol, purity: 60%) was dissolved in N, N dimethylformamide (10 mL), and 3-dimethylamino-1-propanol (23.28 mg, 225.64 μmol, 26.39 L) was added at 0° C. under a nitrogen atmosphere and stirred for 0.5 h, and then a solution of 17-B (70 mg, 150.43 μmol) in N, N dimethylformamide (5 mL) was added. The mixed system was raised to room temperature (25° C.) and stirred for 4 h, and then quenched by adding water (20 mL). The mixed system was dispersed into 100 mL of water, and extracted with dichloromethane (150 mL, 50 mL*3). The organic phase was collected, washed with saturated brine (50 mL), dried over anhydrous sodium sulfate, and concentrated to obtain a crude product, which was separated and purified by preparative high performance liquid chromatography (neutral, mobile phase: acetonitrile-water) to obtain compound 17.

MS m/z: 488.4[M+H]$^+$ $^1$H NMR (400 MHz, CDCl$_3$) δ 8.72 (s, 1H), 8.44 (d, J=2.0 Hz, 1H), 8.22 (d, J=8.8 Hz, 1H), 7.90 (d, J=1.5 Hz, 1H), 7.85 (dd, J=2.5, 8.5 Hz, 1H), 7.79 (dd, J=1.9, 8.9 Hz, 1H), 6.90 (d, J=8.8 Hz, 1H), 4.71 (br d, J=10.0 Hz, 1H), 4.43 (t, J=6.4 Hz, 2H), 4.24-4.13 (m, 1H), 3.83 (br d, J=13.8 Hz, 1H), 3.68-3.57 (m, 1H), 3.41 (s, 3H), 2.65-2.52 (m, 2H), 2.52-2.43 (m, 2H), 2.28 (s, 6H), 2.23 (s, 3H), 2.05-1.96 (m, 2H), 1.85 (br t, J=14.2 Hz, 2H)

Example 18: Compound 18

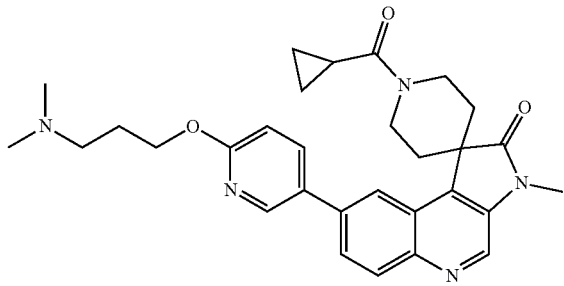

Synthetic Route

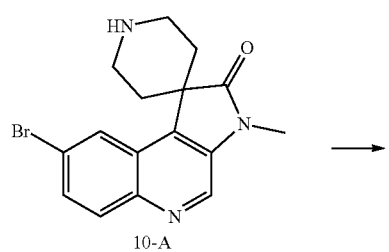
10-A

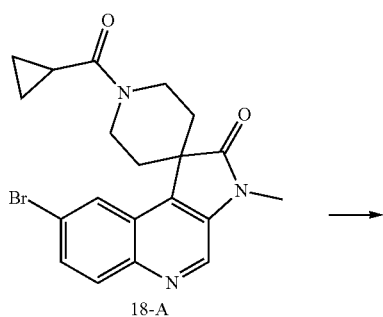
18-A

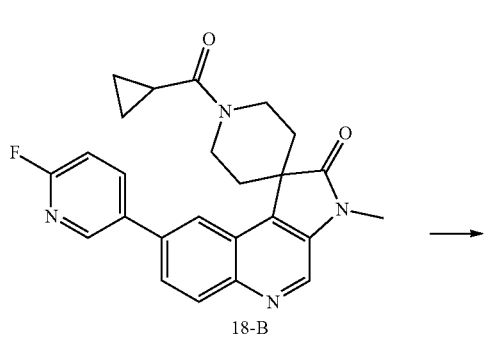
18-B

-continued

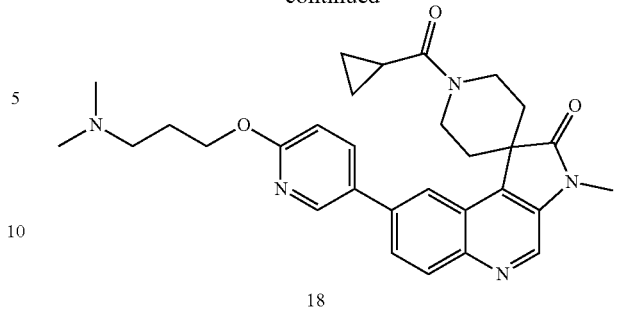
18

Step 1: Synthesis of Compound 18-A

Except for using the corresponding raw materials, the compound 18-A was prepared using the same method as in the preparation of compound 17-A in Example 17.

MS m/z: 414.1[M+H]$^+$

Step 2: Synthesis of Compound 18-B

Except for using the corresponding raw materials, the compound 18-B was prepared using the same method as in the preparation of compound 17-B in Example 17.

MS m/z: 431.2[M+H]$^+$ $^1$H NMR (400 MHz, CDCl$_3$) δ 8.76 (s, 1H), 8.50 (d, J=2.5 Hz, 1H), 8.26 (d, J=9.0 Hz, 1H), 8.05 (dt, J=2.6, 8.0 Hz, 1H), 7.93 (d, J=1.5 Hz, 1H), 7.79 (dd, J=1.9, 8.9 Hz, 1H), 7.11 (dd, J=2.8, 8.5 Hz, 1H), 4.67 (br d, J=12.5 Hz, 1H), 4.26 (br d, J=7.5 Hz, 2H), 3.67 (br t, J=12.8 Hz, 1H), 3.42 (s, 3H), 2.59 (br d, J=12.3 Hz, 2H), 1.95-1.85 (m, 2H), 1.79 (br d, J=13.1 Hz, 1H), 1.12 (br s, 1H), 1.00 (br s, 1H), 0.83 (dd, J=3.6, 7.9 Hz, 2H)

Step 3: Synthesis of Compound 18

Except for using the corresponding raw materials, the compound 18 was prepared using the same method as in the preparation of compound 17 in Example 17.

MS m/z: 514.4[M+H]$^+$ $^1$H NMR (400 MHz, CDCl$_3$) δ 8.72 (s, 1H), 8.45 (d, J=2.3 Hz, 1H), 8.21 (d, J=8.8 Hz, 1H), 7.91 (d, J=1.8 Hz, 1H), 7.86 (dd, J=2.5, 8.5 Hz, 1H), 7.80 (dd, J=1.8, 8.8 Hz, 1H), 6.88 (d, J=8.3 Hz, 1H), 4.67 (br d, J=11.0 Hz, 1H), 4.43 (t, J=6.4 Hz, 2H), 4.25 (br d, J=8.3 Hz, 2H), 3.67 (br t, J=12.3 Hz, 1H), 3.41 (s, 3H), 2.71-2.52 (m, 4H), 2.34 (s, 6H), 2.09-2.05 (m, 1H), 2.04-2.00 (m, 1H), 1.95-1.83 (m, 3H), 1.16-1.01 (m, 2H), 0.89-0.79 (m, 2H)

Example 19: Compound 19

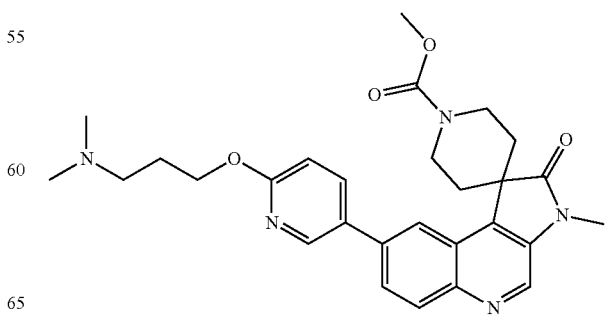 [SMILES: COC(=O)N1CCC2(CC1)C(=O)N(C)c1cnc3ccc(-c4ccc(OCCCN5CCCCC5)nc4)cc3c12]

Synthetic Route

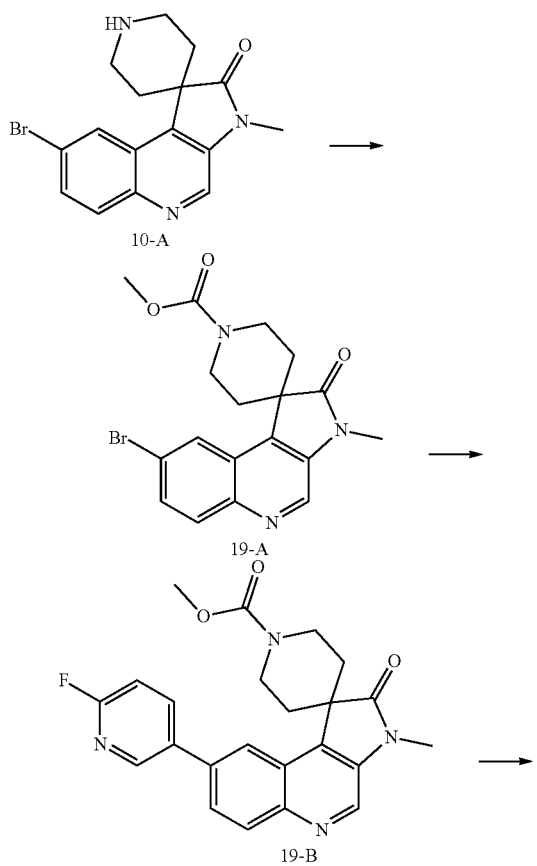

Step 1: Synthesis of Compound 19-A

Except for using the corresponding raw materials, the compound 19-A was prepared using the same method as in the preparation of compound 17-A in Example 17.

$^1$H NMR (400 MHz, CDCl$_3$) δ 8.71 (s, 1H), 8.03-7.99 (m, 2H), 7.67 (dd, J=2.0, 9.0 Hz, 1H), 4.35-4.09 (m, 2H), 3.82 (s, 3H), 3.38 (s, 3H), 2.57-2.44 (m, 2H), 1.74 (br d, J=14.1 Hz, 2H), 1.04 (br s, 2H)

Step 2: Synthesis of Compound 19-B

Except for using the corresponding raw materials, the compound 19-B was prepared using the same method as in the preparation of compound 17-B in Example 17.

MS m/z: 421.1[M+H]$^+$ $^1$H NMR (400 MHz, CDCl$_3$) δ 8.75 (s, 1H), 8.51 (d, J=2.0 Hz, 1H), 8.25 (d, J=9.0 Hz, 1H), 8.07 (dt, J=2.5, 7.9 Hz, 1H), 7.97 (s, 1H), 7.78 (dd, J=1.8, 8.8 Hz, 1H), 7.11 (dd, J=2.9, 8.4 Hz, 1H), 4.24 (br s, 2H), 3.83 (br s, 2H), 3.79 (s, 3H), 3.41 (s, 3H), 2.64-2.51 (m, 2H), 1.79 (br d, J=14.1 Hz, 2H)

Step 3: Synthesis of Compound 19

Except for using the corresponding raw materials, the compound 19 was prepared using the same method as in the preparation of compound 17 in Example 17.

MS m/z: 504.2[M+H]$^+$ $^1$H NMR (400 MHz, CDCl$_3$) δ 8.71 (s, 1H), 8.46 (d, J=2.3 Hz, 1H), 8.21 (d, J=8.8 Hz, 1H), 7.94 (d, J=1.5 Hz, 1H), 7.88 (dd, J=2.5, 8.5 Hz, 1H), 7.78 (dd, J=1.9, 8.9 Hz, 1H), 6.89 (d, J=8.8 Hz, 1H), 4.42 (t, J=6.4 Hz, 2H), 4.32-4.08 (m, 2H), 3.92-3.81 (m, 2H), 3.79 (s, 3H), 3.40 (s, 3H), 2.65-2.55 (m, 2H), 2.53-2.47 (m, 2H), 2.29 (s, 6H), 2.06-1.97 (m, 2H), 1.76 (br s, 2H)

Example 20: Compound 20

Synthetic Route

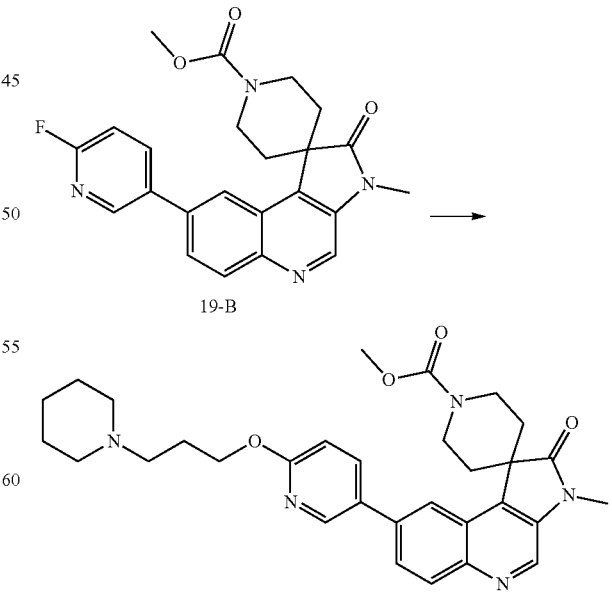

Step 1: Synthesis of Compound 20

Except for using the corresponding raw materials, the compound 20 was prepared using the same method as in the preparation of compound 17 in Example 17.

MS m/z: 544.3[M+H]+

1H NMR (400 MHz, CDCl3) δ 8.71 (s, 1H), 8.46 (s, 1H), 8.21 (d, J=8.8 Hz, 1H), 7.94 (s, 1H), 7.87 (dd, J=2.1, 8.7 Hz, 1H), 7.78 (br d, J=9.0 Hz, 1H), 6.88 (d, J=8.5 Hz, 1H), 4.41 (br t, J=6.4 Hz, 2H), 4.33-4.07 (m, 2H), 3.94-3.81 (m, 2H), 3.79 (s, 3H), 3.40 (s, 3H), 2.66-2.37 (m, 8H), 2.10-1.98 (m, 2H), 1.78 (br d, J=12.8 Hz, 6H), 1.45 (br s, 2H)

Example 21: Compound 21

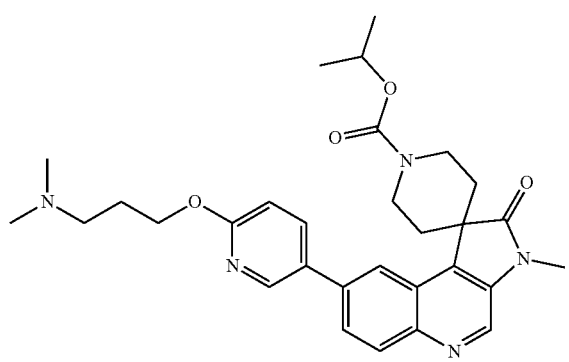

Synthetic Route

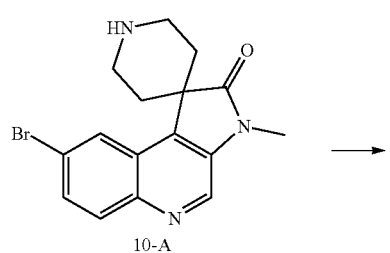
10-A

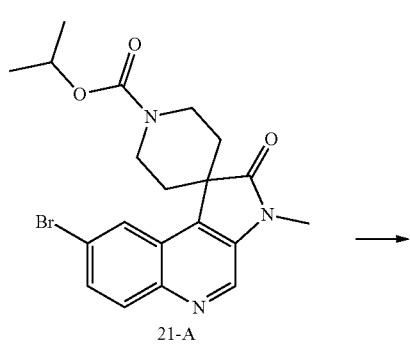
21-A

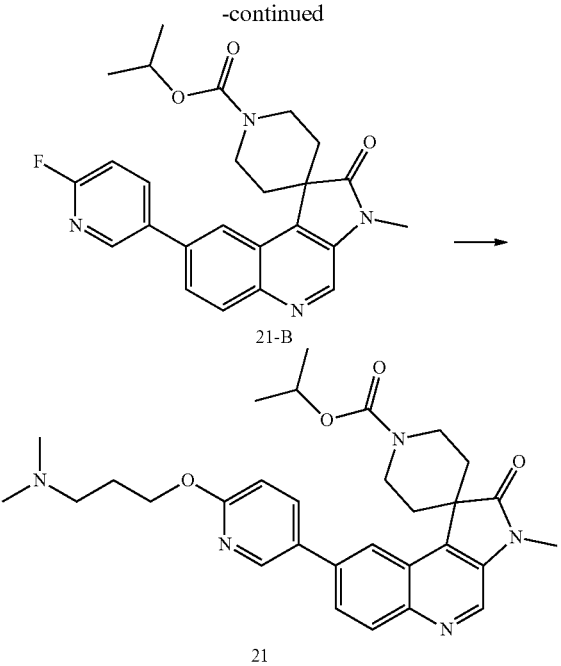
21-B

21

Step 1: Synthesis of Compound 21-A

Except for using the corresponding raw materials, the compound 21-A was prepared using the same method as in the preparation of compound 17-A in Example 17.

MS m/z: 432.2[M+H]+

Step 2: Synthesis of Compound 21-B

Except for using the corresponding raw materials, the compound 21-B was prepared using the same method as in the preparation of compound 17-B in Example 17.

MS m/z: 449.2[M+H]+

1H NMR (400 MHz, CDCl3) δ 8.75 (s, 1H), 8.51 (d, J=2.5 Hz, 1H), 8.25 (d, J=8.8 Hz, 1H), 8.09-8.02 (m, 1H), 7.96 (d, J=1.8 Hz, 1H), 7.78 (dd, J=2.0, 8.8 Hz, 1H), 7.08 (dd, J=2.9, 8.4 Hz, 1H), 5.02 (td, J=6.3, 12.4 Hz, 1H), 4.15 (br s, 2H), 3.83 (br s, 2H), 3.41 (s, 3H), 2.57 (br s, 2H), 1.77 (br d, J=14.1 Hz, 2H), 1.28 (d, J=6.3 Hz, 6H)

Step 3: Synthesis of Compound 21

Except for using the corresponding raw materials, the compound 21 was prepared using the same method as in the preparation of compound 17 in Example 17.

MS m/z: 532.3[M+H]+

1H NMR (400 MHz, CD3OD) δ 8.77 (s, 1H), 8.45 (d, J=2.3 Hz, 1H), 8.12 (d, J=8.8 Hz, 1H), 8.02 (dd, J=2.5, 8.8 Hz, 1H), 7.96 (d, J=1.5 Hz, 1H), 7.85 (dd, J=1.8, 9.0 Hz, 1H), 6.92 (d, J=8.8 Hz, 1H), 4.97 (td, J=6.2, 12.5 Hz, 1H), 4.44 (t, J=6.0 Hz, 2H), 4.12 (br dd, J=3.5, 13.3 Hz, 2H), 3.84-3.71 (m, 2H), 3.38 (s, 3H), 3.13-3.06 (m, 2H), 2.74 (s, 6H), 2.60-2.49 (m, 2H), 2.23-2.13 (m, 2H), 1.73 (br d, J=14.1 Hz, 2H), 1.27 (d, J=6.3 Hz, 6H)

Example 22: Compound 22

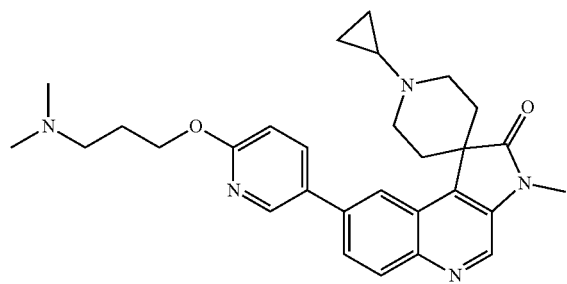

Synthetic Route

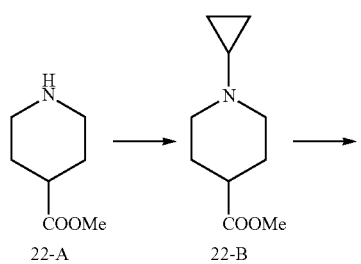

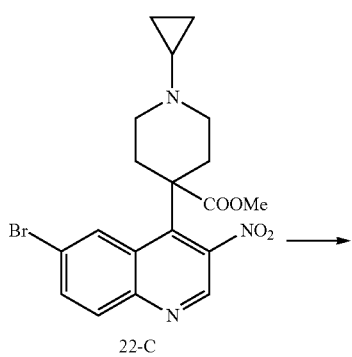

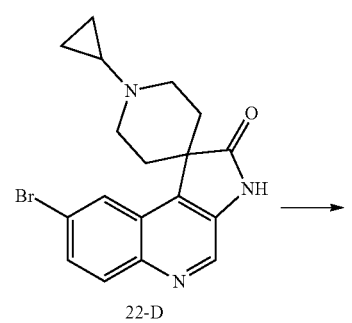

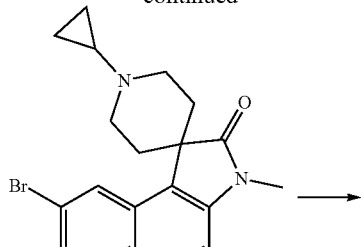

22-E

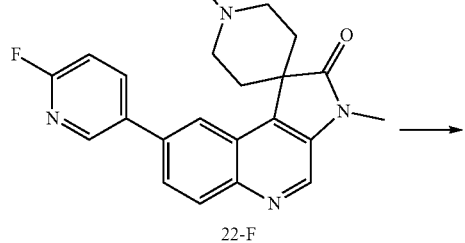

22-F

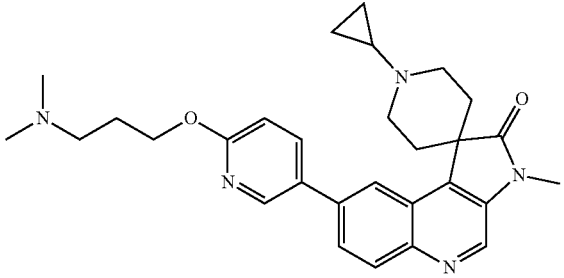

22

Step 1: Synthesis of Compound 22-B 1,2-dichloroethane (100 mL) was added to methyl 4-piperidinecarboxylate (10 g, 69.84 mmol), cyclopropylboronic acid (12.00 g, 139.68 mmol), pyridine (5.52 g, 69.84 mmol, 5.64 mL) and sodium carbonate (14.80 g, 139.68 mmol, 2 eq), replaced three times with oxygen, and stirred for 16 h at 70° C. under oxygen atmosphere. After completion of the reaction, the reaction was cooled 0° C. and quenched by adding 200 mL of water. Then 100 mL of ammonia water was added, and extracted with dichloromethane (150 mL, 50 mL*3). The organic phase was combined, washed with saturated brine (200 mL), and dried over anhydrous sodium sulfate. After removing the desiccant by filtration, the solvent was removed under reduced pressure to obtain a crude product. The crude product was purified by column chromatography (0 to 10% EtOAc/PE) to obtain compound 22-B.

$^1$H NMR (400 MHz, CDCl$_3$) δ 3.66 (s, 3H), 3.03-2.95 (m, 2H), 2.29 (tt, J=4.0, 11.2 Hz, 1H), 2.20 (dt, J=2.5, 11.5 Hz, 2H), 1.91-1.83 (m, 2H), 1.73-1.62 (m, 2H), 1.59-1.52 (m, 1H), 0.46-0.40 (m, 2H), 0.40-0.36 (m, 2H)

Step 2: Synthesis of Compound 22-C

Except for using the corresponding raw materials, the compound 22-C was prepared using the same method as in the preparation of compound 1-A in Example 1.

MS m/z: 434.0[M+H]+

1H NMR (400 MHz, CDCl3) δ 8.75 (s, 1H), 8.68 (d, J=1.8 Hz, 1H), 8.03 (d, J=8.8 Hz, 1H), 7.86 (dd, J=1.9, 8.9 Hz, 1H), 3.67 (s, 3H), 2.95 (br d, J=12.3 Hz, 2H), 2.81-2.70 (m, 2H), 2.55 (br d, J=13.1 Hz, 2H), 2.32-2.22 (m, 2H), 1.77-1.66 (m, 1H), 0.45 (br d, J=7.0 Hz, 2H), 0.42 (br d, J=4.3 Hz, 2H)

Step 3: Synthesis of Compound 22-D

Compound 22-C (1.7 g, 3.91 mmol) was dissolved in THF (70 mL), a solution of NH4Cl (2.09 g, 39.14 mmol) in water (70 mL) was added, and then a zinc powder (2.56 g, 39.14 mmol) was added. The reaction solution was stirred at 70° C. for 24 h. After completion of the reaction, the zinc powder was removed, and the mixed solution was concentrated to obtain a crude product which was directly used in the next step.

MS m/z: 371.9[M+H]+

Step 4: Synthesis of Compound 22-E

A solution of sodium hydroxide (322.36 mg, 8.06 mmol) and tetrabutylammonium bromide (64.95 mg, 201.47 μmol) in water (20 mL) was added to a solution of 22-D (1.5 g, 4.03 mmol) in dichloromethane (40 mL). Then iodomethane (3.660 g, 25.79 mmol, 1.61 mL) was added dropwise, and the reaction solution was stirred at 20° C. for 48 h. After completion of the reaction, the reaction system was added with 50 mL of water at room temperature to quench the reaction, and extracted with dichloromethane (90 mL, 30 mL*3). The organic phase was combined, washed with saturated brine (100 mL), and dried over anhydrous sodium sulfate. After removing the desiccant by filtration, a solvent was removed under reduced pressure to obtain a crude compound 22-E, which was directly used in the next step.

MS m/z: 386.1[M+H]+

Step 5: Synthesis of Compound 22-F

Under nitrogen protection, 1,4-dioxane (20 mL) and H2O (20 mL) were added to a reaction system of compound 22-E (1 g, 2.53 mmol), 2-fluoropyridine-5-boracic acid (534.71 mg, 3.79 mmol), tetrakistriphenylphosphine palladium (292.34 mg, 252.98 μmol) and sodium carbonate (804.41 mg, 7.59 mmol), and stirred at 80° C. for 16 h. After completion of the reaction, a solvent was removed under reduced pressure to obtain a crude compound 22-F, which was directly used in the next step.

MS m/z: 403.1[M+H]+

Step 6: Synthesis of Compound 22

Except for using the corresponding raw materials, the compound 22 was prepared using the same method as in the preparation of compound 1 in Example 1.

MS m/z: 486.3[M+H]+

1H NMR (400 MHz, CDCl3) δ 8.68 (s, 1H), 8.51 (d, J=2.0 Hz, 1H), 8.24 (s, 1H), 8.19 (d, J=8.8 Hz, 1H), 7.94 (dd, J=2.0, 8.5 Hz, 1H), 7.76 (br d, J=8.8 Hz, 1H), 6.87 (d, J=8.5 Hz, 1H), 4.41 (t, J=6.4 Hz, 2H), 3.38 (s, 3H), 3.27 (br t, J=11.4 Hz, 2H), 2.97 (br d, J=9.5 Hz, 2H), 2.68 (dt, J=4.4, 13.2 Hz, 2H), 2.47 (br t, J=7.4 Hz, 2H), 2.27 (s, 6H), 1.98 (br s, 2H), 1.88 (br d, J=4.3 Hz, 1H), 1.75 (br d, J=13.8 Hz, 2H), 0.52 (br s, 4H)

Example 23: Compound 23

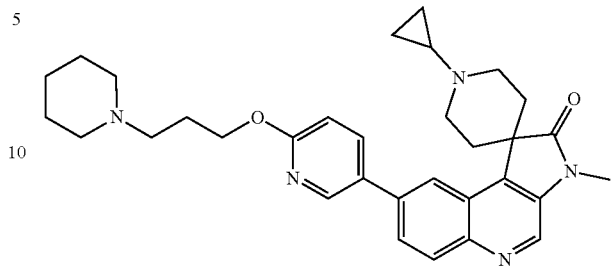

Synthetic Route

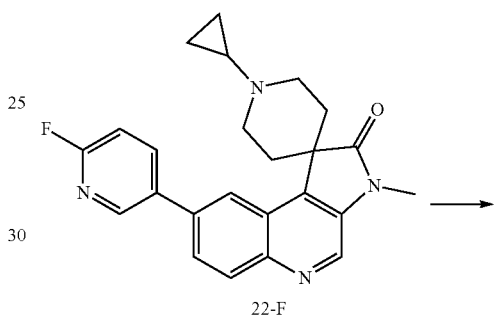

22-F

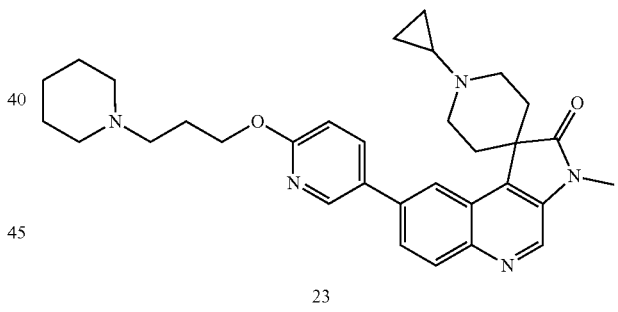

23

Step 1: Synthesis of Compound 23

Except for using the corresponding raw materials, the compound 23 was prepared using the same method as in the preparation of compound 1 in Example 1.

MS m/z: 526.3[M+H]+

1H NMR (400 MHz, CDCl3) δ 8.68 (s, 1H), 8.51 (d, J=2.3 Hz, 1H), 8.24 (d, J=1.5 Hz, 1H), 8.19 (d, J=9.0 Hz, 1H), 7.94 (dd, J=2.5, 8.5 Hz, 1H), 7.76 (dd, J=1.8, 8.8 Hz, 1H), 6.87 (d, J=8.5 Hz, 1H), 4.40 (t, J=6.5 Hz, 2H), 3.38 (s, 3H), 3.32-3.22 (m, 2H), 3.01-2.93 (m, 2H), 2.68 (dt, J=4.5, 13.3 Hz, 2H), 2.55-2.49 (m, 2H), 2.44 (br s, 2H), 2.08-1.97 (m, 6H), 1.91-1.86 (m, 1H), 1.75 (br d, J=13.8 Hz, 2H), 1.65-1.62 (m, 1H), 1.60-1.58 (m, 1H), 1.45 (br s, 2H), 0.55-0.49 (m, 4H)

Example 24: Compound 24

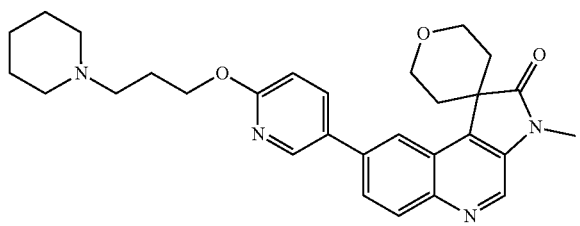 [SMILES: CN1C(=O)C2(CCOCC2)c2c1cnc1ccc(-c3ccc(OCCCN4CCCCC4)nc3)cc21]

Synthetic Route

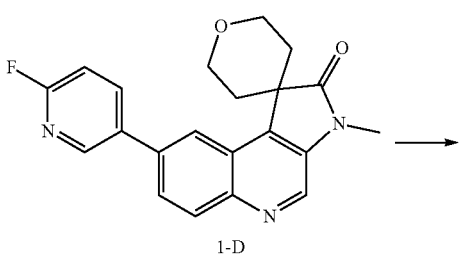

1-D

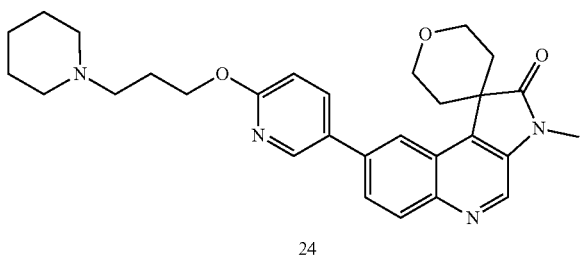

24

Step 1: Synthesis of Compound 24

Sodium hydride (101.26 mg, 2.53 mmol, purity: 60%) was dissolved in N,N-dimethylformamide (10 mL), and a solution of compound 11-C (181.31 mg, 1.27 mmol) in N,N-dimethylformamide (5 mL) was added at 0° C. under a nitrogen atmosphere, and stirred for 0.5 h, and then a solution of 1-D (230 mg, 632.94 μmol) in N,N-dimethylformamide (5 mL) was added. The mixed system was raised to room temperature (25° C.), continuously stirred 2 h under a nitrogen atmosphere, then quenched by adding water (10 mL), and extracted with dichloromethane (150 mL, 50 mL*3). The organic phase was collected, and the organic phase was concentrated to obtain a crude product, which was separated and purified by preparative high performance liquid chromatography ([water (10 mM ammonium bicarbonate)-acetonitrile]; acetonitrile B %: 28%-58%, 7 min) to obtain compound 24.

MS m/z: 487.3[M+H]$^+$ $^1$H NMR (400 MHz, CDCl$_3$) δ 8.69 (s, 1H), 8.50 (d, J=2.0 Hz, 1H), 8.20 (d, J=8.8 Hz, 1H), 8.15 (s, 1H), 7.91 (dd, J=2.3, 8.5 Hz, 1H), 7.78 (br d, J=8.0 Hz, 1H), 6.87 (d, J=8.5 Hz, 1H), 4.54-4.34 (m, 4H), 3.97 (br dd, J=4.8, 11.5 Hz, 2H), 3.38 (s, 3H), 2.74 (dt, J=4.9, 13.2 Hz, 2H), 2.54-2.46 (m, 2H), 2.42 (br s, 2H), 2.12 (br s, 2H), 2.02 (td, J=6.9, 14.3 Hz, 2H), 1.68 (br d, J=13.8 Hz, 2H), 1.62-1.53 (m, 4H), 1.43 (br s, 2H)

Example 25: Compound 25

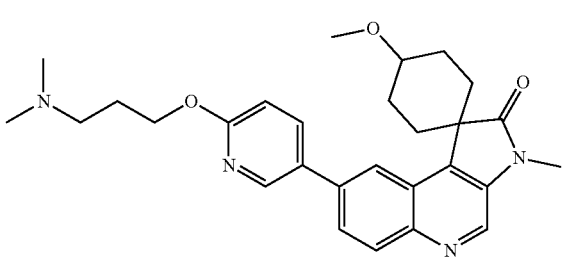

Synthetic Route

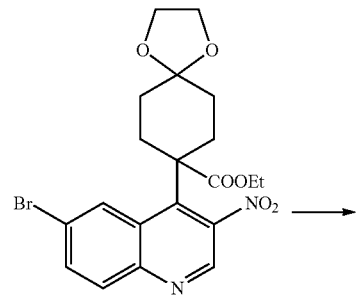

A

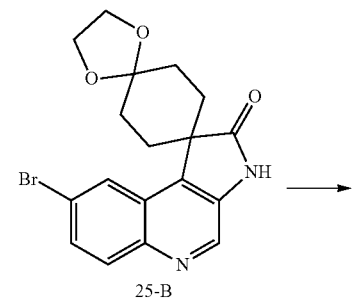

25-A

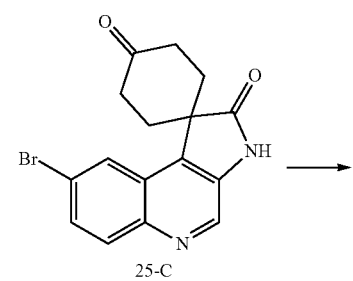

25-B

25-C

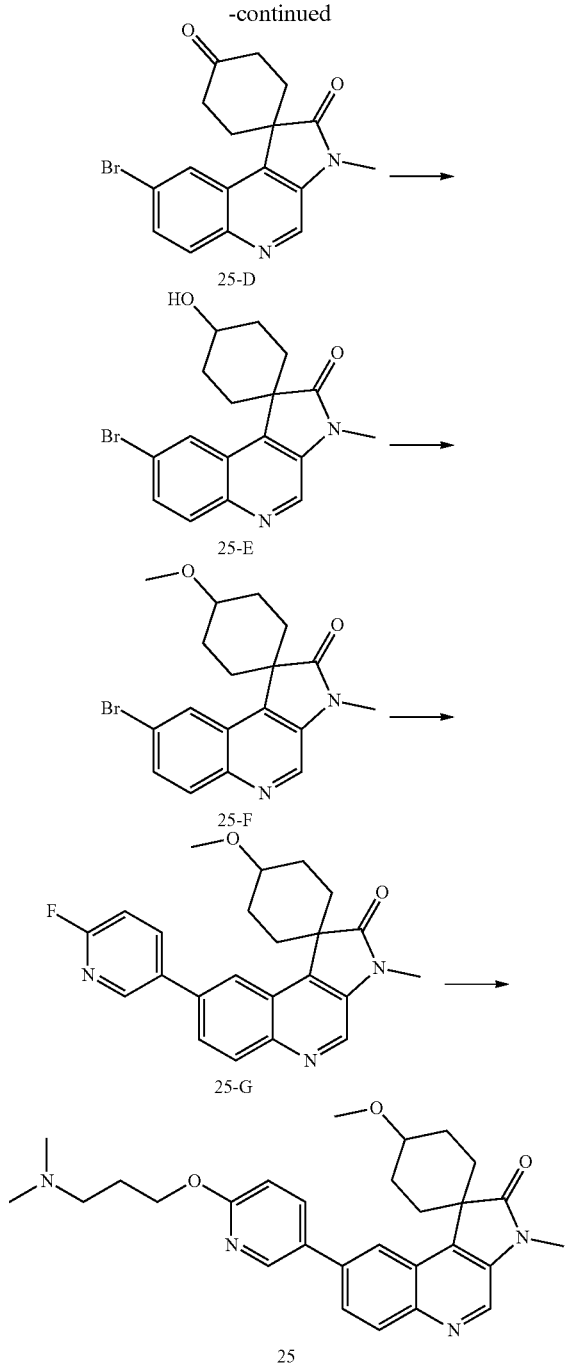

Step 1: Synthesis of Compound 25-A

Except for using the corresponding raw materials, the compound 25-A was prepared using the same method as in the preparation of compound 1-A in Example 1.

MS m/z: 465.0[M+H]$^+$

Step 2: Synthesis of Compound 25-B

Except for using the corresponding raw materials, the compound 25-B was prepared using the same method as in the preparation of compound 1-B in Example 1.

MS m/z: 389.4[M+H]$^+$

Step 3: Synthesis of Compound 25-C

Compound 25-B (3.2 g, 8.22 mmol) was dissolved in tetrahydrofuran (10 mL), and trifluoroacetic acid (15.40 g, 135.06 mmol, 10.00 mL) and water (10.00 g, 555.08 mmol, 10 mL) were added. The mixed system was stirred at room temperature (25° C.) for 12 h, then adjusted to achieve pH=7 to 8 with sodium hydroxide (1 M), and extracted with EtOAc (200 mL, 100 mL*2). The organic phase was collected, and concentrated to obtain a crude product, which was separated and purified by chromatography column (dichloromethane/tetrahydrofuran=1/0 to 4/1) to obtain compound 25-C.

MS m/z: 345.1[M+H]$^+$

Step 4: Synthesis of Compound 25-D

Except for using the corresponding raw materials, the compound 25-D was prepared using the same method as in the preparation of compound 1-C in Example 1.

MS m/z: 359.1[M+H]$^+$

Step 5: Synthesis of Compound 25-E

Compound 25-D (0.367 g, 1.02 mmol) was dissolved in methanol (20 mL), and sodium borohydride (77.30 mg, 2.04 mmol) was added at 0° C. under a nitrogen atmosphere. The mixed system was raised to room temperature (20° C.), continuously stirred for 3 h, then quenched by adding water (20 mL), and extracted with dichloromethane/methanol=10/1 (50 mL). The organic phase was collected, and concentrated to obtain a crude product, which was separated and purified by chromatography column (DCM/THF=I/O to 4/1) to obtain compound 25-E.

MS m/z: 360.9[M+H]$^+$

Step 6: Synthesis of Compound 25-F

Sodium hydride (106.29 mg, 2.66 mmol, purity: 60%) was dissolved in tetrahydrofuran (10 mL), and a solution of 25-E (320 mg, 885.86 μmol) in tetrahydrofuran (10 mL) was added at 0° C. under a nitrogen atmosphere, and stirred at 0° C. for 0.5 h. Then iodomethane (502.95 mg, 3.54 mmol, 220.59 μL) was added under a nitrogen atmosphere. The mixed system was raised to room temperature (25° C.), and stirred for 2 h under a nitrogen atmosphere. The mixed solution was quenched by dispersing into 50 mL of water, extracted with dichloromethane (150 mL, 50 mL*3), and washed with saturated brine (50 mL). The organic phase was collected, dried over anhydrous sodium sulfate, and separated and purified by chromatography column (dichloromethane/tetrahydrofuran=1/0 to 10/1) to obtain compound 25-F.

MS m/z 375.1[M+H]$^+$

Step 6: Synthesis of Compound 25-G

Except for using the corresponding raw materials, the compound 25-G was prepared using the same method as in the preparation of compound 1-D in Example 1.

MS m/z: 392.6[M+H]$^+$

Step 7: Synthesis of Compound 25

Except for using the corresponding raw materials, the compound 25 was prepared using the same method as in the preparation of compound 1 in Example 1.

MS m/z: 475.2[M+H]+

¹H NMR (400 MHz, CDCl₃) δ 8.68 (s, 1H), 8.50 (d, J=2.5 Hz, 1H), 8.20 (d, J=8.8 Hz, 1H), 8.01 (s, 1H), 7.90 (dd, J=2.5, 8.5 Hz, 1H), 7.76 (dd, J=1.5, 8.8 Hz, 1H), 6.91 (d, J=8.5 Hz, 1H), 4.43 (t, J=6.4 Hz, 2H), 3.48 (s, 3H), 3.38 (s, 3H), 2.53-2.44 (m, 4H), 2.41-2.35 (m, 2H), 2.28 (s, 6H), 2.10-1.97 (m, 4H), 1.91 (br d, J=13.8 Hz, 2H), 1.78 (br s, 2H)

Example 26: Compound 26

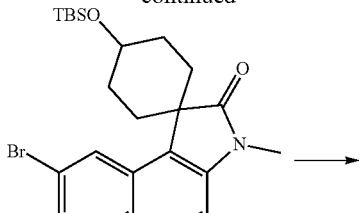

Synthetic Route

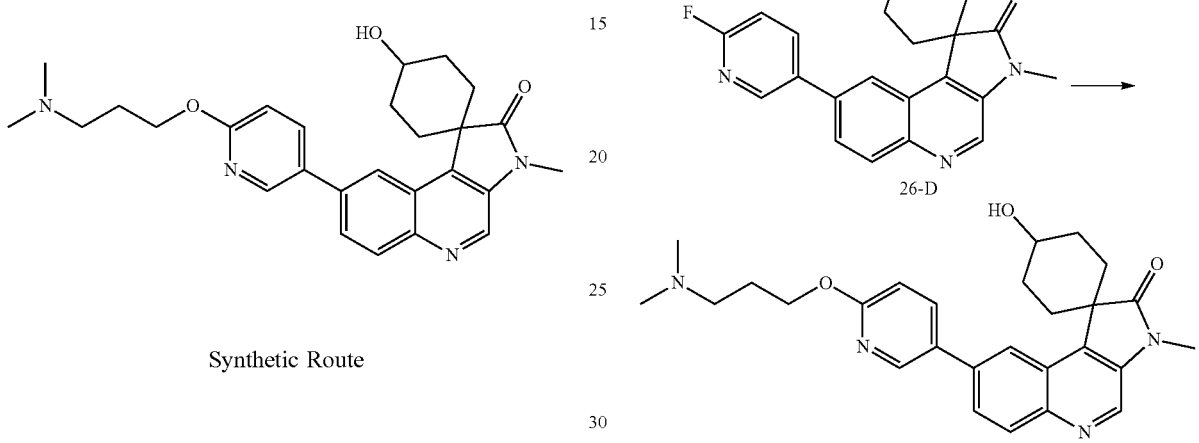

Step 1: Synthesis of Compound 26-A

Compound 25-C (1.05 g, 3.04 mmol) was dissolved in methanol (20 mL), and sodium borohydride (172.62 mg, 4.56 mmol) was added at 0° C. under a nitrogen atmosphere. The mixed system was raised to room temperature (20° C.), continuously stirred for 3 h, then quenched by adding water (20 mL), and extracted with dichloromethane (100 mL, 50 mL*2). The organic phase was collected, and concentrated to obtain a crude product, which was separated and purified by chromatography column (dichloromethane/tetrahydrofuran=1/0 to 4/1) to obtain compound 26-A.

MS m/z: 347.0[M+H]+

Step 2: Synthesis of Compound 26-B

Compound 26-A (840 mg, 2.42 mmol) was dissolved in dichloromethane (5 mL), a solution of sodium hydroxide (387.09 mg, 9.68 mmol) in water (5 mL), and tetrabutylammonium bromide (39.00 mg, 120.97 μmol) were added, and iodomethane (1.37 g, 9.68 mmol, 602.44 μL) was added at 0° C. under a nitrogen atmosphere. The mixed system was raised to room temperature (25° C.) and stirred for 3 h under a nitrogen atmosphere, and then the mixed solution was dispersed into 50 mL of water, and extracted with dichloromethane (100 mL, 50 mL*2). The organic phase was collected and concentrated to obtain a crude product, which was separated and purified by chromatography column (dichloromethane/tetrahydrofuran=1/0 to 5/1) to obtain 26-B.

MS m/z: 361.1[M+H]+

Step 3: Synthesis of Compound 26-C

Compound 26-B (260 mg, 719.76 μmol) was dissolved in N,N dimethylformamide (10 mL), and pyridine (56.93 mg, 719.76 μmol, 58.09 μL) and TBSOTf (190.26 mg, 719.76 mol, 165.44 μL) were added, and stirred for 3 h at room temperature (25° C.), then washed by adding 300 mL (100 mL*3) of water, and extracted with 150 mL (50 mL*3) of dichloromethane. The organic phase was collected, and concentrated to obtain a crude product, which was separated and purified by column chromatography (dichloromethane/tetrahydrofuran=1/0 to 10/1) to obtain 26-C.

MS m/z: 474.6[M+H]$^+$

Step 4: Synthesis of Compound 26-D

Except for using the corresponding raw materials, the compound 26-D was prepared using the same method as in the preparation of compound 1-D in Example 1.

MS m/z: 492.3[M+H]$^+$ $^1$H NMR (400 MHz, CDCl$_3$) δ 8.72 (s, 1H), 8.55 (d, J=2.3 Hz, 1H), 8.24 (d, J=9.0 Hz, 1H), 8.12-8.05 (m, 1H), 8.03 (d, J=1.8 Hz, 1H), 7.75 (dd, J=2.0, 8.8 Hz, 1H), 7.12 (dd, J=2.8, 8.5 Hz, 1H), 3.39 (s, 3H), 2.55-2.40 (m, 4H), 1.94-1.78 (m, 4H), 0.97-0.88 (m, 9H), 0.13 (s, 6H)

Step 5: Synthesis of Compound 26

Except for using the corresponding raw materials, the compound 26 was prepared using the same method as in the preparation of compound 1 in Example 1.

MS m/z: 461.3[M+H]$^+$

1H NMR (400 MHz, CDCl$_3$) δ 8.69 (s, 1H), 8.49 (d, J=2.3 Hz, 1H), 8.21 (d, J=8.8 Hz, 1H), 8.00 (d, J=1.5 Hz, 1H), 7.89 (dd, J=2.6, 8.7 Hz, 1H), 7.77 (dd, J=1.8, 8.8 Hz, 1H), 6.90 (d, J=8.5 Hz, 1H), 4.43 (t, J=6.5 Hz, 2H), 3.99-3.89 (m, 1H), 3.39 (s, 3H), 2.58-2.36 (m, 6H), 2.28 (s, 6H), 2.06-1.96 (m, 4H), 1.89 (br d, J=13.8 Hz, 2H)

Example 27: Compound 27

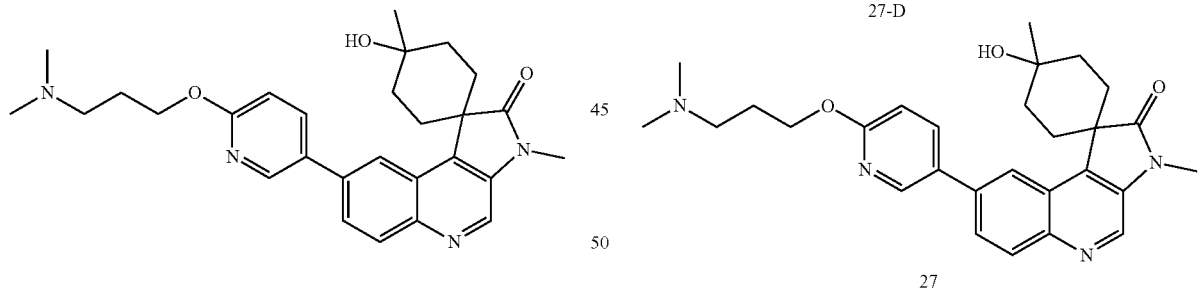

Synthetic Route

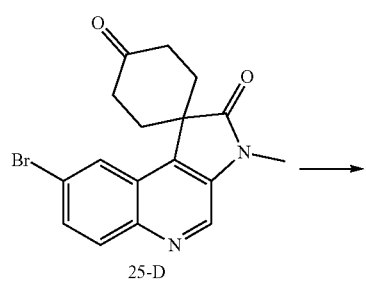

Step 1: Synthesis of Compound 27-A

Compound 25-D (900 mg, 2.51 mmol) was dissolved in tetrahydrofuran (20 mL) at 0° C., and methyl magnesium bromide (4 M, 1.88 mL) was added dropwise under a nitrogen atmosphere. The mixed system was raised to 25° C., and stirred for 2 h under a nitrogen atmosphere, and then the reaction system was quenched with water (50 mL), and extracted with dichloromethane/isopropanol=10/1 (50 mL*3). The organic phase was collected, separated and purified by chromatography column (DCM/tetrahydrofuran=1/0 to 3/1) to obtain compound 27-A.

MS m/z: 375.0[M+H]$^+$

Step 2: Synthesis of Compound 27-B

Compound 27-A (380 mg, 1.01 mmol) was dissolved in dichloromethane (10 mL), and TBSOTf (401.52 mg, 1.52 mmol, 349.14 μL) and triethylamine (204.94 mg, 2.03 mmol, 281.89 μL) were added. The mixed system was stirred for 12 h at room temperature (25° C.), then washed by adding 300 mL (100 mL*3) of water, and extracted with dichloromethane (150 mL, 50 mL*3). The organic phase was collected, and concentrated to obtain a crude product, which was separated and purified by column chromatography (dichloromethane/tetrahydrofuran=1/0 to 10/1) to obtain 27-B.

MS m/z: 489.3[M+H]$^+$ $^1$H NMR (400 MHz, CDCl$_3$) δ 8.68 (s, 1H), 8.10 (d, J=2.0 Hz, 1H), 8.00 (d, J=9.0 Hz, 1H), 7.66 (dd, J=2.3, 9.0 Hz, 1H), 3.36 (s, 3H), 2.71-2.54 (m, 2H), 2.41 (dt, J=3.8, 14.2 Hz, 2H), 1.80-1.65 (m, 4H), 1.56 (s, 3H), 0.91 (s, 9H), 0.22-0.13 (m, 6H)

Step 3: Synthesis of Compound 27-C

Except for using the corresponding raw materials, the compound 27-C was prepared using the same method as in the preparation of compound 1-D in Example 1.

MS m/z: 506.8[M+H]$^+$

Step 4: Synthesis of Compound 27-D

Except for using the corresponding raw materials, the compound 27-D was prepared using the same method as in the preparation of compound 1 in Example 1.

MS m/z: 589.6[M+H]$^+$

Step 5: Synthesis of Compound 27

Compound 27-D (110 mg, 186.80 μmol) was dissolved in trifluoroacetic acid (21.30 mg, 186.80 μmol, 13.83 μL), stirred at 60° C. for 1 h, then adjusted with 1 M sodium hydroxide solution to pH=7 to 8, extracted with dichloromethane (150 mL, 50 mL*3), and washed with saturated brine (50 mL). The organic phase was collected, dried over anhydrous sodium sulfate, and concentrated to obtain a crude product, which was separated and purified by preparative high performance liquid chromatography (neutral, mobile phase: acetonitrile-water) to obtain compound 27.

MS m/z: 475.3[M+H]$^+$ $^1$H NMR (400 MHz, CDCl$_3$) δ 8.69 (s, 1H), 8.49 (d, J=2.5 Hz, 1H), 8.22 (d, J=8.8 Hz, 1H), 8.06 (d, J=1.8 Hz, 1H), 7.89 (dd, J=2.5, 8.5 Hz, 1H), 7.79 (dd, J=2.0, 8.8 Hz, 1H), 6.89 (d, J=8.5 Hz, 1H), 4.42 (t, J=6.5 Hz, 2H), 3.39 (s, 3H), 2.57 (d, J=9.0 Hz, 4H), 2.51-2.45 (m, 2H), 2.28 (s, 6H), 2.04-1.96 (m, 2H), 1.87-1.75 (m, 4H), 1.58 (s, 3H)

Example 28: Compound 28

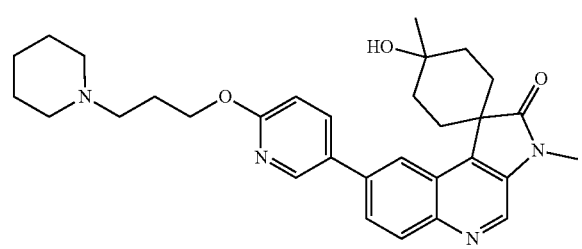 [SMILES: CN1C(=O)C2(CCC(C)(O)CC2)c2c1cnc1ccc(-c3ccc(OCCCN4CCCCC4)nc3)cc21]

Synthetic Route

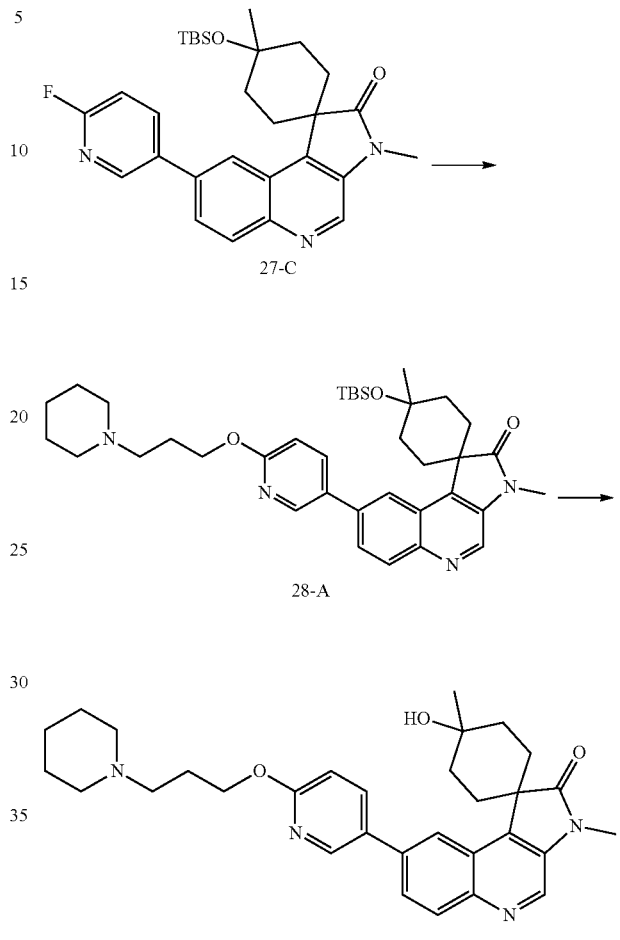

Step 1: Synthesis of Compound 28-A

Except for using the corresponding raw materials, the compound 28-A was prepared using the same method as in the preparation of compound 1 in Example 1.

MS m/z: 629.6[M+H]$^+$

Step 2: Synthesis of Compound 28

Except for using the corresponding raw materials, the compound 28 was prepared using the same method as in the preparation of compound 27 in Example 27.

MS m/z: 515.4[M+H]$^+$ $^1$H NMR (400 MHz, CDCl$_3$) δ 8.69 (s, 1H), 8.49 (d, J=2.8 Hz, 1H), 8.22 (d, J=8.8 Hz, 1H), 8.05 (d, J=1.5 Hz, 1H), 7.89 (dd, J=2.5, 8.5 Hz, 1H), 7.79 (dd, J=2.0, 8.8 Hz, 1H), 6.89 (d, J=8.5 Hz, 1H), 4.41 (t, J=6.5 Hz, 2H), 3.39 (s, 3H), 2.57 (d, J=9.3 Hz, 2H), 2.50 (br d, J=8.0 Hz, 2H), 2.43 (br s, 2H), 2.09-1.97 (m, 2H), 1.84 (br d, J=8.5 Hz, 2H), 1.78 (br d, J=7.8 Hz, 2H), 1.59 (br s, 8H), 1.57 (br s, 3H), 1.45 (br s, 2H)

Example 29: Compound 29

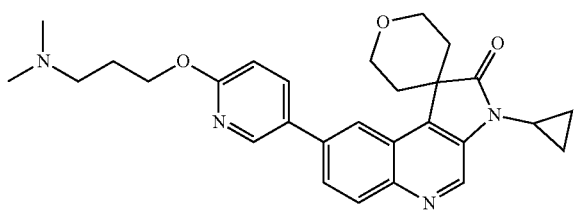 [SMILES: CN(C)CCCOc1ccc(-c2ccc3ncc4c(c3c2)C2(CCOCC2)C(=O)N4C2CC2)cn1]

Synthetic Route

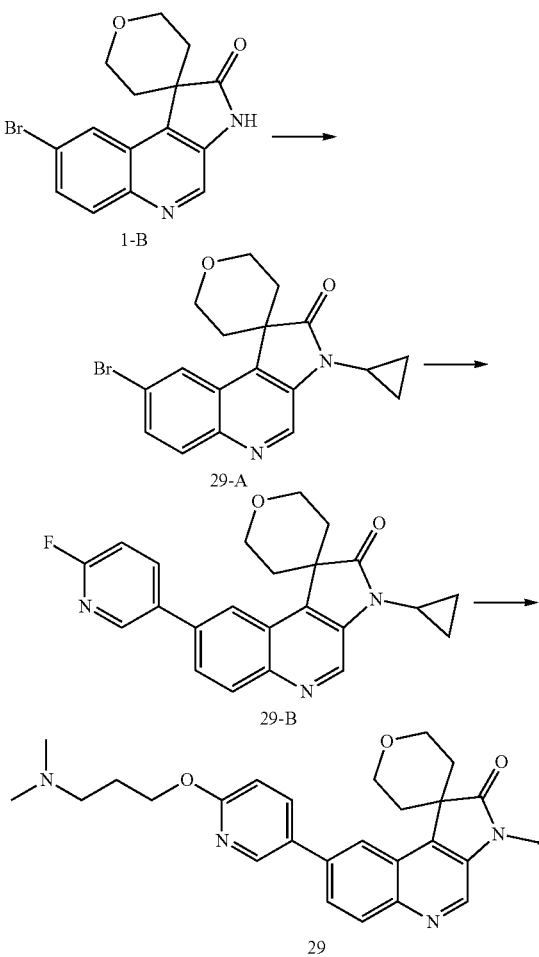

Step 1: Synthesis of Compound 29-A

Compound 1-B (200 mg, 600.28 μmol) was dissolved in anhydrous toluene (15 mL), and cyclopropylboronic acid (103.12 mg, 1.20 mmol), sodium carbonate (127.25 mg, 1.20 mmol), copper acetate (109.03 mg, 600.28 μmol) and pyridine (94.96 mg, 1.20 mmol, 96.90 L) were added. The mixed system was stirred for 12 h at 70° C., and then filtered. The filtrate was collected, and concentrated to obtain a crude product, which was separated and purified by chromatography column (dichloromethane/tetrahydrofuran=1/0 to 10/1) to obtain compound 29-A.

MS m/z: 373.0[M+H]$^+$ $^1$H NMR (400 MHz, CDCl$_3$) δ 8.95 (s, 1H), 8.22 (d, J=1.5 Hz, 1H), 8.01 (d, J=9.0 Hz, 1H), 7.67 (dd, J=2.0, 9.0 Hz, 1H), 4.50-4.35 (m, 2H), 4.03-3.91 (m, 2H), 2.80 (tt, J=3.6, 7.0 Hz, 1H), 2.64 (dt, J=5.4, 13.5 Hz, 2H), 1.64 (s, 2H), 1.23-1.15 (m, 2H), 1.01-0.93 (m, 2H)

Step 2: Synthesis of Compound 29-B

Except for using the corresponding raw materials, the compound 29-B was prepared using the same method as in the preparation of compound 1-D in Example 1.

MS m/z: 390.1[M+H]$^+$ $^1$H NMR (400 MHz, CDCl$_3$) δ 8.99 (s, 1H), 8.55 (d, J=1.8 Hz, 1H), 8.26 (d, J=8.8 Hz, 1H), 8.17 (d, J=1.0 Hz, 1H), 8.11 (dt, J=2.5, 7.9 Hz, 1H), 7.85-7.75 (m, 1H), 7.11 (dd, J=2.9, 8.4 Hz, 1H), 4.47 (br t, J=11.3 Hz, 2H), 3.98 (dd, J=5.0, 11.8 Hz, 2H), 2.83 (tt, J=3.7, 6.9 Hz, 1H), 2.71 (dt, J=5.3, 13.4 Hz, 2H), 1.70 (br s, 2H), 1.28-1.16 (m, 2H), 1.05-0.90 (m, 2H)

Step 3: Synthesis of Compound 29

Except for using the corresponding raw materials, the compound 29 was prepared using the same method as in the preparation of compound 1 in Example 1.

MS m/z: 473.3[M+H]$^+$ $^1$H NMR (400 MHz, CDCl$_3$) δ 8.95 (s, 1H), 8.50 (d, J=2.5 Hz, 1H), 8.21 (d, J=8.8 Hz, 1H), 8.15 (d, J=1.8 Hz, 1H), 7.92 (dd, J=2.5, 8.5 Hz, 1H), 7.79 (dd, J=1.8, 8.8 Hz, 1H), 6.89 (d, J=8.5 Hz, 1H), 4.51-4.42 (m, 4H), 3.97 (dd, J=4.9, 11.7 Hz, 2H), 2.82 (td, J=3.3, 6.9 Hz, 1H), 2.73 (dt, J=5.3, 13.7 Hz, 2H), 2.64 (br s, 2H), 2.40 (s, 6H), 2.14-2.05 (m, 2H), 1.67 (br d, J=14.1 Hz, 2H), 1.21 (q, J=6.8 Hz, 2H), 1.02-0.96 (m, 2H)

Example 30: Compound 30

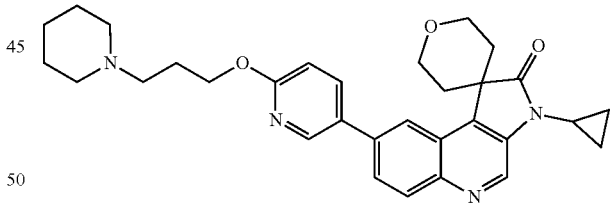

Synthetic Route

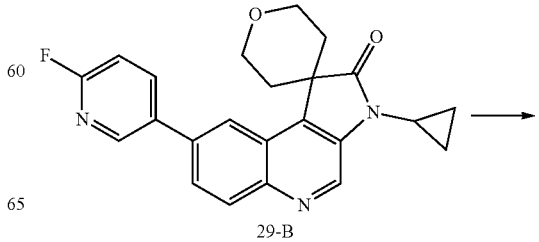

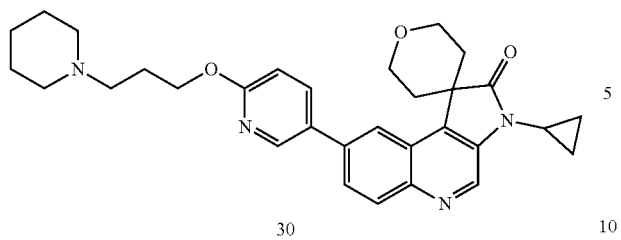

30

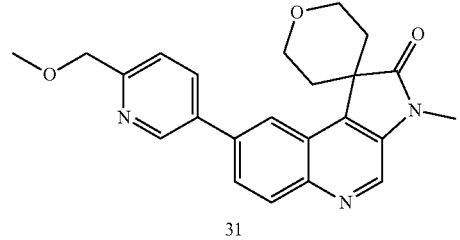

31

Step 1: Synthesis of Compound 30

Except for using the corresponding raw materials, the compound 30 was prepared using the same method as in the preparation of compound 1 in Example 1.

MS m/z: 513.2[M+H]+

¹H NMR (400 MHz, CDCl₃) δ 8.95 (s, 1H), 8.50 (d, J=2.5 Hz, 1H), 8.21 (d, J=9.0 Hz, 1H), 8.15 (d, J=1.5 Hz, 1H), 7.92 (dd, J=2.6, 8.7 Hz, 1H), 7.79 (dd, J=1.9, 8.9 Hz, 1H), 6.88 (d, J=8.5 Hz, 1H), 4.51-4.39 (m, 4H), 3.97 (dd, J=4.9, 11.7 Hz, 2H), 2.82 (tt, J=3.5, 7.0 Hz, 1H), 2.73 (dt, J=5.3, 13.4 Hz, 2H), 2.55-2.48 (m, 2H), 2.43 (br s, 2H), 2.12-1.98 (m, 2H), 1.68 (br s, 4H), 1.63-1.56 (m, 4H), 1.45 (br d, J=5.3 Hz, 2H), 1.26-1.14 (m, 2H), 1.08-0.90 (m, 2H)

Example 31: Compound 31

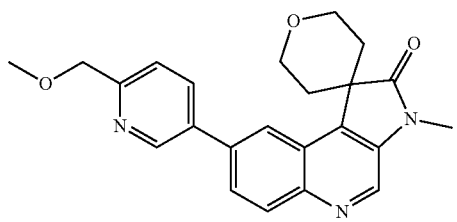

Synthetic Route

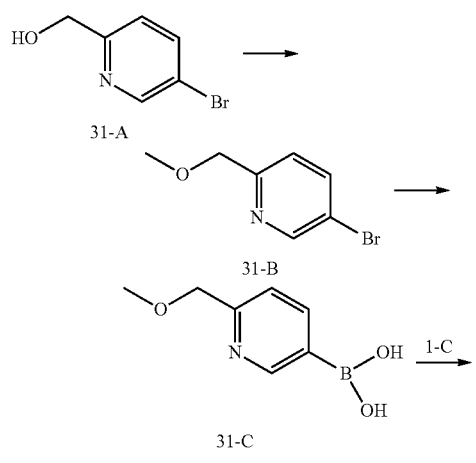

Step 1: Synthesis of Compound 31-B

At 0° C. and under nitrogen protection, compound 31-A (5 g, 26.59 mmol) was added slowly to a solution of sodium hydride (1.60 g, 39.89 mmol, 60% purity) in THF (20 mL). The reaction solution was stirred at 25° C. for 0.5 h, and then a solution of iodomethane (5.66 g, 39.89 mmol, 2.48 mL) in THF (10 mL) was added slowly at 0° C. The reaction solution was stirred at 20° C. for 12 h. At 20° C., the reaction solution was quenched with water (20 mL), diluted by adding water (10 mL), and extracted with EtOAc (150 mL, 50 mL*3). The organic phase was combined, washed with saturated sodium chloride (150 mL, 50 mL*3), dried over anhydrous sodium sulfate, filtered, and concentrated to obtain a crude product, The residue was purified by column chromatography (0 to 10% EtOAc/PE) to obtain 31-B.

MS m/z: 201.8[M+H]+

¹H NMR (400 MHz, CDCl₃) δ 8.61 (d, J=2.0 Hz, 1H), 7.82 (dd, J=2.3, 8.5 Hz, 1H), 7.33 (d, J=8.3 Hz, 1H), 4.53 (s, 2H), 3.47 (s, 3H)

Step 2: Synthesis of Compound 31-C

Under nitrogen protection, a mixed solution of 31-B (4.8 g, 23.76 mmol), bis(pinacolato)diboron (6.64 g, 26.13 mmol), potassium acetate (6.99 g, 71.27 mmol) and Pd(dppf)Cl₂ (1.74 g, 2.38 mmol) in dioxane (40 mL) and water (8 mL) was stirred at 100° C. for 12 h. The reaction solution was filtered, and the filtrate was concentrated to obtain a residue, which was separated and purified by preparative thin-layer chromatography silica gel plate to obtain compound 31-C.

MS m/z: 167.9[M+H]+

¹H NMR (400 MHz, DMSO-d₆) δ 8.88 (s, 1H), 8.49 (d, J=7.8 Hz, 1H), 7.73 (d, J=7.8 Hz, 1H), 4.69 (s, 2H), 3.42 (s, 3H).

Step 3: Synthesis of Compound 31

Except for using the corresponding raw materials, the compound 31 was prepared using the same method as in the preparation of compound 1-D in Example 1.

MS m/z: 390.3[M+H]+

¹H NMR (400 MHz, CDCl₃) δ 8.92 (d, J=2.0 Hz, 1H), 8.74 (s, 1H), 8.28-8.19 (m, 2H), 8.03 (dd, J=2.3, 8.0 Hz, 1H), 7.84 (dd, J=2.0, 8.8 Hz, 1H), 7.59 (d, J=8.0 Hz, 1H), 4.69 (s, 2H), 4.56-4.41 (m, 2H), 3.99 (dd, J=4.9, 11.7 Hz, 2H), 3.54 (s, 3H), 3.40 (s, 3H), 2.75 (dt, J=5.3, 13.4 Hz, 2H), 1.71 (br d, J=14.1 Hz, 2H)

Example 32: Compound 32

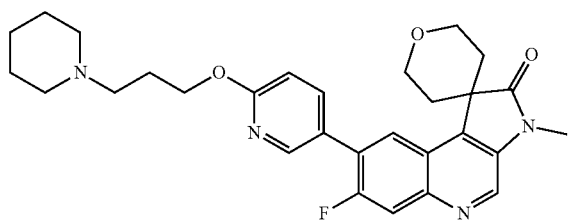 [SMILES: CN1C(=O)C2(CCOCC2)c2c1cnc1cc(F)c(-c3ccc(OCCCN4CCCCC4)nc3)cc21]

Synthetic Route

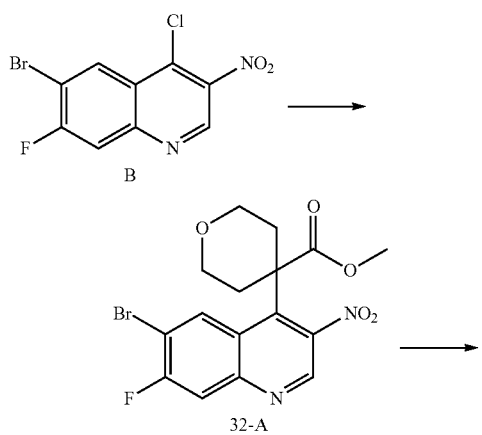

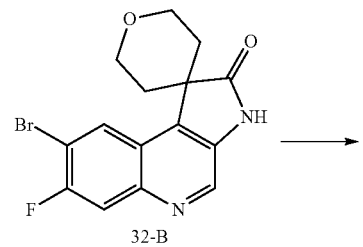

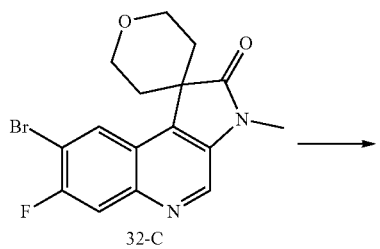

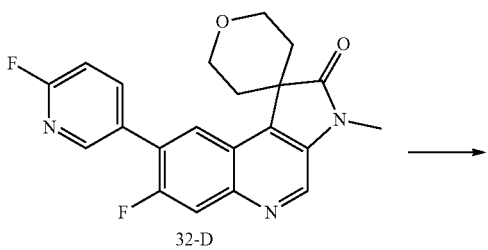

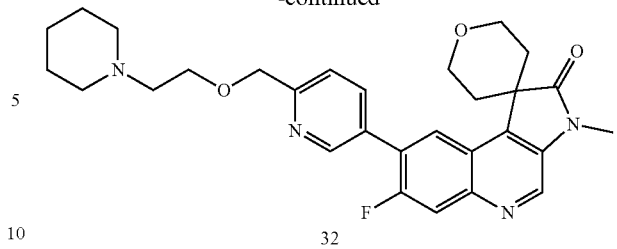

32

Step 1: Synthesis of Compound 32-A

At −60° C. and under nitrogen protection, n-BuLi (2.5 M, 3.93 mL) was added slowly to a solution of DIPA (993.72 mg, 9.82 mmol, 1.39 mL) in THF (10 mL), and the reaction system was stirred for 30 minutes at −30° C., and then a solution of methyl tetrahydropyran-4-carboxylate (1.49 g, 10.31 mmol, 1.38 mL) in THF (10 mL) was added slowly. The reaction system was stirred for 1 h at −65° C., and finally a solution of compound B (1.5 g, 4.91 mmol) in THF (10 mL) was added slowly. The reaction system was stirred at −65° C. for 2 h. After completion of the reaction, the reaction was quenched by adding water (5 mL), and then diluted by adding saturated brine (10 mL), and extracted with EtOAc (30 mL, 10 mL*3). The organic phase was combined, washed with saturated brine (30 mL, 10 mL*3), dried over anhydrous sodium sulfate, and concentrated to obtain residual solids, which were subjected to column chromatography (0 to 5% THF/PE) to obtain 32-A.

MS m/z: 412.8[M+H]$^+$

Step 2: Synthesis of Compound 32-B

Under nitrogen protection, a zinc powder (1.14 g, 17.43 mmol) was added to a solution of 32-A (720 mg, 1.74 mmol) and NH$_4$Cl (932.10 mg, 17.43 mmol, 609.22 μL) in THF (10 mL) and H$_2$O (10 mL), and the reaction system was stirred at 70° C. for 3 h. After completion of the reaction, the reaction system was filtered, and the filtrate was concentrated to obtain residual solids. The solids were slurried with water (20 mL) for 30 minutes to obtain 32-B.

MS m/z: 350.9[M+H]$^+$

Step 3: Synthesis of Compound 32-C

Under nitrogen protection, a solution of iodomethane (347.68 mg, 2.45 mmol, 152.49 L) in dichloromethane (10 mL) was added to a solution of 32-B (500 mg, 1.07 mmol), TBAB (34.33 mg, 106.50 μmol) and NaOH (63.90 mg, 1.60 mmol) in DCM (10 mL) and H$_2$O (10 mL), and the reaction system was stirred at 30° C. for 1 h. After completion of the reaction, the reaction system was filtered, and the filtrate was concentrated to obtain residual solids. The residual solids were slurried with water (20 mL) for 30 minutes to obtain 32-C.

MS m/z: 364.9[M+H]$^+$

Step 4: Synthesis of Compound 32-D

Under nitrogen protection, a solution of 32-C (200 mg, 547.65 μmol), 2-fluoropyridine-5-boracic acid (154.34 mg, 1.10 mmol), Na$_2$CO$_3$ (116.09 mg, 1.10 mmol), Pd$_2$(dba)$_3$ (50.15 mg, 54.77 μmol) and Xphos (50.15 mg, 54.77 μmol) in dioxane (18 mL) and water (2 mL) was stirred at 100° C.

for 2 h. The reaction mixed solution was concentrated to obtain residual solids, and the solids were subjected to column chromatography (0 to 50% EtOAc/PE) to obtain compound 32-D.

MS m/z: 382.0[M+H]+

Step 5: Synthesis of Compound 32

At 20° C. and under nitrogen protection, 32-D (100 mg, 262.21 μmol) was added to a solution of 1-piperidinepropanol (75.11 mg, 524.42 μmol, 28.71 μL) and NaH (41.95 mg, 1.05 mmol, 60% purity) in DMF (10 mL), and the reaction system was stirred at 70° C. for 2 h. After completion of the reaction, the reaction was quenched by adding water (2 mL), and concentrated to obtain the residual solids. The solids was separated by column chromatography (0 to 10% MeOH/DCM) and preparative HPLC (column: Boston Prime C18 150×30 mm 5 m; mobile phase: [water (0.05% ammonium hydroxide v/v)-acetonitrile]; acetonitrile B %: 50%-80%, 8 min) to obtain compound 32.

MS m/z: 505.3[M+H]+

$^1$H NMR (400 MHz, CDCl$_3$) δ 8.71 (s, 1H), 8.42 (s, 1H), 8.07 (d, J=8.0 Hz, 1H), 7.93-7.84 (m, 2H), 6.89 (d, J=8.8 Hz, 1H), 4.56-4.34 (m, 4H), 3.97 (dd, J=4.8, 11.5 Hz, 2H), 3.39 (s, 3H), 2.78-2.60 (m, 2H), 2.52 (br s, 2H), 2.50-2.33 (m, 4H), 2.10-1.99 (m, 2H), 1.69 (br d, J=14.3 Hz, 2H), 1.60 (br s, 4H), 1.50-1.40 (m, 2H)

Example 33: Compound 33

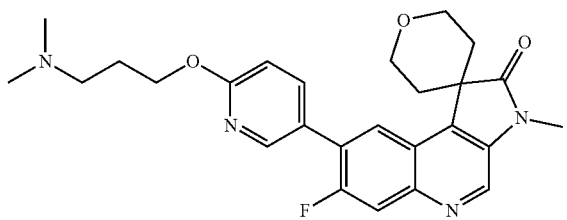

Synthetic Route

Step 1: Synthesis of Compound 33

Except for using the corresponding raw materials, the compound 33 was prepared using the same method as in the preparation of compound 1 in Example 1.

MS m/z: 465.2[M+H]+

$^1$H NMR (400 MHz, CDCl$_3$) δ 8.64 (s, 1H), 8.37-8.32 (m, 1H), 7.99 (d, J=8.0 Hz, 1H), 7.85-7.77 (m, 2H), 6.82 (d, J=8.5 Hz, 1H), 4.45-4.35 (m, 4H), 3.90 (dd, J=4.9, 11.7 Hz, 2H), 3.32 (s, 3H), 2.69-2.54 (m, 4H), 2.34 (s, 6H), 2.11-1.97 (m, 2H), 1.63 (br d, J=14.1 Hz, 2H)

Example 34: Compound 34

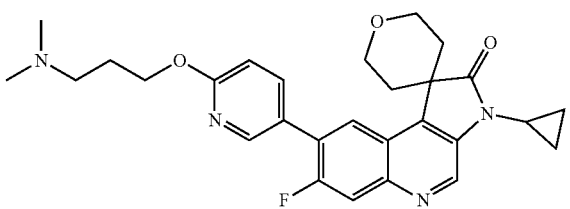 [SMILES: CN(C)CCCOc1ccc(-c2cc3c4c(cnc3cc2F)N(C2CC2)C(=O)C42CCOCC2)cn1]

Synthetic Route

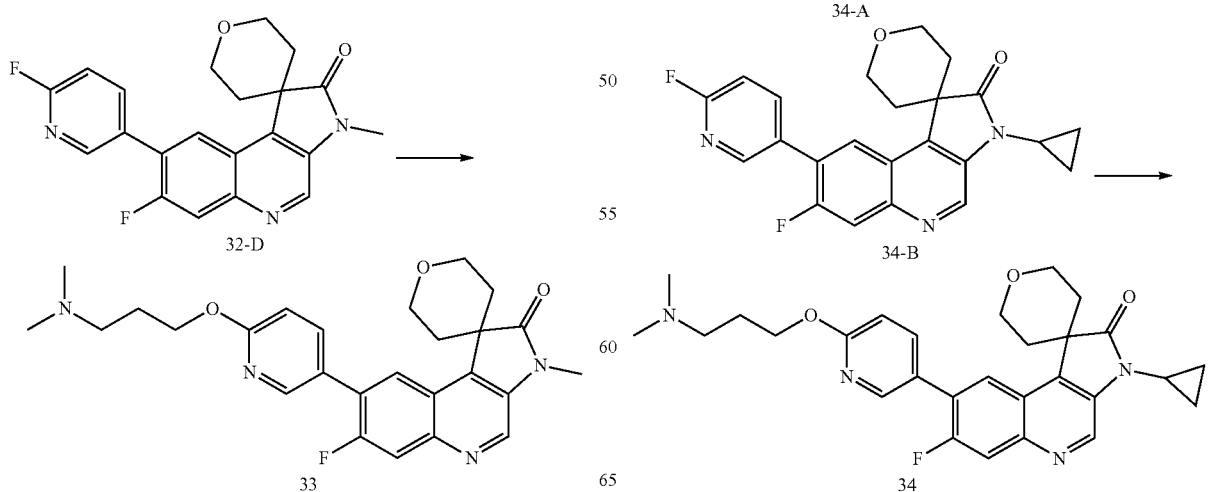

Step 1: Synthesis of Compound 34-A

Except for using the corresponding raw materials, the compound 34-A was prepared using the same method as in the preparation of compound 29-A in Example 29.

$^1$H NMR (400 MHz, CDCl$_3$) δ 8.95 (s, 1H), 8.31 (d, J=7.3 Hz, 1H), 7.84 (d, J=9.5 Hz, 1H), 4.50-4.37 (m, 2H), 3.98 (dd, J=5.0, 11.8 Hz, 2H), 2.84-2.72 (m, 1H), 2.66-2.52 (m, 2H), 1.62 (s, 2H), 0.98-0.94 (m, 2H), 0.90-0.86 (m, 2H)

Step 2: Synthesis of Compound 34-B

Except for using the corresponding raw materials, the compound 34-B was prepared using the same method as in the preparation of compound 1-D in Example 1.

MS m/z: 408.1[M+H]$^+$ $^1$H NMR (400 MHz, CDCl$_3$) δ 8.92 (s, 1H), 8.42 (s, 1H), 8.01 (d, J=8.0 Hz, 2H), 7.86 (d, J=11.4 Hz, 1H), 7.05 (dd, J=2.9, 8.4 Hz, 1H), 4.38 (dt, J=1.9, 12.1 Hz, 2H), 3.89 (dd, J=5.1, 11.7 Hz, 2H), 2.75 (s, 1H), 2.56 (br d, J=4.6 Hz, 2H), 1.63 (s, 1H), 1.61-1.59 (m, 1H), 1.17-1.11 (m, 2H), 0.96-0.89 (m, 2H)

Step 3: Synthesis of Compound 34

Except for using the corresponding raw materials, the compound 34 was prepared using the same method as in the preparation of compound 1 in Example 1.

MS m/z: 491.3[M+H]$^+$ $^1$H NMR (400 MHz, CDCl$_3$) δ 8.97 (s, 1H), 8.43 (s, 1H), 8.07 (d, J=8.0 Hz, 1H), 7.96-7.85 (m, 2H), 6.91 (d, J=8.5 Hz, 1H), 4.46 (br t, J=6.4 Hz, 4H), 4.03-3.92 (m, 2H), 2.90-2.79 (m, 1H), 2.72-2.62 (m, 2H), 2.56-2.49 (m, 2H), 2.31 (s, 6H), 2.07-2.01 (m, 2H), 1.71-1.66 (m, 2H), 1.26-1.20 (m, 2H), 1.05-0.97 (m, 2H)

Example 35: Compound 35

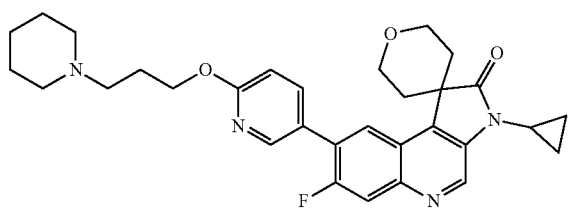 [SMILES: O=C1N(C2CC2)c2cnc3cc(F)c(-c4ccc(OCCCN5CCCCC5)nc4)cc3c2C12CCOCC2]

Synthetic Route

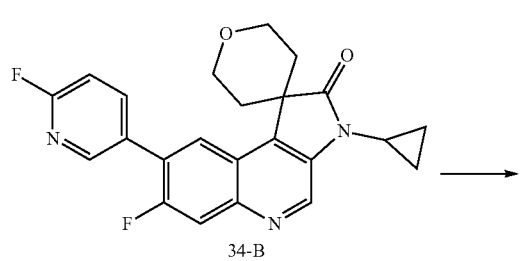

34-B

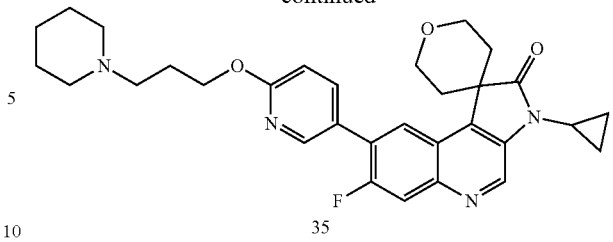

35

Step 1: Synthesis of Compound 35

Except for using the corresponding raw materials, the compound 35 was prepared using the same method as in the preparation of compound 1 in Example 1.

MS m/z: 531.4[M+H]$^+$ $^1$H NMR (400 MHz, CDCl$_3$) δ 8.97 (s, 1H), 8.43 (s, 1H), 8.07 (d, J=8.1 Hz, 1H), 7.95-7.85 (m, 2H), 6.91 (d, J=8.6 Hz, 1H), 4.45 (br d, J=6.8 Hz, 4H), 4.04-3.94 (m, 2H), 2.88-2.80 (m, 1H), 2.72-2.61 (m, 2H), 2.57-2.51 (m, 2H), 2.50-2.33 (m, 4H), 2.11-2.03 (m, 2H), 1.72-1.66 (m, 6H), 1.47 (br s, 2H), 1.26-1.20 (m, 2H), 1.05-0.98 (m, 2H)

Example 36: Compound 36

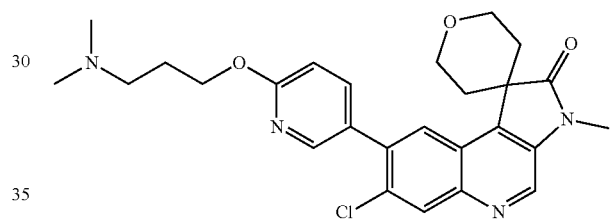

Synthetic Route

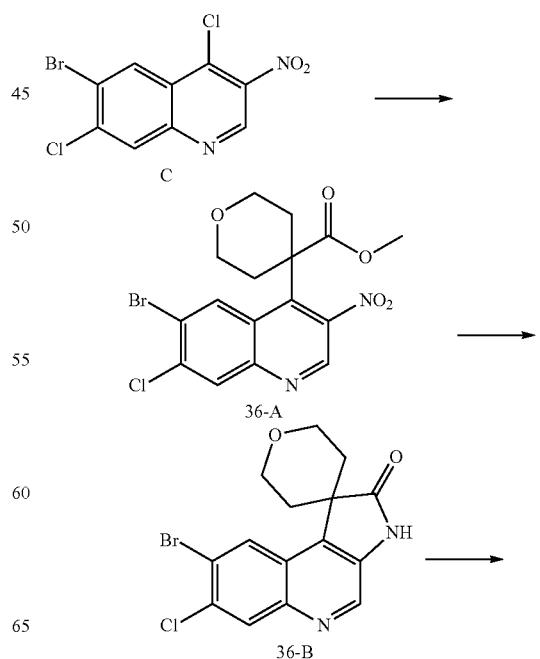

C

36-A

36-B

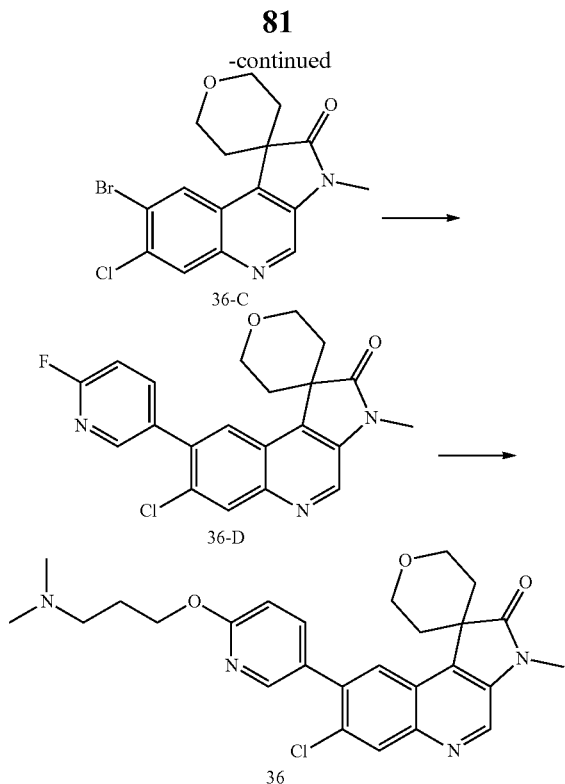

Step 1: Synthesis of Compound 36-A

Except for using the corresponding raw materials, the compound 36-A was prepared using the same method as in the preparation of compound 1-A in Example 1.
MS m/z: 429.0[M+H]⁺

Step 2: Synthesis of Compound 36-B

Except for using the corresponding raw materials, the compound 36-B was prepared using the same method as in the preparation of compound 1-B in Example 1.
MS m/z: 366.9[M+H]⁺

Step 3: Synthesis of Compound 36-C

Except for using the corresponding raw materials, the compound 36-C was prepared using the same method as in the preparation of compound 1-C in Example 1.
MS m/z: 381.0[M+H]⁺

Step 4: Synthesis of Compound 36-D

Except for using the corresponding raw materials, the compound 36-D was prepared using the same method as in the preparation of compound 1-D in Example 1.
MS m/z: 398.0[M+H]⁺
$^1$H NMR (400 MHz, CDCl$_3$) δ 8.76 (s, 1H), 8.36 (d, J=2.3 Hz, 1H), 8.32 (s, 1H), 8.01 (s, 1H), 8.00-7.94 (m, 1H), 7.10 (dd, J=2.8, 8.3 Hz, 1H), 4.50-4.39 (m, 2H), 3.95 (dd, J=5.0, 11.8 Hz, 2H), 3.40 (s, 3H), 2.61 (dt, J=5.3, 13.4 Hz, 2H), 1.68 (br d, J=14.6 Hz, 2H)

Step 5: Synthesis of Compound 36

Except for using the corresponding raw materials, the compound 36 was prepared using the same method as in the preparation of compound 1 in Example 1.

MS m/z: 481.3[M+H]⁺
$^1$H NMR (400 MHz, CDCl$_3$) δ 8.66 (s, 1H), 8.27-8.17 (m, 2H), 7.93 (s, 1H), 7.73 (dd, J=2.5, 8.5 Hz, 1H), 6.80 (d, J=8.5 Hz, 1H), 4.45-4.33 (m, 4H), 3.88 (dd, J=4.9, 11.7 Hz, 2H), 3.33 (s, 3H), 2.75-2.65 (m, 2H), 2.57 (dt, J=5.3, 13.3 Hz, 2H), 2.43 (s, 6H), 2.16-2.06 (m, 2H), 1.61 (br d, J=13.8 Hz, 2H)

Biological Evaluation

Experimental Example 1: In Vitro Evaluation

The compounds of the present disclosure used for experiments are all prepared in-house, and their chemical names and structural formulas are shown in the preparation examples of each compound. The experimental tests were carried out by a UK company Eurofins, and the experimental results were provided by the company. The following experimental processes were also provided by the company.

Experiment Process of ATM Enzyme Activity Test

Human-derived ATM kinase was incubated in a buffer solution containing 30 nM of GST-cMyc-p53 and Mg/ATP. The concentration of Mg/ATP was determined according to different needs. The reaction was initiated by adding a Mg/ATP complex. After incubating for about 30 minutes at room temperature, a stop solution containing EDTA was added to stop the reaction. Finally, for phosphorylated p53, a detection buffer containing a d2-labeled anti-GST monoclonal antibody and an europium-labeled phosphorylated Ser15 antibody was added. Then time-resolved fluorescence mode was used to read a detection disk, and a homogeneous time-resolved fluorescence (HTRF) signal was obtained by calculating formula HTRF=10000×(Em665 nm/Em620 nm).

Experiment Process of DNA-PK Enzyme Activity Test

Human-derived DNA-PK kinase was incubated in a buffer solution containing 50 nM of GST-cMyc-p53 and Mg/ATP. The concentration of Mg/ATP was determined according to different needs. The reaction was initiated by adding a Mg/ATP complex. After incubating for about 30 minutes at room temperature, a stop solution containing EDTA was added to stop the reaction. Finally, for phosphorylated p53, a detection buffer containing a d2-labeled anti-GST monoclonal antibody and an europium-labeled phosphorylated Ser15 antibody was added. Then time-resolved fluorescence mode was used to read a detection disk, and a homogeneous time-resolved fluorescence (HTRF) signal was obtained by calculating formula HTRF=10000× (Em665 nm/Em620 nm).

TABLE 1

In vitro cell activity determination results (IC$_{50}$) of the compounds of the present disclosure

| Compound No. | ATM (IC50 nM) | DNA-PK (IC50 nM) |
|---|---|---|
| AZD0156 | 1 | 58 |
| Example 1 | 0.9 | 78 |
| Example 2 | 288 | 73 |
| Example 3 | 1 | 48 |
| Example 4 | 1 | 62 |

TABLE 1-continued

In vitro cell activity determination results
($IC_{50}$) of the compounds of the present disclosure

| Compound No. | ATM (IC50 nM) | DNA-PK (IC50 nM) |
|---|---|---|
| Example 5 | 2 | 92 |
| Example 6 | 2 | 800 |
| Example 7 | 1 | 153 |
| Example 8 | 3 | 99 |
| Example 9 | 1 | 83 |
| Example 10 | 2 | 80 |
| Example 11 | 2 | 243 |
| Example 12 | 2 | 26 |
| Example 13 | 4 | 27 |
| Example 14 | 3 | 46 |
| Example 15 | 2 | 41 |
| Example 16 | 4 | 204 |
| Example 17 | 3 | 352 |
| Example 18 | 2 | 343 |
| Example 19 | 0.8 | 77 |
| Example 20 | 2 | 129 |
| Example 21 | 7 | 509 |
| Example 22 | 1 | 14 |
| Example 23 | 0.8 | 30 |
| Example 24 | 2 | 80 |
| Example 25 | 1 | 92 |
| Example 26 | 1 | 76 |
| Example 27 | 1 | 99 |
| Example 28 | 2 | 334 |
| Example 29 | 2 | 269 |
| Example 30 | 2 | 475 |
| Example 31 | 63 | 88 |
| Example 32 | 2 | 561 |
| Example 33 | 1 | 593 |
| Example 34 | 5 | >1000 |
| Example 35 | 3 | >1000 |
| Example 36 | 12 | >1000 |

Conclusion: The compound of the present disclosure has a significant inhibitory effect on ATM kinase and has good selectivity for DNA-PK kinase.

Experimental Example 2

In vivo pharmacodynamic studies of ATM inhibitors and etoposide that act synergistically in female BALB/c nude mouse model with human lung cancer H446 cell subcutaneous xenograft tumor Experiment Object Evaluation of the in vivo efficacy of the test drug ATM inhibitor and etoposide in a BALB/c nude mouse model with human lung cancer H446 cell subcutaneous xenograft tumor via intraperitoneal or oral administration.

Experimental Design

TABLE 2

Experimental animal grouping and dosage regimen for in vivo efficacy of ATM inhibitors and etoposide

| Number of groups (G) | Number of mice per group (N) | Treatment | Dosage (mg/kg) | Route of administration | Frequency and cycle of administration |
|---|---|---|---|---|---|
| 1 | 6 | Vehicle Control | — | PO | QD × 4 W |
| 2 | 6 | etoposide | 15 | IP | BIW × 4 W |
| 3 | 6 | Example 32 | 5 | PO | QD (PG-D0, 3D on, 4D off from PG-D1) × 4 W |
| 4 | 6 | etoposide + example 32 | 15 + 5 | IP + PO | BIW + QD (PG-D0, 3D on, 4D off from PG-D1) × 4 W |
| 5 | 6 | etoposide + AZD0156 | 15 + 5 | IP + PO | BIW + QD (PG-D0, 3D on, 4D off from PG-D1) × 4 W |

Note:

IP: Intraperitoneal injection;

PO: Oral administration;

QD: Once a day;

BIW: Twice a week;

QD (PG-D0, 3D on, 4D off from PG-D1) × 4 W: administration from Tuesday to Thursday, once a day, weekly cycle, for four weeks;

BIW + QD (PG-D0, 3D on, 4D off from GPG-D1) × 4 W: etoposide was administered on Monday, ATM inhibitor was administered from Tuesday to Thursday, once a day, weekly cycle, for four weeks.

Note: IP: Intraperitoneal injection; P0: Oral administration; QD: Once a day; BIW: Twice a week; QD (PG-D0, 3D on, 4D off from PG-D31)×4W: administration from Tuesday to Thursday, once a day, weekly cycle, for four weeks; BIW+QD (PG-D0, 3D on, 4D off from PG-D1)×4 W: etoposide was administered on Monday, ATM inhibitor was administered from Tuesday to Thursday, once a day, weekly cycle, for four weeks.

Experimental Methods and Steps

1. Cell Culture

Human lung cancer cells H446 (ATCC, Manassas, Va., HTB-171) were cultured in a monolayer in vitro. The culture conditions were: RPMI-1640 medium with 10% fetal bovine serum, 100 U/mL penicillin and 100 μg/mL streptomycin, and 37° C. 5% $CO_2$ culture. Conventional digestion treatment with pancreatin-EDTA for passage was carried out twice a week. When the cell saturation was 80% to 90%, the cells were collected, counted and inoculated.

2. Tumor Cell Inoculation 0.2 mL 5×$10^6$ of H446 cells (1:1 plus matrigel) were subcutaneously inoculated on the right back of each nude mouse. The grouping and administration were started when the average tumor volume reached 125 $mm^3$ (Table).

3. Preparation of Tested Samples

TABLE 3

Preparation method of tested samples

| Compound | Compound preparation | Storage conditions |
|---|---|---|
| Vehicle 1 | 45 g of Captisol was taken, 100 mL of water was added, vortexed until clear, and finally water was added to adjust the volume to 150 mL. | Room temperature |
| Vehicle 2 | 50 g of HP-β-CD was taken, 200 mL of water was added, vortexed until clear, and finally water was added to adjust the volume to 500 mL, and PH was adjusted to 6. | Room temperature |
| Etoposide | 13.636 mg of etoposide was weighed, and a stirrer was put. Firstly, 1.8 mL of PEG300 was added, and stirred at 50° C. until a clear solution, and then 0.9 mL of Solutol HS15 (thawing Solutol at 50° C.) was added and stirred at 50° C. until a clear solution. 6.3 mL of 20% HP-β-CD prepared with 50 mM of phosphate buffer (pH = 6.8) was added and stirred at room temperature until a clear solution. | 4° C. |
| Example 32 | 5.4 mg of Example 32 was weighed, firstly 0.54 mL of DMSO was added, and stirred until a clear solution, and then 4.86 mL of Vehicle 1 was added and stirred until a clear solution, and PH was adjusted to 4-6. | 4° C. |
| AZD0156 | 2.735 mg of AZD0156 was weighed, firstly 0.54 mL of DMSO was added, and stirred until a clear solution, and then 4.86 mL of Vehicle 1 was added and stirred until clear. PH was adjusted to 4-6. | 4° C. |

Note:
Drugs needs to be mixed gently and thoroughly before administering to animals.

Note: Drugs needs to be mixed gently and thoroughly before administering to animals.

Tumor Measurement and Experimental Index

The experimental index was to investigate whether the tumor growth was inhibited, delayed or cured. Tumor diameter was measured twice a week with a vernier caliper. The calculation formula of tumor volume: $V=0.5a \times b^2$, wherein a and b represented the long and short diameters of the tumor, respectively.

The tumor suppressive effect of the compounds uses TGI (0%). TGI (0%) reflected the tumor growth inhibition rate. Calculation of TGI (0%): TGI (0%)=[1−(average tumor volume at the end of administration in a treatment group−average tumor volume at the beginning of administration in this treatment group)/(average tumor volume at the end of administration in the solvent control group−average tumor volume at the beginning of administration in the solvent control group)]×10000.

Tumor proliferation rate T/C (%): wherein T is the average tumor volume obtained from the last measurement (PG-D26) of the treatment group, and C is the average tumor volume obtained from the last measurement (PG-D26) of the control group.

Statistical Analysis

Mean value and standard error (SEM) of the tumor volume of each group at each time point were included (specific data is shown in tables). The treatment group showed the best treatment effect on day 26 after the administration at the end of the test, so the statistical analysis was performed based on this data to evaluate the differences between the groups. The comparison between two groups was analyzed by T-test, and the comparison between three or more groups was analyzed by one-way ANOVA. If there was heterogeneity of variance, the Games-Howell test was applied. If there was homogeneity of variance, the Dunnet (2-sided) test was used for analysis. All data analysis was performed with SPSS 17.0. $p<0.05$ was considered significantly different.

Experimental Results

Mortality, Morbidity, and Weight Changes

The body weight of experimental animals is used as a reference index for indirect determination of drug toxicity. In this model, none of the administration groups showed significant weight loss (FIG. 1). Mice with no. 42161 were found dead on day 15 after administration of the combination group of 15 mg/kg of etoposide and 5 mg/kg of AZD0156. In the treatment group where etoposide was used in combination with Example 32 and AZD0156, respectively, a part of animals lost more than 10% but not less than 15% in body weight. The effect of the test drug ATM inhibitor and etoposide on the body weight of the female BALB/c nude mouse model with H446 cell subcutaneous xenograft tumor was shown in FIG. 1. Relative weight change was calculated based on the weight of an animal at the beginning of administration. The data point represents the percent change in average weight within a group, and the error bar represents standard error (SEM).

Tumor volume

The tumor volume changes in each group after the treatment by administrating the test drug ATM inhibitor and etoposide in female BALB/c nude mouse model with H446 cells subcutaneous xenograft tumor are shown in Table 4.

TABLE 4

Tumor volume at different time points in each group

| After administration Days | Vehicle 1 + Vehicle 2 | Etoposide 15 mg/kg | Example 32 5 mg/kg | Etoposide + example 32 15 + 5 mg/kg | Etoposide + AZD0156 15 + 5 mg/kg |
|---|---|---|---|---|---|
| 0 | 125 ± 7 | 125 ± 8 | 125 ± 7 | 125 ± 7 | 124 ± 7 |
| 3 | 148 ± 10 | 132 ± 11 | 138 ± 6 | 119 ± 18 | 133 ± 8 |
| 7 | 275 ± 21 | 259 ± 37 | 229 ± 10 | 170 ± 29 | 197 ± 26 |
| 10 | 434 ± 40 | 364 ± 47 | 359 ± 36 | 245 ± 40 | 291 ± 29 |
| 14 | 751 ± 61 | 552 ± 66 | 644 ± 83 | 317 ± 59 | 417 ± 36 |
| 17 | 1128 ± 74 | 851 ± 84 | 974 ± 129 | 413 ± 64 | 590 ± 59 |
| 21 | 1798 ± 153 | 1021 ± 112 | 1240 ± 157 | 570 ± 88 | 759 ± 82 |
| 26 | 2782 ± 265 | 1667 ± 193 | 2054 ± 221 | 930 ± 142 | 1344 ± 146 |

Note:
[a] Mean ± SEM.

Note: a. Mean±SEM.

Tumor Growth Curve

Figure 2:
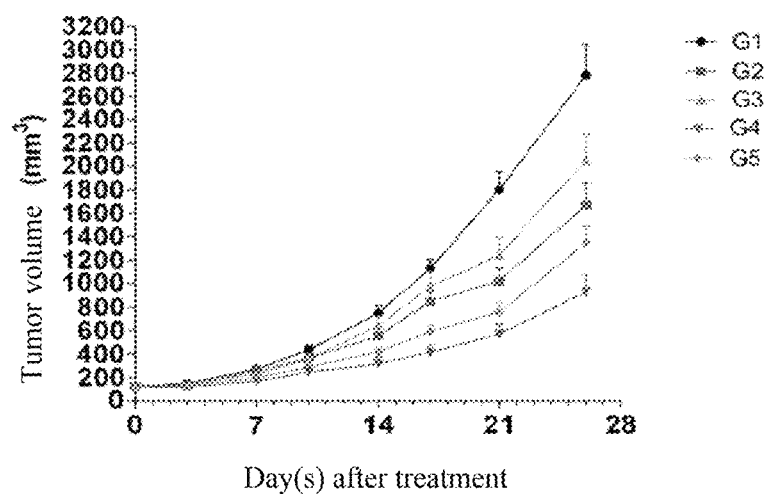
FIG. 2: tumor growth curve.

Tumor growth curve of tumor-bearing mice model with H446 xenograft tumor after administering with the test drug ATM inhibitor and etoposide. Tumor growth curve is shown in FIG. 2. The data point represents mean tumor volume within a group, and the error bar represents standard error (SEM).

Anti-Tumor Efficacy Evaluation Index (Calculated Based on Tumor Volume on Day 26 after Administration)

TABLE 5

Evaluation of tumor suppressive efficacy of test drug ATM inhibitor and etoposide on H446 xenograft tumor model

| Groups | Tumor volume (mm³)[a] (Day 26) | T/C[b] (%) | TGI[b] (%) | p value[c] |
|---|---|---|---|---|
| Vehicle 1 + Vehicle 2 | 2782 ± 265 | — | — | — |
| etoposide, 15 mg/kg | 1667 ± 193 | 59.93 | 41.95 | 0.119 |
| Example 32, 5 mg/kg | 2054 ± 221 | 73.86 | 27.36 | 0.559 |
| Etoposide + example 32, 15 + 5 mg/kg | 930 ± 142 | 33.42 | 69.70 | 0.006 |
| Etoposide + AZD0156, 15 + 5 mg/kg | 1344 ± 146 | 48.30 | 54.17 | 0.028 |

Note:
[a] Mean ± SEM. The animal #42161 in group 5 was found dead on PG-D15, and its data is not counted in statistics.
[b] Tumor growth inhibition was calculated by T/C and TGI (TGI (%) = [1 − (T$_{26}$ − T$_0$)/(V$_{26}$ − V$_0$)] × 100).
[c] The p value was calculated based on the tumor volume.

Note: a. Mean±SEM. The animal #42161 in group 5 was found dead on PG-D15, and its data is not counted in statistics.
b. Tumor growth inhibition was calculated by T/C and TGI (TGI (%)=[1−(T$_{26}$−T0)/(V$_{26}$−V$_0$)]×100).
c. The p value was calculated based on the tumor volume.

Experiment Discussion

In this experiment, we evaluated the in vivo efficacy of the test drug ATM inhibitor and etoposide in the human lung cancer H446 xenograft tumor model. The tumor volume of each group at different time points was shown in Table 4, Table 5 and FIG. 2. 26 days after administration, the tumor volume of tumor-bearing mice in the solvent control group reached 2,782 mm³, and for groups Etoposide+Example 32 (15 mg/kg+5 mg/kg) and Etoposide+AZD0156 (15 mg/kg+5 mg/kg), the average tumor volume was 930 mm³ and 1,344 mm³, respectively, the T/C was 33.42% and 48.30, respectively, the TGI was 69.70% and 54.11%, and the p value was 0.006 and 0.028 compared with the solvent control, respectively.

Experiment Conclusion

In the in vivo efficacy experiment of the ATM inhibitor and etoposide in the human lung cancer H446 xenograft tumor model, the combination of Example 32 and etoposide showed a good synergistic effect, which was better than the efficacy of AZD0156 in combination with etoposide.

What is claimed is:
1. A compound represented by formula (I), an isomer thereof or a pharmaceutically acceptable salt thereof,

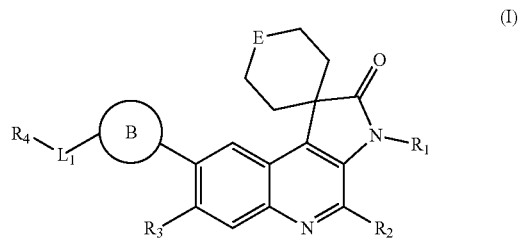

(I)

wherein,
E is selected from —N(R$_5$)—, —O— and —C(R$_6$)(R$_7$)—;
R$_1$ is selected from C$_{1-3}$ alkyl, C$_{1-3}$ alkoxy and C$_{3-6}$ cycloalkyl, wherein the C$_{1-3}$ alkyl, C$_{1-3}$ alkoxy and C$_{3-6}$ cycloalkyl are optionally substituted with 1, 2 or 3 R$_a$;
R$_2$ is selected from H, F, Cl, Br, I, OH and NH$_2$;
R$_3$ is selected from H, F, Cl, Br, I, OH, NH$_2$, CN, C$_{1-3}$ alkyl and C$_{1-3}$ alkoxy, wherein the C$_{1-3}$ alkyl and C$_{1-3}$ alkoxy are optionally substituted with 1, 2 or 3 R$_b$;
R$_4$ is selected from C$_{1-6}$ alkyl and N(R$_c$)(R$_d$);
R$_5$ is selected from H, C$_{1-6}$ alkyl, C$_{3-6}$ cycloalkyl, C$_{1-6}$ alkyl-C=O—, C$_{1-6}$ alkyl-O—C=O— and C$_{3-6}$ cycloalkyl-C=O—, wherein the C$_{1-6}$ alkyl, C$_{3-6}$ cycloalkyl, $C_{1-6}$ alkyl-C=O—, $C_{1-6}$ alkyl-O—C=O— and $C_{3-6}$ cycloalkyl-C=O— are optionally substituted with 1, 2 or 3 $R_e$;

$R_6$ and $R_7$ are each independently selected from H, F, Cl, Br, I, OH, $NH_2$, CN, $C_{1-6}$ alkyl and $C_{1-6}$ alkoxy, wherein the $C_{1-6}$ alkyl or $C_{1-6}$ alkoxy are optionally substituted with 1, 2 or 3 $R_f$;

$L_1$ is selected from a single bond, —$(CH_2)_m$— and —$(CH_2)_m$—O—;

m is selected from 1, 2, 3 and 4;

ring B is selected from phenyl and 5- to 6-membered heteroaryl, wherein the phenyl and 5-to 6-membered heteroaryl are optionally substituted with 1, 2 or 3 $R_g$;

$R_a$ and $R_b$ are each independently selected from F, Cl, Br, I, OH and $NH_2$;

$R_c$ and $R_d$ are each independently selected from H, $C_{1-3}$ alkyl and $C_{3-6}$ cycloalkyl, wherein the $C_{1-3}$ alkyl and $C_{3-6}$ cycloalkyl are each independently selected from 1, 2 or 3 R;

or, $R_c$ and $R_d$ together with the N atom to which they are attached form 4- to 6-membered heterocycloalkyl optionally substituted by 1, 2 or 3 R;

$R_e$, $R_f$ and $R_g$ are each independently selected from F, Cl, Br, I, OH and $NH_2$;

Each R is independently selected from F, Cl, Br, I, OH and $NH_2$;

and the 5- to 6-membered heteroaryl and 4- to 6-membered heterocycloalkyl are each independently comprise 1, 2, 3 or 4 heteroatoms or heteroatom groups independently selected from —NH—, —O—, —S— and N.

2. The compound, isomer thereof or pharmaceutically acceptable salt thereof as defined in claim 1, wherein $R_1$ is selected from $CH_3$, $CH_2CH_3$ and cyclopropyl, and the $CH_3$, $CH_2CH_3$ and cyclopropyl are optionally substituted with 1, 2 or 3 $R_a$.

3. The compound, isomer thereof or pharmaceutically acceptable salt thereof as defined in claim 2, wherein $R_1$ is selected from $CH_3$, $CH_2F$, $CHF_2$, $CF_3$, $CH_2CH_3$ and cyclopropyl.

4. The compound, isomer thereof or pharmaceutically acceptable salt thereof as defined in claim 1, wherein $R_3$ is selected from H, F, Cl, Br, I, OH, $NH_2$, CN, $CH_3$, $CH_2CH_3$ and

and the $CH_3$, $CH_2CH_3$ and

are optionally substituted with 1, 2 or 3 $R_b$.

5. The compound, isomer thereof or pharmaceutically acceptable salt thereof as defined in claim 4, wherein $R_3$ is selected from H, F, Cl, Br, I, OH, $NH_2$, CN, $CH_3$, $CH_2F$, $CHF_2$, $CF_3$, $CH_2CH_3$ and

6. The compound, isomer thereof or pharmaceutically acceptable salt thereof as defined in claim 1, wherein $R_c$ and $R_d$ are each independently selected from $CH_3$, $CH_2CH_3$ and cyclopropyl.

7. The compound, isomer thereof or pharmaceutically acceptable salt thereof as defined in a claim 1, wherein $R_c$ and $R_d$ together with the N atom to which they are attached form pyrrolidyl and piperidinyl, wherein the pyrrolidyl and piperidinyl are optionally substituted with 1, 2 or 3 R.

8. The compound, isomer thereof or pharmaceutically acceptable salt thereof as defined in claim 7, wherein $R_c$ and $R_d$ together with the N atom to which they are attached form

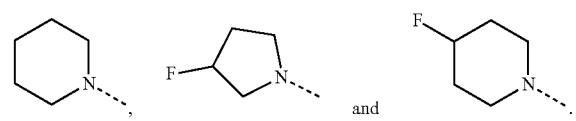

9. The compound, isomer thereof or pharmaceutically acceptable salt thereof as defined in claim 8, wherein $R_4$ is selected from $CH_3$, $CH_2CH_3$,

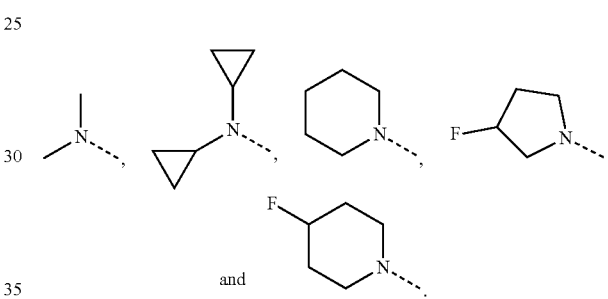

10. The compound, isomer thereof or pharmaceutically acceptable salt thereof as defined in claim 1, wherein $R_5$ is selected from H, $CH_3$, $CH_3CH_2$, $CH(CH_3)_2$, cyclopropyl, $CH_3OC=O$—, $CH(CH_3)_2OC=O$—, $CH_3C=O$—, and cyclopropyl-C=O—, and the $CH_3$, $CH_3CH_2$, $CH(CH_3)_2$, cyclopropyl, $CH_3OC=O$—, $CH(CH_3)_2OC=O$—, $CH_3C=O$—, and cyclopropyl-C=O— are optionally substituted with 1, 2 or 3 $R_e$.

11. The compound, isomer thereof or pharmaceutically acceptable salt thereof as defined in claim 10, wherein $R_5$ is selected from H, $CH_3$, $CH_2F$, $CHF_2$, $CF_3$, $CH_3CH_2$, $CH_2FCH_2$, $CHF_2CH_2$, $CF_3CH_2$, $CH(CH_3)_2$, cyclopropyl, $CH_3OC=O$—, $CH(CH_3)_2OC=O$—, $CH_3C=O$—, and cyclopropyl-C=O—.

12. The compound, isomer thereof or pharmaceutically acceptable salt thereof as defined in claim 1, wherein $R_6$ and $R_7$ are each independently selected from H, F, Cl, Br, I, OH, $NH_2$, CN, $CH_3$, $CH_3CH_2$, $CH(CH_3)_2$ and

and the $CH_3$, $CH_3CH_2$, $CH(CH_3)_2$ and

are optionally substituted with 1, 2 or 3 $R_f$.

13. The compound, isomer thereof or pharmaceutically acceptable salt thereof as defined in claim 12, wherein $R_6$ and $R_7$ are each independently selected from H, F, Cl, Br, I, OH, $NH_2$, CN, $CH_3$, $CH_2F$, $CHF_2$, $CF_3$, $CH_3CH_2$, $CH(CH_3)_2$ and

.

14. The compound, isomer thereof or pharmaceutically acceptable salt thereof as defined in claim 13, wherein E is selected from —O—, —$CF_2$—, —N($CH_3$)—, —NH—,

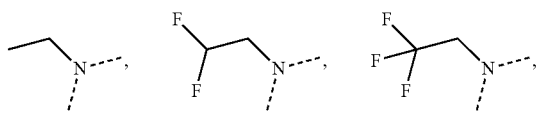

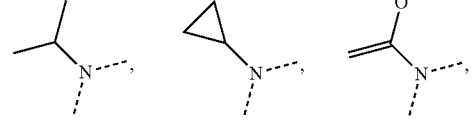

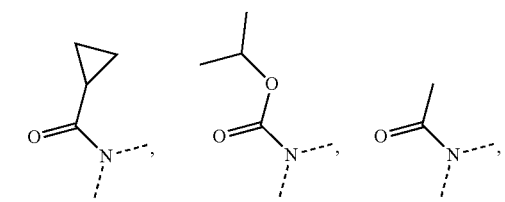

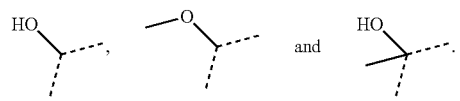

15. The compound, isomer thereof or pharmaceutically acceptable salt thereof as defined in claim 1, wherein Li is selected from a single bond, —($CH_2$)—O— and —($CH_2$)$_3$—O—.

16. The compound, isomer thereof or pharmaceutically acceptable salt thereof as defined in claim 1, wherein ring B is selected from phenyl, pyridyl, pyrazolyl, indazolyl and imidazolyl, and the phenyl, pyridyl, pyrazolyl, indazolyl and imidazolyl are optionally substituted with 1, 2 or 3 $R_g$.

17. The compound, isomer thereof or pharmaceutically acceptable salt thereof as defined in claim 16, wherein ring B is selected from

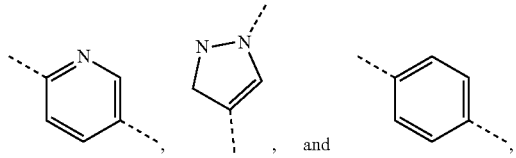

and the

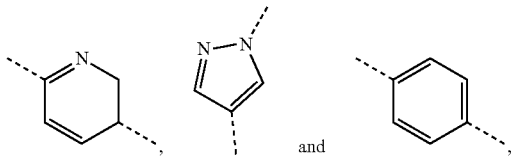

are optionally substituted with 1, 2 or 3 $R_g$.

18. The compound, isomer thereof or pharmaceutically acceptable salt thereof as defined in claim 17, wherein ring B is selected from

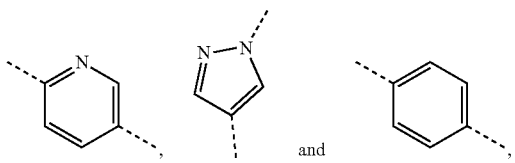

19. The compound, isomer thereof or pharmaceutically acceptable salt thereof as defined in claim 15, wherein $R_4$-$L_1$- is selected from $CH_3$, $CH_3OCH_2$—,

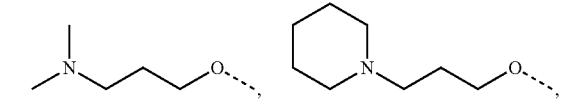

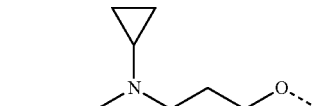

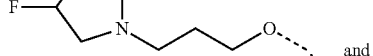

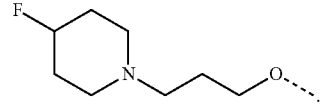

20. The compound, isomer thereof or pharmaceutically acceptable salt thereof as defined in claim 1, selected from (I-1)

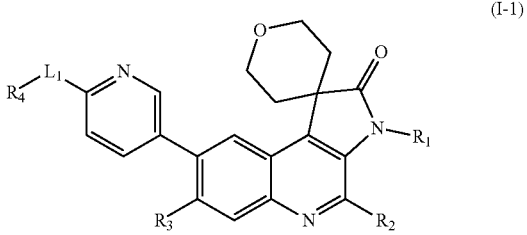

93
-continued
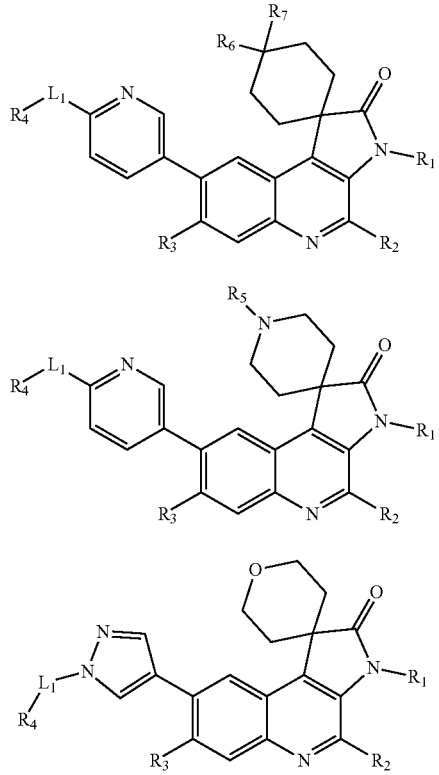
wherein,
$R_1$, $R_2$, $R_3$, $R_4$, $R_5$, $R_6$, $R_7$ and $L_1$ are as defined in claim 1.
21. A compound represented by the following formulas, an isomer thereof or a pharmaceutically acceptable salt thereof, wherein the compound is selected from
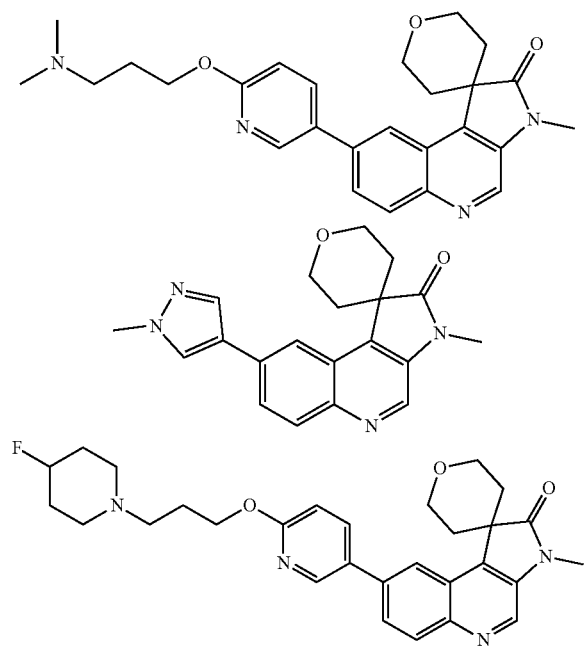
94
-continued
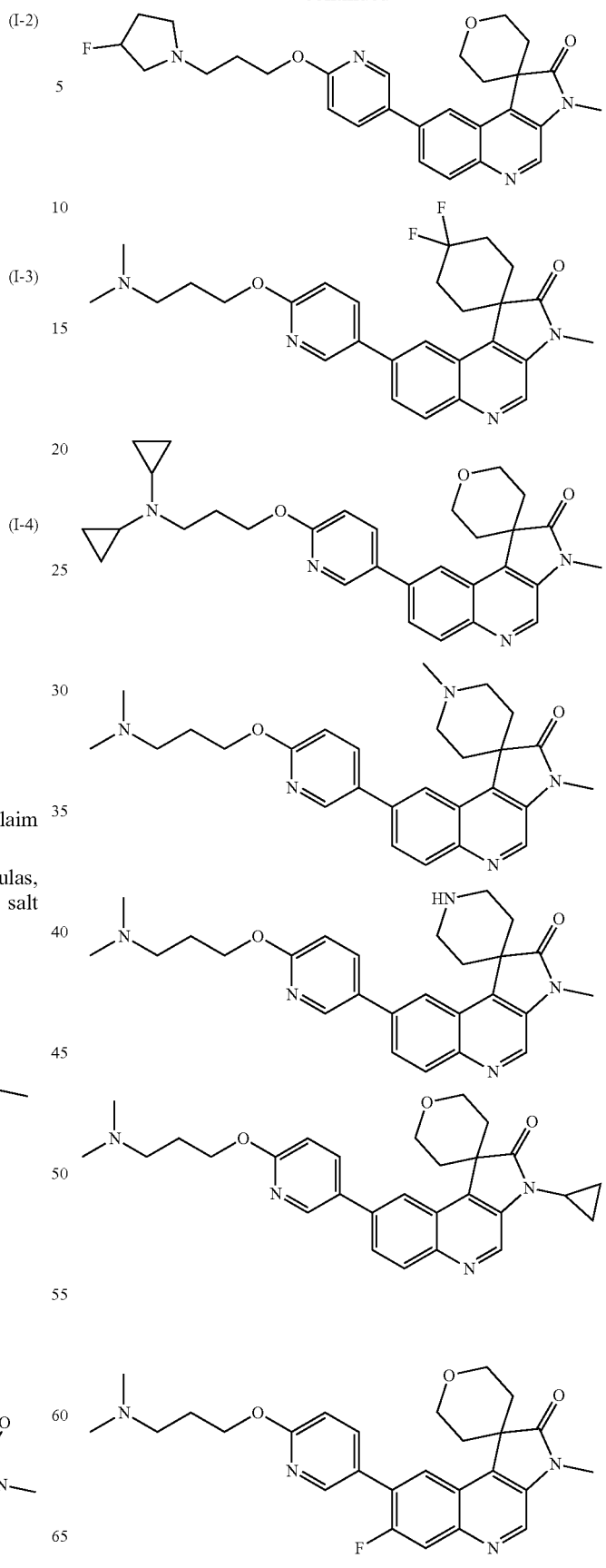

95
-continued
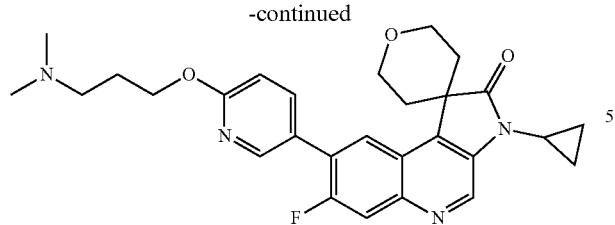
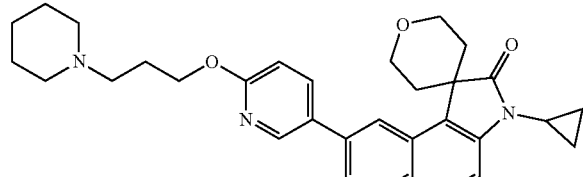
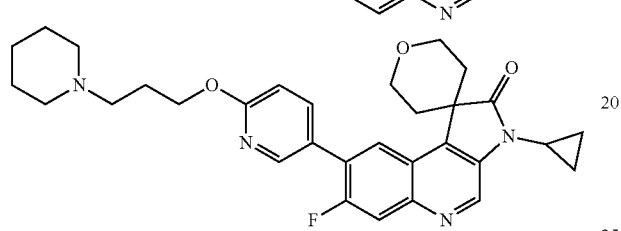
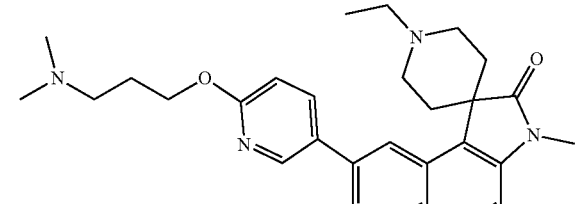
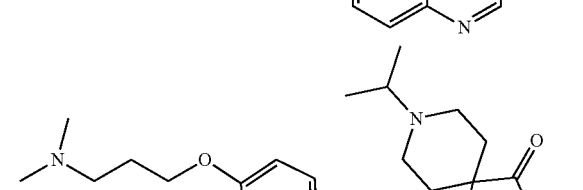
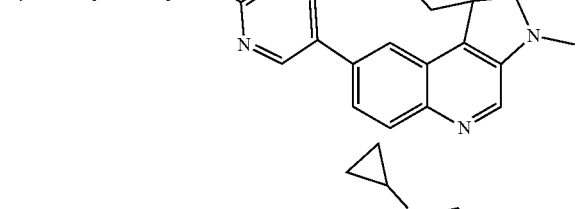
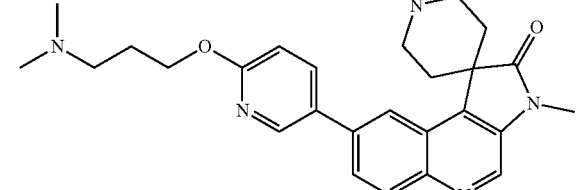
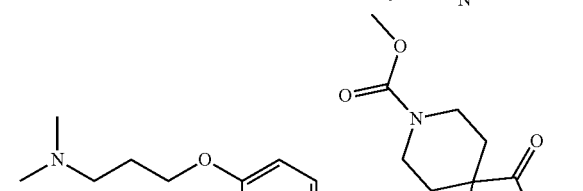
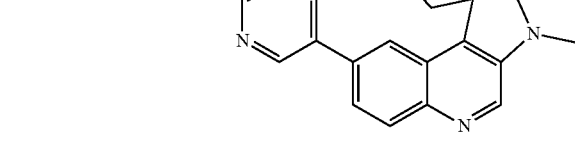
96
-continued
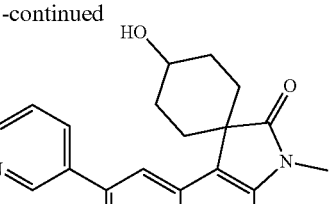
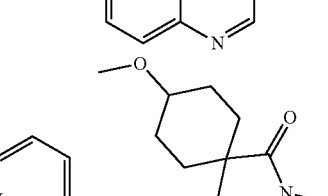
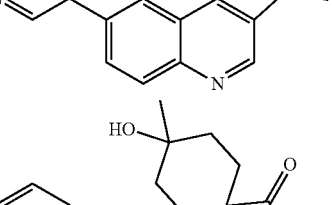
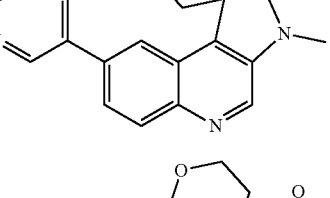
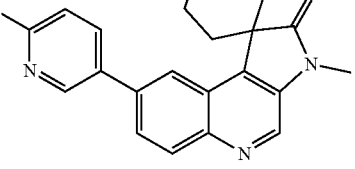
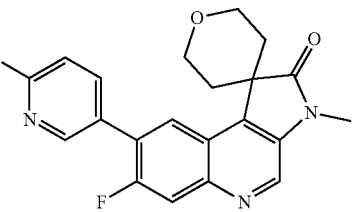
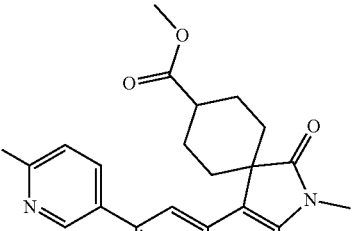
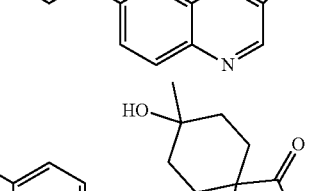
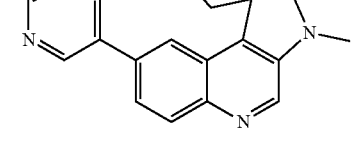

97
-continued
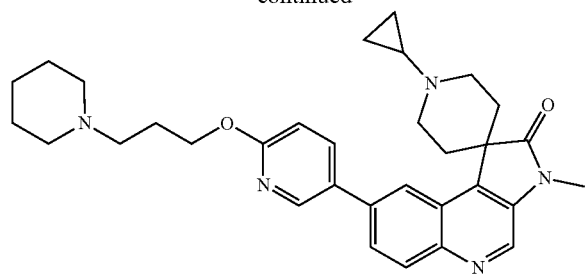
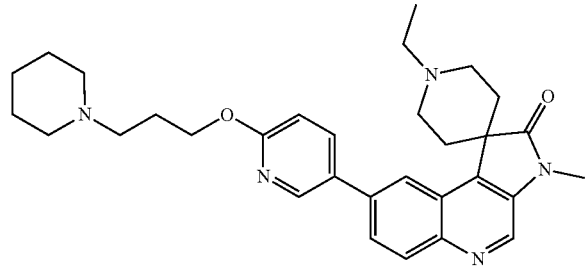
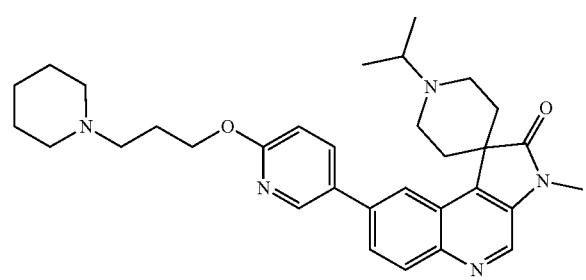
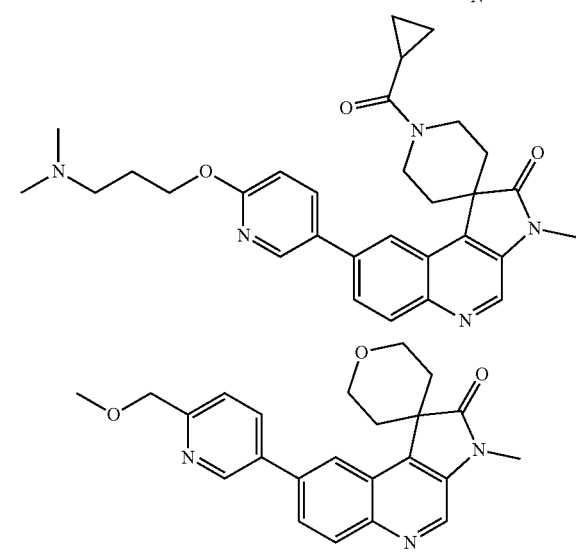
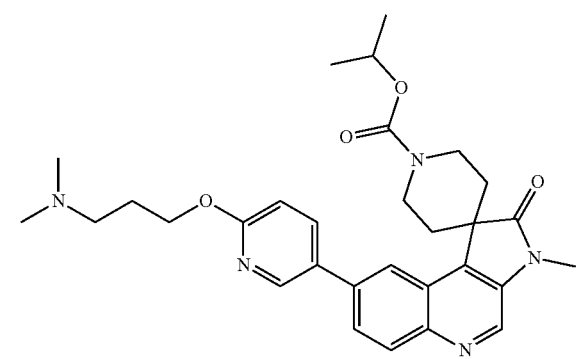
98
-continued
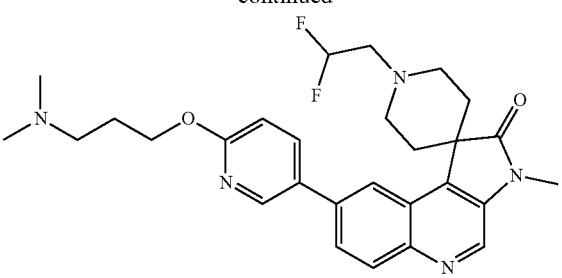
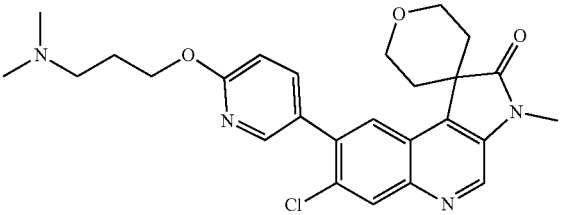
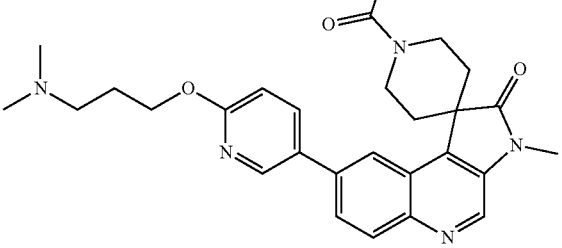
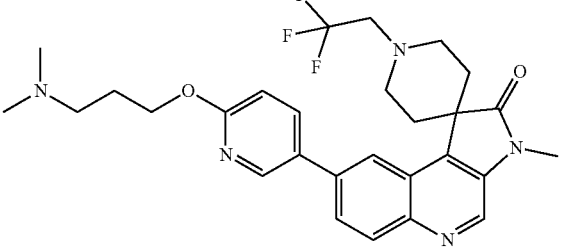
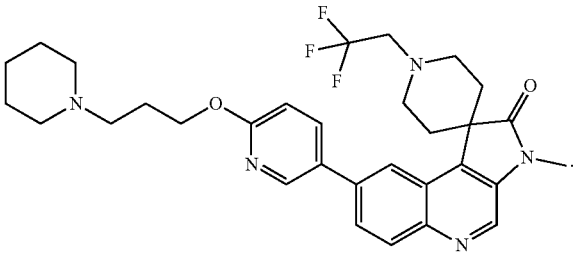
22. The compound, isomer thereof or pharmaceutically acceptable salt thereof as defined in claim 21, selected from -continued
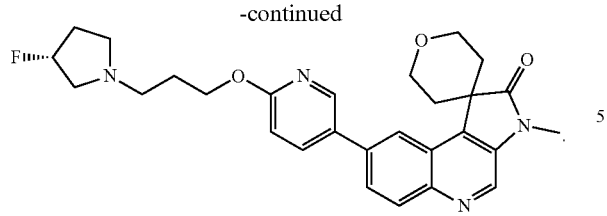
* * * * *